US012315604B2

(12) United States Patent
Jain et al.

(10) Patent No.: US 12,315,604 B2
(45) Date of Patent: May 27, 2025

(54) RECURRING REMOTE MONITORING WITH REAL-TIME EXCHANGE TO ANALYZE HEALTH DATA AND GENERATE ACTION PLANS

(71) Applicant: Evernorth Strategic Development, Inc., St. Louis, MO (US)

(72) Inventors: Neha Jain, Bridgewater, NJ (US); Kevin Herzig, Fort Myers, FL (US)

(73) Assignee: Evernorth Stragic Development, Inc., St. Louis, MO (US)

( * ) Notice: Subject to any disclaimer, the term of this patent is extended or adjusted under 35 U.S.C. 154(b) by 176 days.

(21) Appl. No.: 18/204,716

(22) Filed: Jun. 1, 2023

(65) Prior Publication Data

US 2023/0395213 A1 Dec. 7, 2023

Related U.S. Application Data

(60) Provisional application No. 63/348,398, filed on Jun. 2, 2022.

(51) Int. Cl.
*G16H 10/60* (2018.01)
*G16H 20/00* (2018.01)
*G16H 40/67* (2018.01)

(52) U.S. Cl.
CPC ............ *G16H 10/60* (2018.01); *G16H 20/00* (2018.01); *G16H 40/67* (2018.01)

(58) Field of Classification Search
CPC ......... G16H 10/60; G16H 40/67; G16H 20/00
See application file for complete search history.

(56) References Cited

U.S. PATENT DOCUMENTS

| 6,019,777 | A | * | 2/2000 | Mackenzie | A61F 2/958 606/198 |
| 6,039,688 | A | * | 3/2000 | Douglas | A61B 5/4866 600/300 |
| 6,260,022 | B1 | * | 7/2001 | Brown | G16H 10/60 705/2 |
| 6,269,339 | B1 | * | 7/2001 | Silver | G16H 20/60 600/300 |

(Continued)

FOREIGN PATENT DOCUMENTS

| CN | 109671475 A | 4/2019 |
| CN | 110046186 A | 7/2019 |

(Continued)

OTHER PUBLICATIONS

Qualtrics, Question Randomization, https://www.qualtrics.com/support/survey-platform/survey-module/block-options/question-randomization/, accessed Aug. 11, 2020.

*Primary Examiner* — Michael I Ezewoko
(74) *Attorney, Agent, or Firm* — Jordan IP Law, LLC

(57) ABSTRACT

Methods, apparatuses and systems provide technology to select a given group of monitoring information to collect from a user, and instruct a first computing device associated with the user to collect the given group of monitoring information. The technology determines that the given group of monitoring information is unavailable to be provided by the first computing device, and in response to the given group of monitoring information being determined as being unavailable to be provided by the first computing device, generates an outreach event to request the given group of monitoring information from the user.

20 Claims, 18 Drawing Sheets

(56) References Cited

U.S. PATENT DOCUMENTS

| | | | |
|---|---|---|---|
| 6,828,992 B1* | 12/2004 | Freeman | H04B 1/202 |
| | | | 715/810 |
| 6,904,408 B1* | 6/2005 | McCarthy | A61B 5/6815 |
| | | | 705/2 |
| 6,999,987 B1 | 2/2006 | Billingsley | |
| 7,076,534 B1* | 7/2006 | Cleron | G06F 16/9538 |
| | | | 709/219 |
| 7,086,007 B1* | 8/2006 | Bushey | G06F 8/38 |
| | | | 715/744 |
| 7,100,197 B2 | 8/2006 | Rail | |
| 7,103,556 B2 | 9/2006 | Del Rey | |
| 7,330,717 B2* | 2/2008 | Gidron | H04L 67/02 |
| | | | 455/418 |
| 7,433,828 B2 | 10/2008 | Brinkman | |
| 7,447,643 B1* | 11/2008 | Olson | G16Z 99/00 |
| | | | 706/46 |
| 7,448,047 B2 | 11/2008 | Poole | |
| 7,519,577 B2 | 4/2009 | Brundage | |
| 7,707,627 B2 | 4/2010 | Hirsh | |
| 7,730,063 B2* | 6/2010 | Eder | G06Q 40/06 |
| | | | 709/224 |
| 7,752,289 B2 | 7/2010 | Kikkawa | |
| 7,874,011 B2 | 1/2011 | Boss | |
| 7,953,613 B2* | 5/2011 | Gizewski | G16H 40/60 |
| | | | 705/2 |
| 7,979,894 B2 | 7/2011 | Royyuru | |
| 8,045,475 B2 | 10/2011 | Mohan | |
| 8,347,263 B1* | 1/2013 | Offer | G06F 9/44536 |
| | | | 717/174 |
| 8,401,871 B2 | 3/2013 | Fotsch | |
| 8,505,077 B2 | 8/2013 | Kulkarni | |
| 8,566,121 B2 | 10/2013 | Ramasubramanian | |
| 8,826,021 B2 | 9/2014 | Savage | |
| 8,924,236 B2 | 12/2014 | Marchosky | |
| 8,935,272 B2 | 1/2015 | Ganti | |
| 8,955,058 B2 | 2/2015 | Castro | |
| 8,979,627 B2 | 3/2015 | Walker | |
| 8,997,038 B2* | 3/2015 | Bozek | G06F 8/30 |
| | | | 717/106 |
| 9,134,964 B2* | 9/2015 | Hirsch | G06F 8/36 |
| 9,170,800 B2* | 10/2015 | Lang | G06F 21/57 |
| 9,195,822 B2 | 11/2015 | Carlson | |
| 9,239,834 B2 | 1/2016 | Donabedian | |
| 9,244,952 B2 | 1/2016 | Ganti | |
| 9,282,425 B2 | 3/2016 | Tomkins | |
| 9,305,059 B1 | 4/2016 | Glickman | |
| 9,361,011 B1* | 6/2016 | Burns | H04N 7/188 |
| 9,426,433 B1* | 8/2016 | Mazzarella | H04L 65/102 |
| 9,461,972 B1* | 10/2016 | Mehta | H04L 63/0435 |
| 9,497,178 B2 | 11/2016 | Chow | |
| 9,516,008 B2 | 12/2016 | Chow | |
| 9,563,784 B2 | 2/2017 | Meredith | |
| 9,686,674 B2 | 6/2017 | Lin | |
| 9,715,370 B2* | 7/2017 | Friedman | G06F 8/30 |
| 9,753,618 B1* | 9/2017 | Jain | G09B 7/02 |
| 9,787,692 B2 | 10/2017 | Peleg | |
| 9,836,778 B2 | 12/2017 | Lyman | |
| 9,842,034 B2 | 12/2017 | Heliker | |
| 9,844,725 B1* | 12/2017 | Durkin | G06Q 30/0601 |
| 9,848,061 B1* | 12/2017 | Jain | H04L 67/01 |
| 9,854,431 B2 | 12/2017 | Lin | |
| 9,858,063 B2* | 1/2018 | Jain | H04L 67/025 |
| 9,927,983 B2 | 3/2018 | Benisty | |
| 9,977,867 B2 | 5/2018 | Greene | |
| 9,983,775 B2* | 5/2018 | Jain | G06F 9/451 |
| 10,027,654 B2 | 7/2018 | Bringer | |
| 10,202,769 B2* | 2/2019 | Gya | H02G 3/263 |
| 10,205,769 B2* | 2/2019 | Sehgal | H04L 67/10 |
| 10,261,695 B2 | 4/2019 | Benisty | |
| 10,270,839 B2 | 4/2019 | Andreou | |
| 10,311,450 B2 | 6/2019 | Bjelajac | |
| 10,380,537 B2 | 8/2019 | Agasti | |
| 10,423,356 B2 | 9/2019 | Iyengar | |
| 10,437,841 B2 | 10/2019 | Robichaud | |
| 10,445,508 B2 | 10/2019 | Sher-Jan | |
| 10,475,140 B2 | 11/2019 | Patel | |
| 10,482,135 B2* | 11/2019 | Rychikhin | G06F 8/30 |
| 10,484,547 B2 | 11/2019 | Weeks | |
| 10,503,746 B2 | 12/2019 | Choudhary | |
| 10,515,188 B2 | 12/2019 | Soto | |
| 10,521,557 B2* | 12/2019 | Jain | G16H 50/30 |
| 10,565,509 B2 | 2/2020 | London | |
| 10,613,964 B2 | 4/2020 | Davis | |
| 10,621,880 B2 | 4/2020 | Boguraev | |
| 10,629,310 B2 | 4/2020 | Livesay | |
| 10,650,430 B2 | 5/2020 | Fine | |
| 10,659,399 B2 | 5/2020 | Foerster | |
| 10,691,774 B2 | 6/2020 | Thorpe | |
| 10,692,159 B2 | 6/2020 | Charkov | |
| 10,705,816 B2* | 7/2020 | Jain | H04L 67/025 |
| 10,706,971 B2 | 7/2020 | Ramaci | |
| 10,720,232 B2 | 7/2020 | Giordano | |
| 10,726,079 B2 | 7/2020 | Makaremi | |
| 10,733,546 B2 | 8/2020 | Pilkington | |
| 10,733,903 B2 | 8/2020 | Kurowski | |
| 10,762,990 B1* | 9/2020 | Schilling | G16B 40/30 |
| 10,775,974 B2* | 9/2020 | Schilling | G06F 3/0484 |
| 10,811,006 B2 | 10/2020 | Yamagami | |
| 10,817,589 B2 | 10/2020 | Lara | |
| 10,834,221 B2 | 11/2020 | Tong | |
| 10,860,655 B2 | 12/2020 | Murphey | |
| 10,915,605 B2 | 2/2021 | Stadler | |
| 10,964,430 B2 | 3/2021 | Willard | |
| 10,978,185 B2 | 4/2021 | Aagesen | |
| 10,997,251 B2 | 5/2021 | Tran | |
| 11,000,236 B2* | 5/2021 | Zhong | A61B 5/14532 |
| 11,107,563 B2 | 8/2021 | Vogt | |
| 11,238,979 B1* | 2/2022 | Schilling | G16B 40/00 |
| 11,615,642 B2* | 3/2023 | Chen | G06V 40/172 |
| | | | 382/118 |
| 11,651,620 B2* | 5/2023 | Chen | G06V 40/172 |
| | | | 382/118 |
| 11,657,646 B2* | 5/2023 | Chen | G16H 40/63 |
| | | | 382/118 |
| 11,923,079 B1* | 3/2024 | Schilling | G06Q 10/063 |
| 2001/0019338 A1* | 9/2001 | Roth | G06F 3/0482 |
| | | | 715/811 |
| 2002/0010596 A1* | 1/2002 | Matory | A61B 5/0002 |
| | | | 705/2 |
| 2002/0022973 A1* | 2/2002 | Sun | G16H 40/67 |
| | | | 705/3 |
| 2002/0065682 A1 | 5/2002 | Goldenberg | |
| 2002/0157091 A1* | 10/2002 | DeMello | G06Q 30/06 |
| | | | 717/178 |
| 2002/0194024 A1 | 12/2002 | Kleinschmidt | |
| 2003/0078960 A1* | 4/2003 | Murren | H04L 69/18 |
| | | | 709/203 |
| 2003/0165954 A1* | 9/2003 | Katagiri | C12Q 1/6883 |
| | | | 435/6.14 |
| 2003/0182429 A1* | 9/2003 | Jagels | H04L 67/14 |
| | | | 709/227 |
| 2003/0229522 A1* | 12/2003 | Thompson | G06Q 40/00 |
| | | | 705/348 |
| 2004/0030424 A1* | 2/2004 | Corl, Jr. | H04L 63/0263 |
| | | | 700/90 |
| 2004/0203755 A1* | 10/2004 | Brunet | H04W 8/18 |
| | | | 455/432.1 |
| 2004/0216054 A1* | 10/2004 | Mathews | H04M 1/72448 |
| | | | 715/744 |
| 2004/0267704 A1 | 12/2004 | Subramanian | |
| 2005/0050320 A1* | 3/2005 | Wassmann | G06F 8/70 |
| | | | 713/165 |
| 2005/0055687 A1* | 3/2005 | Mayer | G06F 8/65 |
| | | | 717/173 |
| 2005/0086587 A1* | 4/2005 | Balz | G06Q 30/02 |
| | | | 715/221 |
| 2005/0144072 A1* | 6/2005 | Perkowski | G06Q 30/0239 |
| | | | 705/14.49 |
| 2005/0159986 A1 | 7/2005 | Breeland | |
| 2005/0186550 A1* | 8/2005 | Gillani | G09B 7/04 |
| | | | 434/322 |

(56) References Cited

U.S. PATENT DOCUMENTS

| | | | |
|---|---|---|---|
| 2005/0246304 A1* | 11/2005 | Knight | G06F 8/34 |
| | | | 717/110 |
| 2006/0041452 A1* | 2/2006 | Kulkarni | G16H 10/20 |
| | | | 705/3 |
| 2006/0107219 A1* | 5/2006 | Ahya | G06F 9/465 |
| | | | 715/745 |
| 2006/0154642 A1 | 7/2006 | Scannell, Jr. | |
| 2006/0205564 A1* | 9/2006 | Peterson | A63B 69/00 |
| | | | 482/8 |
| 2006/0241972 A1* | 10/2006 | Lang | G16H 10/60 |
| | | | 705/2 |
| 2006/0271405 A1 | 11/2006 | Cipolle | |
| 2006/0282516 A1* | 12/2006 | Taylor | H04L 67/564 |
| | | | 709/220 |
| 2007/0021984 A1* | 1/2007 | Brown | G06Q 10/10 |
| | | | 706/924 |
| 2007/0038474 A1 | 2/2007 | Halsted | |
| 2007/0172844 A1* | 7/2007 | Lancaster | C12Q 1/6886 |
| | | | 435/6.12 |
| 2007/0219795 A1 | 9/2007 | Park | |
| 2007/0219958 A1 | 9/2007 | Park | |
| 2007/0231828 A1* | 10/2007 | Beachy | G01N 33/57434 |
| | | | 435/7.1 |
| 2007/0239516 A1 | 10/2007 | Smith | |
| 2007/0259351 A1* | 11/2007 | Chinitz | G16B 20/00 |
| | | | 435/6.12 |
| 2007/0281285 A1* | 12/2007 | Jayaweera | G09B 7/02 |
| | | | 434/188 |
| 2008/0005679 A1* | 1/2008 | Rimas-Ribikauskas | |
| | | | H04L 67/52 |
| | | | 715/745 |
| 2008/0021287 A1* | 1/2008 | Woellenstein | G16H 50/30 |
| | | | 600/300 |
| 2008/0034314 A1* | 2/2008 | Louch | G06F 3/0481 |
| | | | 715/764 |
| 2008/0046038 A1* | 2/2008 | Hill | A61N 1/37276 |
| | | | 607/60 |
| 2008/0126110 A1* | 5/2008 | Haeberle | G06F 9/542 |
| | | | 717/168 |
| 2008/0127040 A1* | 5/2008 | Barcellona | G06F 8/10 |
| | | | 717/101 |
| 2008/0177638 A1* | 7/2008 | Butler | H04L 67/34 |
| | | | 705/26.62 |
| 2008/0201174 A1* | 8/2008 | Ramasubramanian | |
| | | | G16H 20/10 |
| | | | 705/3 |
| 2008/0242221 A1* | 10/2008 | Shapiro | H04W 4/029 |
| | | | 455/3.06 |
| 2008/0243038 A1* | 10/2008 | Bennett | G16H 40/63 |
| | | | 601/33 |
| 2008/0254429 A1* | 10/2008 | Woolf | G09B 7/02 |
| | | | 706/45 |
| 2008/0261191 A1* | 10/2008 | Woolf | G09B 7/00 |
| | | | 434/323 |
| 2008/0301118 A1* | 12/2008 | Chien | G06F 16/954 |
| | | | 707/999.005 |
| 2008/0311968 A1* | 12/2008 | Hunter | A63F 13/30 |
| | | | 463/1 |
| 2009/0023555 A1* | 1/2009 | Raymond | G16H 70/20 |
| | | | 434/262 |
| 2009/0024944 A1* | 1/2009 | Louch | G06F 9/5033 |
| | | | 715/764 |
| 2009/0031215 A1* | 1/2009 | Collier, II | G06F 40/186 |
| | | | 715/255 |
| 2009/0035733 A1* | 2/2009 | Meitar | G09B 7/00 |
| | | | 434/118 |
| 2009/0043689 A1* | 2/2009 | Yang | G06Q 20/102 |
| | | | 705/38 |
| 2009/0076856 A1* | 3/2009 | Darby | G16H 40/67 |
| | | | 705/2 |
| 2009/0119678 A1* | 5/2009 | Shih | H04L 51/00 |
| | | | 719/313 |
| 2009/0125333 A1* | 5/2009 | Heywood | G06Q 50/22 |
| | | | 705/2 |
| 2009/0150814 A1* | 6/2009 | Eyer | G06F 3/04842 |
| | | | 715/765 |
| 2009/0156190 A1* | 6/2009 | Fisher | G06F 3/0484 |
| | | | 455/418 |
| 2009/0163182 A1* | 6/2009 | Gatti | H04M 1/72451 |
| | | | 455/414.1 |
| 2009/0170715 A1* | 7/2009 | Glinsky | C12Q 1/6886 |
| | | | 506/8 |
| 2009/0172002 A1* | 7/2009 | Ahmed | G06F 16/958 |
| | | | 707/999.102 |
| 2009/0248883 A1* | 10/2009 | Suryanarayana | G06F 9/451 |
| | | | 709/229 |
| 2009/0276771 A1* | 11/2009 | Nickolov | G06Q 30/04 |
| | | | 718/1 |
| 2010/0041378 A1* | 2/2010 | Aceves | H04W 4/029 |
| | | | 455/414.1 |
| 2010/0042578 A1 | 2/2010 | Leuthardt | |
| 2010/0063367 A1* | 3/2010 | Friedman | A61B 5/0205 |
| | | | 600/490 |
| 2010/0082367 A1* | 4/2010 | Hains | G16H 20/10 |
| | | | 705/2 |
| 2010/0088245 A1 | 4/2010 | Harrison | |
| 2010/0122286 A1* | 5/2010 | Begeja | G06Q 30/02 |
| | | | 725/34 |
| 2010/0179833 A1* | 7/2010 | Roizen | G06Q 50/2057 |
| | | | 715/752 |
| 2010/0211941 A1* | 8/2010 | Roseborough | G06F 8/65 |
| | | | 717/170 |
| 2010/0250279 A1 | 9/2010 | Guggenheim | |
| 2010/0250341 A1* | 9/2010 | Hauser | H04L 67/02 |
| | | | 707/E17.042 |
| 2010/0262664 A1* | 10/2010 | Brown | H04W 28/12 |
| | | | 709/206 |
| 2010/0333037 A1* | 12/2010 | Pavlovski | G06F 3/0481 |
| | | | 715/848 |
| 2011/0126119 A1* | 5/2011 | Young | G06F 3/048 |
| | | | 715/744 |
| 2011/0184748 A1* | 7/2011 | Fierro | G16H 40/67 |
| | | | 705/2 |
| 2011/0200979 A1* | 8/2011 | Benson | G09B 7/00 |
| | | | 434/350 |
| 2011/0230360 A1* | 9/2011 | Stephan | C12Q 1/6886 |
| | | | 435/7.1 |
| 2011/0246251 A1 | 10/2011 | Saunders | |
| 2012/0047029 A1* | 2/2012 | Veres | G06Q 30/0277 |
| | | | 717/172 |
| 2012/0065987 A1* | 3/2012 | Farooq | G16H 50/70 |
| | | | 705/2 |
| 2012/0084399 A1* | 4/2012 | Scharber | H04L 67/34 |
| | | | 709/219 |
| 2012/0102050 A1* | 4/2012 | Button | G06N 5/022 |
| | | | 707/E17.014 |
| 2012/0143697 A1* | 6/2012 | Chopra | G06Q 30/0269 |
| | | | 705/14.66 |
| 2012/0215639 A1* | 8/2012 | Ramer | G06Q 30/0269 |
| | | | 705/14.64 |
| 2012/0220835 A1* | 8/2012 | Chung | A61B 5/6898 |
| | | | 600/301 |
| 2012/0260294 A1* | 10/2012 | Reichardt | H04N 21/482 |
| | | | 725/60 |
| 2012/0272156 A1* | 10/2012 | Kerger | H04M 3/487 |
| | | | 715/747 |
| 2013/0006064 A1* | 1/2013 | Reiner | A61B 5/0022 |
| | | | 600/300 |
| 2013/0103434 A1 | 4/2013 | Cazeaux | |
| 2013/0103749 A1* | 4/2013 | Werth | H04L 41/0816 |
| | | | 709/203 |
| 2013/0110565 A1* | 5/2013 | Means, Jr. | G06Q 10/06 |
| | | | 705/7.11 |
| 2013/0145457 A1* | 6/2013 | Papakipos | G06F 21/6245 |
| | | | 726/19 |
| 2013/0166494 A1* | 6/2013 | Davis | G06N 5/04 |
| | | | 706/54 |
| 2013/0179178 A1 | 7/2013 | Vemireddy | |

(56) References Cited

U.S. PATENT DOCUMENTS

| | | | |
|---|---|---|---|
| 2013/0179472 A1* | 7/2013 | Junqua | G06F 16/211 707/796 |
| 2013/0185097 A1* | 7/2013 | Saria | G06Q 10/00 705/3 |
| 2013/0212487 A1* | 8/2013 | Cote | G06F 9/451 715/745 |
| 2013/0238686 A1* | 9/2013 | O'Donoghue | G06F 9/4451 709/203 |
| 2013/0283188 A1* | 10/2013 | Sanghvi | G06F 3/0484 715/751 |
| 2013/0329632 A1* | 12/2013 | Buyukkoc | H04L 43/0882 370/328 |
| 2014/0019191 A1* | 1/2014 | Mulji | G06Q 10/06316 705/7.26 |
| 2014/0019480 A1* | 1/2014 | Rychikhin | G06F 16/951 707/770 |
| 2014/0026113 A1* | 1/2014 | Farooqi | G06F 8/36 717/107 |
| 2014/0033171 A1* | 1/2014 | Lorenz | G06F 8/34 717/121 |
| 2014/0052681 A1* | 2/2014 | Nitz | G06N 5/048 706/46 |
| 2014/0058755 A1* | 2/2014 | Macoviak | G06Q 10/10 705/2 |
| 2014/0074506 A1 | 3/2014 | Oliver | |
| 2014/0088995 A1* | 3/2014 | Damani | G16H 40/67 705/2 |
| 2014/0100883 A1* | 4/2014 | Hamilton | G16H 40/67 705/3 |
| 2014/0101628 A1* | 4/2014 | Almog | G06F 30/30 716/136 |
| 2014/0109072 A1* | 4/2014 | Lang | G06F 21/53 717/168 |
| 2014/0109115 A1* | 4/2014 | Low | G06F 9/54 719/328 |
| 2014/0109177 A1* | 4/2014 | Barton | H04L 67/34 726/1 |
| 2014/0156823 A1* | 6/2014 | Liu | H04L 41/20 709/223 |
| 2014/0181715 A1* | 6/2014 | Axelrod | H04M 1/72454 715/771 |
| 2014/0187228 A1* | 7/2014 | Fisher | G06Q 30/0277 455/418 |
| 2014/0210618 A1 | 7/2014 | Poe | |
| 2014/0214659 A1 | 7/2014 | Hansen | |
| 2014/0240122 A1* | 8/2014 | Roberts | G08B 3/10 340/539.11 |
| 2014/0249889 A1 | 9/2014 | Park | |
| 2014/0257058 A1* | 9/2014 | Clarysse | A61B 5/7275 600/301 |
| 2014/0257852 A1* | 9/2014 | Walker | G06Q 10/10 705/3 |
| 2014/0273913 A1* | 9/2014 | Michel | H04M 3/00 455/404.1 |
| 2014/0278536 A1* | 9/2014 | Zhang | G16H 10/60 705/3 |
| 2014/0282061 A1* | 9/2014 | Wheatley | H04N 21/4532 715/745 |
| 2014/0297308 A1 | 10/2014 | Baruch | |
| 2014/0297311 A1* | 10/2014 | Jackson | G06Q 30/0201 705/2 |
| 2014/0309868 A1* | 10/2014 | Ricci | G06Q 10/00 701/36 |
| 2014/0310306 A1 | 10/2014 | Sawczuk | |
| 2014/0316815 A1 | 10/2014 | Chen | |
| 2014/0358482 A1* | 12/2014 | Sehgal | G06Q 30/0601 709/201 |
| 2014/0365961 A1* | 12/2014 | Lefor | G06F 3/0482 715/810 |
| 2014/0372137 A1 | 12/2014 | Tryon | |
| 2015/0019342 A1* | 1/2015 | Gupta | G06Q 30/0269 705/14.66 |
| 2015/0025917 A1* | 1/2015 | Stempora | G02B 27/0093 705/4 |
| 2015/0025997 A1* | 1/2015 | Tilenius | G06F 16/90324 705/26.7 |
| 2015/0056589 A1* | 2/2015 | Zhang | G09B 19/003 434/236 |
| 2015/0074635 A1* | 3/2015 | Margiotta | G06F 8/20 717/105 |
| 2015/0089224 A1* | 3/2015 | Beckman | G06F 21/6218 713/168 |
| 2015/0135160 A1* | 5/2015 | Gauvin | G06F 8/34 717/109 |
| 2015/0142459 A1 | 5/2015 | Nichols | |
| 2015/0143470 A1* | 5/2015 | Stiekes | H04L 63/10 726/4 |
| 2015/0148061 A1* | 5/2015 | Koukoumidis | H04W 4/022 455/456.1 |
| 2015/0154002 A1* | 6/2015 | Weinstein | G06F 9/451 715/728 |
| 2015/0163121 A1* | 6/2015 | Mahaffey | H04L 41/142 707/687 |
| 2015/0199490 A1* | 7/2015 | Iancu | G16H 20/30 705/2 |
| 2015/0294090 A1* | 10/2015 | Kodiyan | G16Z 99/00 705/2 |
| 2015/0310559 A1 | 10/2015 | Kaafarani | |
| 2015/0339393 A1 | 11/2015 | Chung | |
| 2015/0347681 A1 | 12/2015 | Bartlett, II | |
| 2015/0350611 A1 | 12/2015 | Pearson | |
| 2015/0352363 A1* | 12/2015 | McIntyre | G16H 50/20 607/45 |
| 2015/0356701 A1* | 12/2015 | Gandy | G06Q 10/109 705/2 |
| 2016/0019316 A1 | 1/2016 | Murphey | |
| 2016/0058287 A1* | 3/2016 | Dyell | A61B 5/02055 340/870.07 |
| 2016/0086297 A1* | 3/2016 | Dettinger | G06Q 10/101 705/3 |
| 2016/0092339 A1* | 3/2016 | Straub | G06F 9/44521 717/124 |
| 2016/0110523 A1 | 4/2016 | Francois | |
| 2016/0173822 A1 | 6/2016 | Lemmey | |
| 2016/0189317 A1* | 6/2016 | Papandrea | G16H 10/60 705/319 |
| 2016/0234624 A1* | 8/2016 | Riva | H04W 4/60 |
| 2017/0011179 A1 | 1/2017 | Arshad | |
| 2017/0011200 A1* | 1/2017 | Arshad | G16H 30/20 |
| 2017/0020444 A1* | 1/2017 | Lurie | A61B 5/74 |
| 2017/0032394 A1 | 2/2017 | Stevens | |
| 2017/0048215 A1* | 2/2017 | Straub | H04L 63/0823 |
| 2017/0124276 A1* | 5/2017 | Tee | G16H 40/67 |
| 2017/0132395 A1* | 5/2017 | Futch | G06Q 40/08 |
| 2017/0180518 A1 | 6/2017 | Choi | |
| 2017/0270532 A1 | 9/2017 | Livesay | |
| 2017/0303187 A1* | 10/2017 | Crouthamel | H04W 48/10 |
| 2017/0329483 A1* | 11/2017 | Jann | G06F 40/106 |
| 2017/0329500 A1* | 11/2017 | Grammatikakis | G06F 3/0483 |
| 2017/0330297 A1* | 11/2017 | Cronin | A61B 5/6802 |
| 2017/0344895 A1* | 11/2017 | Roy | G06F 3/0484 |
| 2017/0374178 A1* | 12/2017 | Sharma | H04L 67/75 |
| 2017/0374568 A1 | 12/2017 | Heath | |
| 2018/0054710 A1 | 2/2018 | Gum | |
| 2018/0101659 A1 | 4/2018 | Ninan | |
| 2018/0121187 A1* | 5/2018 | Jain | H04L 67/34 |
| 2018/0197624 A1* | 7/2018 | Robaina | A61B 3/10 |
| 2018/0232492 A1* | 8/2018 | Al-Alul | G16H 20/30 |
| 2018/0247713 A1* | 8/2018 | Rothman | A61B 5/02055 |
| 2018/0268417 A1 | 9/2018 | Livesay | |
| 2018/0293234 A1 | 10/2018 | Resnofendri | |
| 2018/0308569 A1* | 10/2018 | Luellen | G16H 20/10 |
| 2019/0019581 A1* | 1/2019 | Vaughan | A61B 5/168 |
| 2019/0026663 A1* | 1/2019 | Homeyer | G06Q 10/0633 |
| 2019/0034589 A1 | 1/2019 | Chen | |
| 2019/0034590 A1 | 1/2019 | Oren | |
| 2019/0043501 A1* | 2/2019 | Ramaci | G16H 40/20 |
| 2019/0043610 A1* | 2/2019 | Vaughan | A61B 5/4088 |
| 2019/0043619 A1* | 2/2019 | Vaughan | G16H 50/30 |
| 2019/0052720 A1 | 2/2019 | Guo | |

(56) References Cited

U.S. PATENT DOCUMENTS

| | | | |
|---|---|---|---|
| 2019/0065499 A1 | 2/2019 | Wagstaff | |
| 2019/0074080 A1* | 3/2019 | Appelbaum | G16H 80/00 |
| 2019/0103173 A1 | 4/2019 | Power | |
| 2019/0138734 A1 | 5/2019 | Sher-Jan | |
| 2019/0172588 A1* | 6/2019 | Tran | G16H 50/30 |
| 2019/0180862 A1* | 6/2019 | Wisser | G16H 30/40 |
| 2019/0198181 A1 | 6/2019 | Livesay | |
| 2019/0207814 A1* | 7/2019 | Jain | G16H 20/00 |
| 2019/0214116 A1* | 7/2019 | Eberting | G16H 40/20 |
| 2019/0243944 A1* | 8/2019 | Jain | G16H 80/00 |
| 2019/0272925 A1 | 9/2019 | Barrett | |
| 2019/0286086 A1* | 9/2019 | Gardner | G05B 17/02 |
| 2019/0313934 A1* | 10/2019 | Lee | A61B 5/0002 |
| 2019/0320310 A1* | 10/2019 | Horelik | H04W 68/005 |
| 2020/0019995 A1* | 1/2020 | Krishnan | G16H 10/20 |
| 2020/0042577 A1 | 2/2020 | Kasa | |
| 2020/0050330 A1* | 2/2020 | Schilling | G06F 9/451 |
| 2020/0112479 A1* | 4/2020 | Jain | G16H 40/20 |
| 2020/0119986 A1* | 4/2020 | Jain | G16H 40/20 |
| 2020/0131581 A1* | 4/2020 | Jain | G16H 50/20 |
| 2020/0241859 A1* | 7/2020 | Jain | G06F 8/70 |
| 2020/0241860 A1* | 7/2020 | Jain | G06F 8/70 |
| 2020/0241895 A1 | 7/2020 | Voss | |
| 2020/0251194 A1 | 8/2020 | Vogt | |
| 2020/0278852 A1* | 9/2020 | Jain | H04L 67/34 |
| 2020/0322703 A1 | 10/2020 | Bures | |
| 2020/0342455 A1 | 10/2020 | Poteet, III | |
| 2020/0348919 A1* | 11/2020 | Jain | G16H 40/63 |
| 2020/0356353 A1* | 11/2020 | Jain | H04L 67/125 |
| 2021/0026615 A1* | 1/2021 | Jain | G06F 8/70 |
| 2022/0028513 A1 | 1/2022 | Gangaikondan-Iyer | |
| 2023/0393894 A1 | 12/2023 | Herzig | |
| 2023/0395204 A1 | 12/2023 | Mitjans | |
| 2023/0395213 A1 | 12/2023 | Jain | |
| 2023/0395214 A1 | 12/2023 | Needs | |
| 2023/0395215 A1 | 12/2023 | Long | |
| 2023/0395243 A1 | 12/2023 | Teeple | |

FOREIGN PATENT DOCUMENTS

| | | |
|---|---|---|
| CN | 110691548 A | 1/2020 |
| CN | 113380351 A | 9/2021 |
| EP | 3362890 A1 | 8/2018 |
| EP | 3489958 A1 | 5/2019 |
| EP | 3634204 A1 | 4/2020 |
| EP | 3799056 A1 | 3/2021 |
| KR | 101575146 B1 | 12/2015 |
| KR | 20200003407 A | 1/2020 |
| WO | 2001013274 A2 | 2/2001 |
| WO | 200120488 A1 | 3/2001 |
| WO | 2019022779 A1 | 1/2019 |

* cited by examiner

← 400

OUTREACH EVENT 1

┌─ 410
Blood pressure measurement is stale

┌─ 420
Tom, please re-measure your blood pressure with your blood pressure monitoring device ┌─ 430
Re-collect blood pressure measurement

OUTREACH EVENT 2

510

Blood pressure measurement is stale for Tom

520

Please contact Tom to obtain blood pressure measurement

530

Call Tom

FIG. 5

| Blood Pressure | Blood Pressure Frequency | Pulse | Weight | Swelling | Aerobic Activity | BMI | Sodium Intake | HGH A1C | LDL | HDL | ECG/EKG (IoT device) | Smoker | Pathway |
|---|---|---|---|---|---|---|---|---|---|---|---|---|---|
| <120/80 | | | | | 150 min/wk | <25 | <2300 mg | <5.6 | <100 | >40 | | | Stable |
| >120/80 | 2 weeks apart | | | | | >=25 | >2300 | >5.6 | >100 | <40 | | yes | Intervention |
| 160/100 | 2 consecutive days | | | | | | | >9 | | | Irregular Heartbeat | | Escalation |
| <130/80 | | <100 | | | Normal | | <2300 mg | | | | | | Reward/ Stable |
| | | | gain >2 lbs in 24 hours or >5 lbs in a week | | | | | | | | | | |
| 143-170/80-100 | | 100-120 | 3 lbs. in 24 hours | mild leg swelling | shortness of breath at activity | | | | | | | | Intervention |
| >170/100 | | >120 | | moderate to severe leg swelling | shortness of breath at rest | | | | | | | | Escalation |

RECURRING REMOTE MONITORING WITH REAL-TIME EXCHANGE TO ANALYZE HEALTH DATA AND GENERATE ACTION PLANS

CROSS-REFERENCE TO RELATED APPLICATIONS

The present application claims the benefit of priority to U.S. Patent Application No. 63/348,398 (filed on Jun. 2, 2022), which is hereby incorporated by reference in its entirety.

TECHNICAL FIELD

Embodiments generally relate to a computing platform that analyzes health data of a patient, determines if the health data indicates a health condition, and follows an action plan to mitigate and/or otherwise address the health condition. In particular, the computing platform remotely monitors the health data of the patient and provides the action plan.

BACKGROUND

Health can be monitored remotely in a variety of ways. Certain connected devices, such as blood pressure monitors, can be used by a patient to collect health information. Such information can be provided to a communication device of the patient and transmitted to one or more other parties, such as medical providers.

BRIEF DESCRIPTION OF THE DRAWINGS

FIGS. 4 and 5 are example user interfaces of the real-time health monitoring platform, according to example embodiments.

FIG. 10B is a diagram of an example of a health condition monitoring table according to an embodiment.

DETAILED DESCRIPTION

Figure 1:
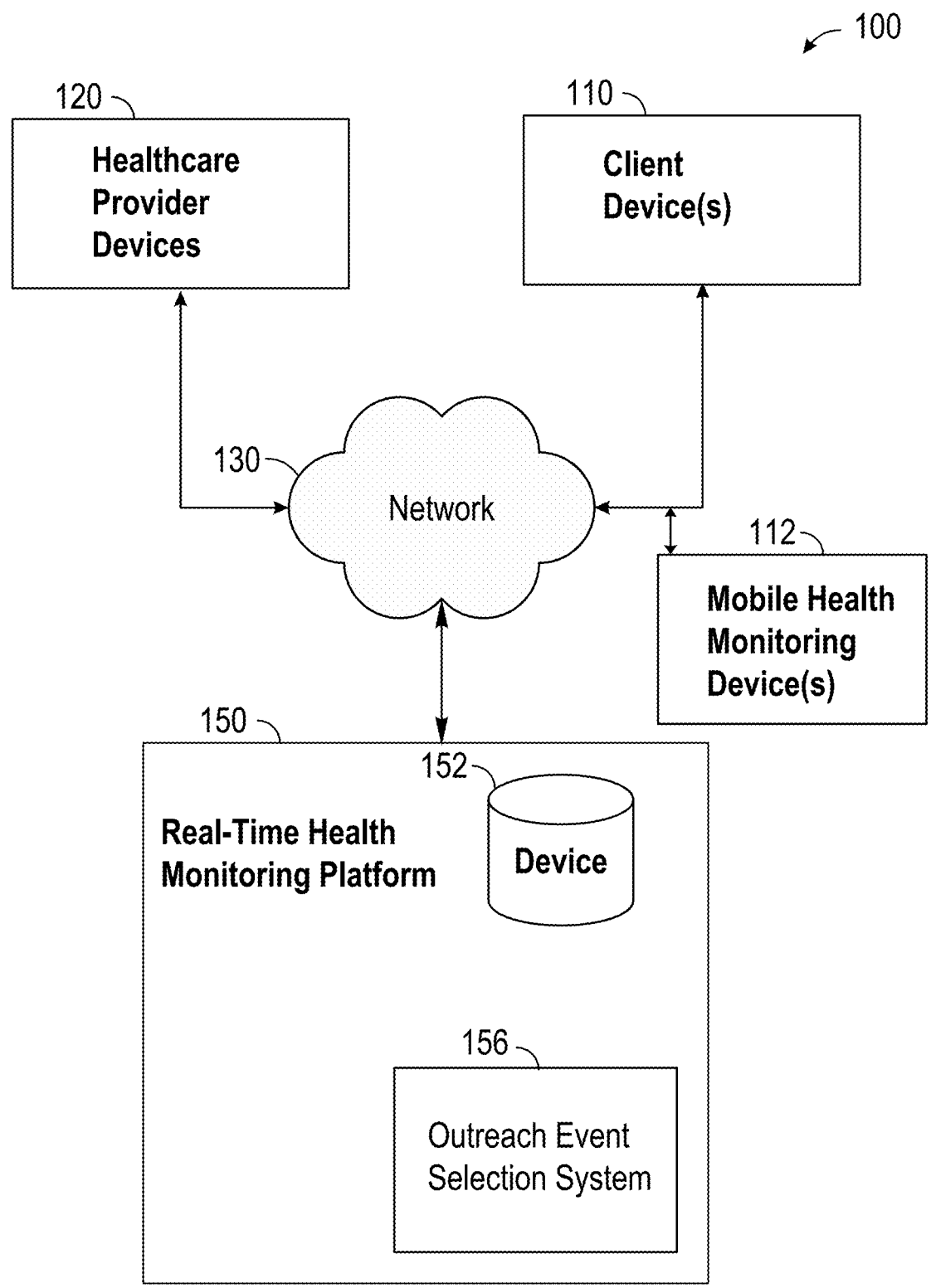
FIG. 1 is a block diagram of an example real-time health monitoring platform, according to some embodiments.

Example methods and systems for a real-time health monitoring platform are provided. In the following description, for purposes of explanation, numerous specific details are set forth in order to provide a thorough understanding of example embodiments. It will be evident, however, to one of ordinary skill in the art that embodiments of the invention may be practiced without these specific details.

Reoccurring Remote Monitoring Examples

Patient health information can be monitored by health providers remotely. For example, a health monitoring device, such as a blood pressure monitor, can be provided to a patient. The health monitoring device can collect a health measurement from the patient and can report back the collected health measurement to the health provider. Many times, the health information needs to be measured over a period of days, weeks or months in order to detect certain medical conditions. To do so, a patient needs to remember to use the health monitoring device to recollect the health measurement and to provide such a measurement to the provider. Having to remember to do so is incredibly inefficient and usually results in measurements being missed or skipped altogether. Some more sophisticated patients can setup manual reminders to collect the health measurements. But such reminders can be difficult to setup to be triggered at the right time and place which puts an enormous burden on patients and healthcare professionals. The healthcare professionals also need to continuously check various patients to ensure the measurements are diligently and timely collected which takes a great deal of time and resources away from performing other tasks, and is prone to error (e.g., human oversight).

Even when the measurements are collected at the right time by the patients, sometimes such measurements are not accurate. In such cases, the patient may need to re-collect the measurement after some period of time when the healthcare provider evaluates the measurement and informs the patient that the measurement was not accurate. This process is very frustrating and can cause patients to avoid interacting with the systems to remotely monitor their health.

The disclosed embodiments provide systems and methods to monitor patient health in real-time using mobile monitoring devices or equipment, such as Internet of Things (IoT) devices. The disclosed techniques select a given type (e.g., group such as blood pressure, glucose, etc.) of health monitoring information to collect from a patient. The disclosed techniques instruct a mobile device (e.g., a first computing device such as an IoT device) associated with the patient to collect the given type of health monitoring information. The IoT device includes at least one of a smart scale, a blood pressure cuff, a smart watch, an exercise bracelet, glucometer, a physiological sensor, and/or an ECG device. The given type of health monitoring information includes at least one of blood pressure information, aerobic activity information, body mass index (BMI) information, sodium intake information, arrhythmia information, and/or glucose information.

The disclosed techniques determine that the mobile device has failed to collect the given type of health monitoring information and, in response, generate an outreach event to request the given type of health monitoring information from the patient. The outreach event that is selected can be of a particular type that is suitable for the class of mobile device used to collect the given type of health monitoring information and/or the demographic or type of patient being monitored. This provides a very unique and tailored experience to patients in collecting their health monitoring information which improves the overall efficiency and process of collecting such information. The outreach event, in an example embodiment, can be positive reinforcement to the patient through an electronic device, a warning and/or an incentive to encourage collection of the health information from the monitoring device. The outreach event can be individualized (e.g., with a machine learning model) based on historical data about the type of patient, the medical state, the disease state, and/or a care pathway assigned to the patient.

In this way, the disclosed embodiments improve the overall process of providing medical care and specifically improves the efficiency at which health information is received from a patient. As a result, a great deal of time is saved and the patient can avoid navigating through a multitude of pages of information to provide health information. This saves time and reduces the amount of resources needed to accomplish a task. In an example, the collection of information is integrated into an interactive application run on a patient associated device. The application can be part of a care pathway (e.g., escalation, intervention, action, stable, etc.) that includes data collection events that pull sensed health data from patient assigned devices.

FIG. 1 is a block diagram showing an example health monitoring system 100 according to various exemplary embodiments. The health monitoring system 100 includes one or more client devices 110, one or more healthcare provider devices 120, and a real-time health monitoring platform 150, and one or more mobile health monitoring device(s) 112 that are communicatively coupled over a network 130 (e.g., Internet, telephony network). Each of the one or more mobile health monitoring device(s) 112 includes hardware and/or software configured to collect and/or measure a particular type of health monitoring information.

Each of the one or more mobile health monitoring device(s) 112 includes communication circuitry for electronically and automatically transmitting health information that is measured in real-time to the client device(s) 110, one or more healthcare provider devices 120 and/or the real-time health monitoring platform 150. For example, the one or more mobile health monitoring device(s) 112 can include IoT devices, such as a glucose monitor, a heart-rate monitor, a hand hygiene monitor, a mood monitor, a connected inhaler, a connected contact lens, a smart scale, a blood pressure cuff, a smart watch, an exercise bracelet, glucometer, an EKG device and/or an ECG device. In some cases, the mobile health monitoring device(s) 112 include storage circuitry for storing historically collected samples of the health information, such as all of the health information collected over a threshold period of time or in the lifetime of the given device. In some cases, some or all of the historical information can be stored at least partially on the client device 110 associated with the mobile health monitoring device(s) 112.

As used herein, the term "client device" may refer to any machine that interfaces to a communications network (such as network 130) to access the real-time health monitoring platform 150. The client device 110 may be, but is not limited to, a mobile phone, desktop computer, laptop, portable digital assistants (PDAs), smart phones, a wearable device (e.g., a smart watch), tablets, ultrabooks, netbooks, laptops, multi-processor systems, microprocessor-based or programmable consumer electronics, game consoles, set-top boxes, or any other communication device that a user may use to access a network or the real-time health monitoring platform 150.

The client device 110 can establish initially a secure connection with one or more mobile health monitoring device(s) 112. After establishing the secure connection, the mobile health monitoring device(s) 112 can be configured to exchange encrypted communications in real-time with the client device 110 with which the connection was established and/or one or more dedicated healthcare provider devices 120. In this way, a patient's health monitoring information remains securely stored on the patient's devices and cannot be compromised. This ensures that the health monitoring information is maintained private. In some cases, functionality of one or more of the mobile health monitoring device(s) 112 can be implemented by the client device 110. This can avoid the need to use a separate hardware device to collect a given type of health monitoring information.

In some cases, the real-time health monitoring platform 150 is accessible over a global communication system, e.g., the Internet or world-wide web. In such instances, the real-time health monitoring platform 150 hosts a website that is accessible to the client devices 110 and/or mobile health monitoring device(s) 112. Upon accessing the website, the client devices 110 provide secure login credentials, which are used to access a profile associated with the login credentials. One or more user interfaces associated with the real-time health monitoring platform 150 are provided over the Internet via the website to the client devices 110.

Healthcare provider devices 120 can include the same or similar functionality as client devices 110 for accessing the real-time health monitoring platform 150. In some cases, the healthcare provider devices 120 are used by "internal" users. Internal users are personnel, such as physicians, clinicians, healthcare providers, health-related coaches pharmacy benefit manager (PBM) operators, pharmacists, specialty pharmacy operators or pharmacists, or the like that are associated with or employed by an organization that provides the real-time health monitoring platform 150. In some cases, the healthcare provider devices 120 are used by "external" users. External users are personnel, such as physicians, clinicians, and health-related coaches that are associated with or employed by a different (external) organization than that which provides the real-time health monitoring platform 150. In some cases, the healthcare provider devices 120 receive real-time exchanges of data, such as messages from mobile health monitoring device(s) 112, via the real-time health monitoring platform 150 with the patient's permission. In other cases, the healthcare provider devices 120 communicate directly with the mobile health monitoring device(s) 112 to obtain the messages that include health monitoring information with the patient's permission.

The healthcare provider devices 120, when used by internal or external users, to access the real-time health monitoring platform 150 can view many records associated with many different patients (or users associated with client devices 110). Different levels of authorization can be associated with different internal and different external users to control which records the internal and external users have access. In some instances, only records associated with those patients to which a given internal or external user is referred, are made accessible and available to the given internal or external user device. Sometimes, a first internal or external user can refer a patient or records associated with the patient to a second internal or external user. In such circumstances, the second internal or external user becomes automatically authorized to access and view the patient's records that were referred by the first internal or external user.

In some examples, the real-time health monitoring platform 150 (and specifically the outreach event selection system 156) can implement a machine learning technique or machine learning model, such as a neural network (discussed below in connection with FIG. 9). The machine learning technique can be trained to establish a relationship between a plurality of training mobile device class features and re-reading requests. In an example, the machine learning technique can be trained by obtaining a batch of training data that includes a first set of the plurality of training mobile device class features (e.g., types of blood pressure cuffs, types of weight scales, age of weight scales and/or blood pressure cuffs, etc.) associated with re-reading requests.

The first set of the plurality of training mobile device class features can be processed by the machine learning technique to generate an estimated need for a re-reading request. For example, the machine learning technique can generate a probability that a first reading is inaccurate based on one or more corresponding features of the first set of the plurality of training mobile device class features, and request a re-reading to obtain a second reading and verify the accuracy when the probability meets a re-reading threshold. A loss can be computed based on a deviation between the estimated need for a re-reading request (e.g., an estimated number of times that re-readings should be requested) and the re-reading request (e.g., the actual number of re-reading requests that were issued) associated with the first set of the plurality of training mobile device class features. Parameters of the machine learning technique can then be updated based on the computed loss. These training operations can be repeated for multiple batches of training data and/or until a stopping criterion is reached.

In this way, a given class of mobile health monitoring device 112 can be intelligently, dynamically and selectively instructed to re-read or re-collect a set of health monitoring information based on an output of the machine learning model. This can ensure that the readings or samples of the health monitoring information collected by the given class of mobile health monitoring device 112 is accurate when provided to the healthcare provider devices 120 or processed to determine a need for an outreach event or alert.

The network 130 may include, or operate in conjunction with, an ad hoc network, an intranet, an extranet, a virtual private network (VPN), a local area network (LAN), a wireless network, a low energy Bluetooth (BLE) connection, a WiFi direct connection, a wireless LAN (WLAN), a wide area network (WAN), a wireless WAN (WWAN), a metropolitan area network (MAN), the Internet, a portion of the Internet, a portion of the Public Switched Telephone Network (PSTN), a plain old telephone service (POTS) network, a cellular telephone network, a wireless network, a Wi-Fi® network, another type of network, or a combination of two or more such networks. For example, a network or a portion of a network may include a wireless or cellular network and the coupling may be a Code Division Multiple Access (CDMA) connection, a Global System for Mobile communications (GSM) connection, or other type of cellular or wireless coupling. In this example, the coupling may implement any of a variety of types of data transfer technology, such as Single Carrier Radio Transmission Technology (1×RTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, fifth generation wireless (5G) networks, Universal Mobile Telecommunications System (UMTS), High Speed Packet Access (HSPA), Worldwide Interoperability for Microwave Access (WiMAX), Long Term Evolution (LTE) standard, others defined by various standard setting organizations, other long range protocols, or other data transfer technology. In some embodiments, the communication network can transmit the data in an encrypted format.

The healthcare provider devices 120 can be used to access pharmacy claims, medical data (e.g., medical information 230 stored in database 152), laboratory data and the like for one or more patients that the healthcare provider devices 120 are authorized to view. This patient information 210 can be maintained in a database 152 by the real-time health monitoring platform 150 or in a third-party database accessible to the real-time health monitoring platform 150 and/or the healthcare provider devices 120.

In some embodiments, the client devices 110 and the real-time health monitoring platform 150 can be communicatively coupled via an audio call (e.g., VoIP, Public Switched Telephone Network, cellular communication network, etc.) or via electronic messages (e.g., online chat, instant messaging, text messaging, email, and the like). While FIG. 1 illustrates a single client device 110 and a single healthcare provider device 120, it is understood that a plurality of such devices can be included in the system 100 in other embodiments. As used herein, the term "client device" may refer to any machine that interfaces to a communications network (such as network 130) to obtain resources from one or more server systems or other client devices.

The real-time health monitoring platform 150 can be an automated agent, e.g., on behalf of an organization. The automated agent can include a computing device that executes instructions stored therein or a device that executes instructions and provides a human machine interface. The automated agent can be associated with a medical group that includes the member. The automated agent can be an interactive voice response (IVR), a virtual online assistant, or a chatbot provided on a website. During a communication session between the user and the agent, the real-time health monitoring platform 150 identifies the member using initial context data (e.g., the phone number the member is calling from, the website login information inputted, automatic number identification (ANI), etc.) and retrieves the data on the member (e.g., member account information, name, address, insurance information, information on spouse and dependents, etc.) to be presented on the client device 110.

In some embodiments, the real-time health monitoring platform 150 includes an outreach event selection system 156. In some examples, the outreach event selection system 156 can receive data from one or more mobile health monitoring devices 112. Based on the received data, the outreach event selection system 156 selects a particular type of outreach event to perform. For example, the outreach event selection system 156 can receive health monitoring information of a particular type (or group, such as blood pressure, glucose, eye pressure, etc.) that fails to satisfy a criterion associated with the particular type of health monitoring information. For example, the outreach event selection system 156 can receive blood pressure measurement from a given mobile health monitoring device 112. The outreach event selection system 156 can compare the blood pressure measurement to a range of normal blood pressure measurements associated with an age group of the patient from which the blood pressure measurement was received. In response to determining that the blood pressure measurement is outside the normal range, the outreach event selection system 156 determines that the criterion associated with the blood pressure measurement fails to be satisfied. In such cases, the outreach event selection system 156 selects an outreach event that includes communicating with a healthcare provider device 120 to instruct a healthcare professional to contact the patient associated with the given mobile health monitoring device 112 from which the health monitoring information was received.

As another example, the given mobile health monitoring device 112 can transmit to the outreach event selection system 156 a timestamp indicating a last time that a particular type of health monitoring information was collected from the patient. The outreach event selection system 156 can compare the timestamp to a current time to measure a duration of time. If the duration of time exceeds a threshold (e.g., is more than 3 days indicating that the particular type of health monitoring information is stale), the outreach event selection system 156 can select an outreach event that triggers a notification or message to be presented on the client device 110 of the patient that is associated with or coupled to the mobile health monitoring device 112. The message can be transmitted by the outreach event selection system 156 via an SMS, automated phone call, chat, push notification or any other communication means. The message can inform the patient to collect the particular type of health monitoring information because the previous sample of the particular type of health monitoring information is stale. As another example, the outreach event can include transmission of a message to the healthcare provider device 120 instructing a healthcare professional to directly contact (e.g., by way of a phone call) the patient to instruct the patient to collect the particular type of health monitoring information.

The outreach event selection system 156 can store one or more rules for selecting the type of outreach event for different types of health monitoring information and types of patients and/or classes mobile health monitoring devices 112. The one or more rules can be automatically updated and/or generated with a machine learning model (e.g., a generative artificial intelligence model).

For example, the type of outreach event can be adjusted based on specific characteristics of the patient that is to receive the outreach event. That is, patient information can be analyzed to detect preferences, demographic information (e.g., age group) of the patient and so forth. The machine learning model can adjust the phrasing and/or type of outreach event based on the preferences and demographic information (e.g., patient specific information). Doing so can increase the effectiveness of the outreach, and increase the probability that the patient responds, follows and/or complies with instructions of the outreach event to provide health monitoring information. For example, suppose that the patient is a younger person (e.g., 25 years old) and the real-time health monitoring platform 150 is attempting to obtain blood pressure information. The phrasing of the outreach event can be adjusted to provide reasons why a younger person should be vigilant with blood pressure monitoring (e.g., "are you aware that young people who have moderate to high blood pressure that gradually rises over time may be at risk for poor brain health later in life? Let's monitor your blood pressure and develop a plan to reduce your blood pressure over time! Please take your blood pressure reading!").

The outreach events can also be adjusted based on specific historical information of the patient that is to receive the outreach event. For example, the machine learning model can efficiently and quickly analyze historical information of the patient. The machine learning model can identify habits based on the historical information that the patient is more likely to embrace. For example, suppose that from the patient information (e.g., historical data), the machine learning model determines that the patient poorly monitors blood sugar levels when the "finger stick check" method is suggested (e.g., the patient routinely fails to provide sugar readings when the "finger stick check" method is suggested as part of the outreach). In the "finger stick check," the patient pricks a fingertip with a small needle called a lancet to produce a blood drop. The drop of blood is placed against a test strip in a glucose meter, and the glucose meter displays blood glucose levels within the blood. Rather than suggesting the "finger stick check" method, examples can identify an alternative suggestion, and rather suggest that the patient obtain a continuous glucose monitoring (CGM) sensor and/or system to automatically provide glucose readings to the real-time health monitoring platform 150.

In some examples, the outreach event selection system 156 selects a given type of health monitoring information to collect from a patient. For example, a patient can input various medical information via a graphical user interface in the client device 110. The client device 110 can communicate with the real-time health monitoring platform 150 to provide the medical information about the patient. The real-time health monitoring platform 150 can then select a particular type of mobile health monitoring device 112 to monitor a health condition of the patient. For example, the medical information can indicate that the patient has high blood pressure. In such cases, the real-time health monitoring platform 150 can select a blood pressure monitoring device as the mobile health monitoring device 112 to use to periodically collect blood pressure measurements from the patient. As another example, the medical information can indicate that the patient suffers from diabetes. In such cases, the real-time health monitoring platform 150 can select a CGM device as the mobile health monitoring device 112 (e.g., a computing device) to use to periodically collect blood glucose measurements from the patient.

In some examples, a generative machine learning model can also be incorporated. The generative machine learning model can answer questions of the patient. For example, suppose that the patient receives an outreach event stating that a CGM device should be utilized to obtain glucose measurements, but has questions regarding how to use the CGM device, where to obtain the CGM device and so forth. The generative machine learning model can provide answers to the patient to increase the probability of patient compliance with instructions of the outreach event.

The outreach event selection system 156 instructs the mobile health monitoring device 112 (e.g., mobile IoT device) associated with the patient to collect the given type of health monitoring information. The outreach event selection system 156 can determine that the mobile health monitoring device 112 has failed to collect the given type of health monitoring information. For example, the outreach event selection system 156 can determine that an elapsed time since the last sample was received from the mobile health monitoring device 112 meets, exceeds or transgresses a threshold (e.g., the last sample was received more than 3 days ago, where 2 days is the threshold). In response, the outreach event selection system 156 generates an outreach event to request the given type of health monitoring information from the patient.

In some examples, the outreach event selection system 156 accesses previously collected health monitoring information associated with the patient. For example, the outreach event selection system 156 can obtain a history of health monitoring information collected from the patient over a past week, month, year or any other period. The history can include a variety of different types of health monitoring information, such as blood pressure measurements, heart rate measurements, blood glucose level measurement, and so forth. The outreach event selection system 156 searches the previously collected health monitoring information for the given type of health monitoring information. Specifically, the outreach event selection system 156 can be configured to monitor blood pressure measurements from the patient. In such cases, the outreach event selection system 156 can search or retrieve only blood pressure measurements or instances from the history of blood pressure measurements. The outreach event selection system 156 accesses a timestamp associated with the retrieved instance of the health monitoring information (e.g., the blood pressure measurement) and measures a duration of time between a current time and the timestamp. The outreach event selection system 156 compares the duration of time to a threshold and causes the outreach event to be generated in response to determining that the duration of time transgresses the threshold. In some cases, the outreach event selection system 156 selects a particular type of outreach event associated with a historical measurement (last measurement) of health information being received more than a threshold time than a current time.

In some examples, if health information is missing, the real-time health monitoring platform 150 can retrieve the health information from other sources rather than reaching out to a patient and/or selecting an outreach event. For example, longitudinal patient records can incorporate the internal/external health history of individuals, external events (e.g., manual patient reports, lab work, electronic medical records, etc.).

In some examples, the outreach event selection system 156 receives the given type of health monitoring information from the mobile device and determines that a value of the received given type of health monitoring information fails to satisfy a criterion. For example, the outreach event selection system 156 can determine that a blood pressure measurement falls outside of a normal range associated with the patient. In response, the outreach event selection system 156 instructs the mobile health monitoring device 112 to recollect or re-read the given type of health monitoring information.

In some examples, as explained in more detail in connection with FIG. 3, the outreach event selection system 156 is trained based on training patient information features (e.g., patient health information, patient demographic information, patient in-network insurance coverage, patient out-of-network insurance coverage, patient location, or one or more treatment preferences) and their corresponding ground-truth types of service of care. The outreach event selection system 156 is trained to predict type of service of care for a given set of patient information features. The prediction can be used to select a type of service of care to recommend to a patient.

In some examples, the outreach event that is selected includes a reminder message transmitted to the client device 110 of the patient. Each reminder message includes a notification for the patient to provide or recollect the given type of health monitoring information using the mobile health monitoring device 112. The outreach event selection system 156 can continue to send reminder messages to the client device 110 over a period of time. The outreach event selection system 156 can determine that a quantity of the reminder messages previously sent to the client device 110 transgresses a threshold quantity (e.g., more than 3 reminders have been sent). The outreach event selection system 156 further determines that updated health monitoring information has not been received from the mobile health monitoring device 112 since the time the first reminder message was sent to the client device 110. In such cases, the outreach event selection system 156 can select a different outreach event, such as an outreach event that includes transmitting a message to a healthcare provider device 120 associated with a medical provider.

In some examples, the outreach event selection system 156 can determine a class associated with the mobile health monitoring device 112 from which a selected type of health monitoring information is received. The outreach event selection system 156 can maintain a list of different classes or types of health monitoring devices 112 that are associated with inaccurate readings or sample collections. The outreach event selection system 156 determines that the class associated with the mobile health monitoring device 112 matches or corresponds to the class or type of health monitoring devices 112 that are on the list. In response, the outreach event selection system 156 can select an outreach event that includes instructing the health monitoring devices 112 to re-collect the given type of health monitoring information. In some examples, the outreach event selection system 156 applies a trained neural network or machine learning model to the class of the mobile health monitoring device 112 to estimate a need for re-reading the health monitoring information. In response to obtaining a prediction from the machine learning model that the class of the mobile health monitoring device 112 requires re-reading, the outreach event selection system 156 selects an outreach event to instruct the mobile health monitoring device 112 to re-collect the sample of the health monitoring information.

In some examples, the outreach event selection system 156 determining a type associated with the patient associated with the mobile health monitoring device 112 from which the health monitoring information was received. The type can represent a demographic, medical information (condition), gender and/or age group of the patient. The outreach event selection system 156 can instruct the mobile device to re-collect the given type of health monitoring information based on determining the type associated with the patient. Specifically, certain types of patients may need to be requested to perform a re-reading (e.g., to recollect a sample of health monitoring information). As an example, a female patient that is 20 years old may be able hold her arm steady to collect a good sample of health monitoring information, such as a blood pressure measurement. For such a patient, a re-reading request may not be needed. As another example, a male patient that is 50 years old may not capable of holding his arm steady and so the sample of health monitoring information could be inaccurate. For such a patient, the outreach event selection system 156 can request that the mobile health monitoring device 112 re-collect the health monitoring information. As another example, a patient that has a certain medical condition, such as Parkinson's, may be incapable of holding their arm steady and so the sample of health monitoring information could be inaccurate. For such a patient, the outreach event selection system 156 can request that the mobile health monitoring device 112 re-collect the health monitoring information.

Figure 2:
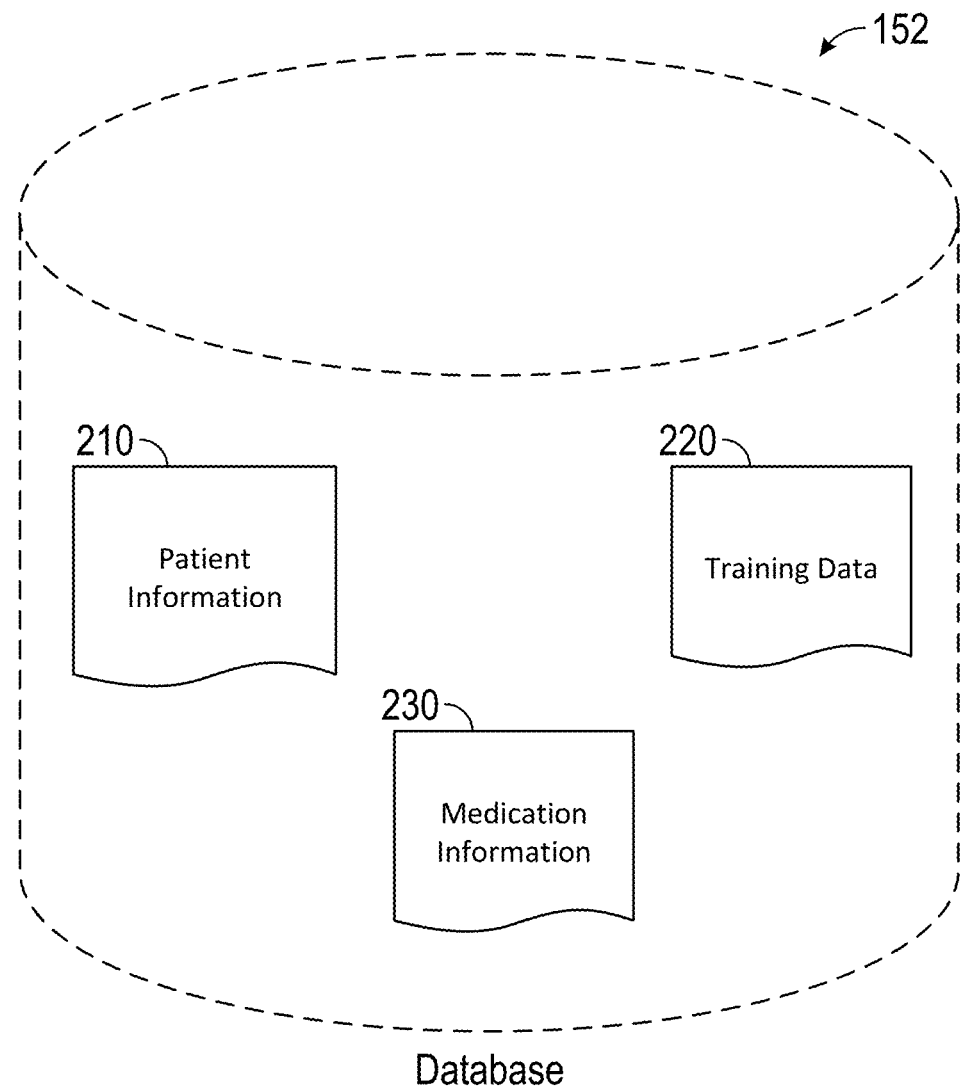
FIG. 2 is an example database that may be deployed within the system of FIG. 1, according to some embodiments.

FIG. 2 is an example database 152 that may be deployed within the system of FIG. 1, according to some embodiments. The database 152 includes patient information 210, medication information 230, and training data 220. The patient information 210 can be generated by the real-time health monitoring platform 150. For example, the real-time health monitoring platform 150 can access one or more patient records from one or more sources, including pharmacy claims, benefit information, prescribing physician information, dispensing information (e.g., where and how the patient obtains their current medications), demographic information, prescription information including dose quantity and interval, and input from a patient received via a user interface presented on the client device 110 and so forth. The real-time health monitoring platform 150 can collect this information from the patient records and generates a patient features vector that includes this information.

The medication information 230 stores various medication related information (e.g., prescriptions, size of the medication or pills, compatible forms of dispensing information, temperature control information, mixing exclusion information, and so forth) for various medications. The medication information 230 can include a history of different samples or instances of health monitoring information collected from a variety of patients. The history can include timestamps for each health monitoring information indicating when that health monitoring information was collected from the mobile health monitoring device 112. The history can be stored in an encrypted manner. In this way, a patient can access their own health monitoring information and not health monitoring information of any other patient using their respectively assigned encryption/decryption key. The history of medical information can be accessed by the outreach event selection system 156 to determine how much time has elapsed since a last health monitoring information instance was collected and to select a particular type of outreach event to perform or trigger.

The training data 220 includes training sets of the plurality of training mobile device class features associated with re-reading requests. The training data 220 is used to train a machine learning model implemented by the outreach event selection system 156 to generate estimates of needs to perform re-reading requests. For example, the training data 220 can be built over time by identifying a first set of the plurality of training mobile device class features that are associated with a need to perform a re-reading.

Figure 3:
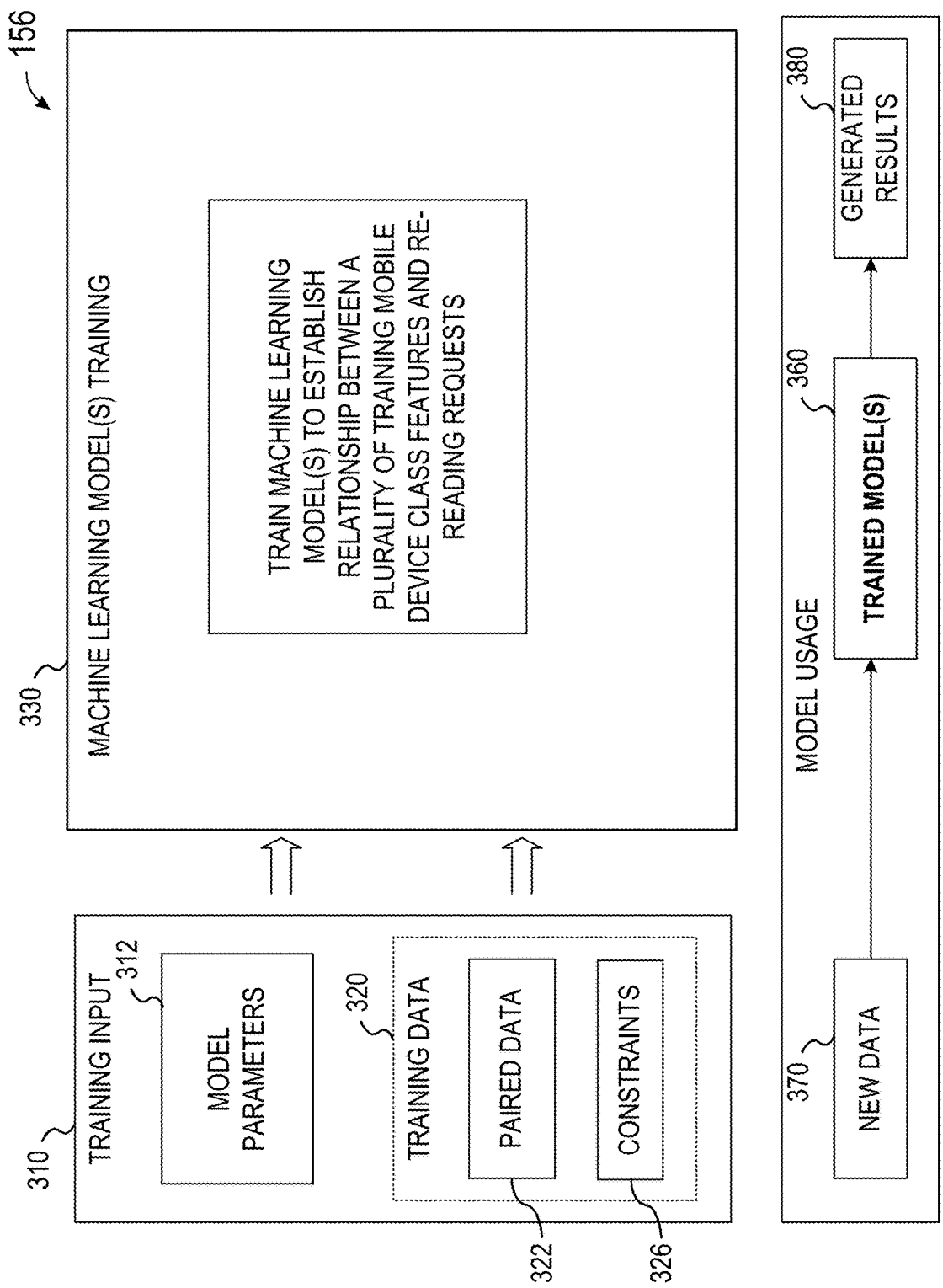
FIG. 3 is a block diagram of an example outreach event selection system that may be deployed within the system of FIG. 1, according to some embodiments.

FIG. 3 is a block diagram of an example outreach event selection system 156 that may be deployed within the system of FIG. 1, according to some embodiments. Training input 310 includes model parameters 312 and training data 320 (e.g., training data 220 (FIG. 2)) which may include paired training data sets 322 (e.g., input-output training pairs) and constraints 326. Model parameters 312 stores or provides the parameters or coefficients of corresponding ones of machine learning models. During training, these model parameters 312 are adapted based on the input-output training pairs of the training data sets 322. After the model parameters 312 are adapted (after training), the parameters are used by trained models 360 to implement the trained machine learning models on a new set of data 370.

Training data 320 includes constraints 326 which may define the constraints of a given patient information features. The paired training data sets 322 may include sets of input-output pairs, such as a pairs of a plurality of training mobile device class features and re-reading requests associated with the training mobile device class features. Some components of training input 310 may be stored separately at a different off-site facility or facilities than other components.

Machine learning model(s) training 330 trains one or more machine learning techniques based on the sets of input-output pairs of paired training data sets 322. For example, the machine learning model(s) training 330 may train the model parameters 312 (e.g., machine learning (ML) parameters) by minimizing a loss function based on one or more ground-truth type of needs to perform re-reading requests. The ML model can include any one or combination of classifiers or neural networks, such as an artificial neural network, a convolutional neural network, an adversarial network, a generative adversarial network, a deep feed forward network, a radial basis network, a recurrent neural network, a long/short term memory network, a gated recurrent unit, an auto encoder, a variational autoencoder, a denoising autoencoder, a sparse autoencoder, a Markov chain, a Hopfield network, a Boltzmann machine, a restricted Boltzmann machine, a deep belief network, a deep convolutional network, a deconvolutional network, a deep convolutional inverse graphics network, a liquid state machine, an extreme learning machine, an echo state network, a deep residual network, a Kohonen network, a support vector machine, a neural Turing machine, and the like.

Particularly, the ML model can be applied to a training plurality of mobile device class features to estimate or generate a prediction of a need to perform a re-reading request. In some implementations, a derivative of a loss function is computed based on a comparison of the estimated need to perform a re-reading request and the ground truth re-reading requests and parameters of the ML model are updated based on the computed derivative of the loss function.

In one example, the ML model receives a batch of training data that includes a first set of the plurality of training mobile device class features together with a ground-truth re-reading requests need. The ML model generates a feature vector based on the first set of the plurality of training mobile device class features and generates a prediction of a need to perform a re-reading request. The prediction is compared with the ground truth need for re-reading and parameters of the ML model are updated based on the comparison.

The result of minimizing the loss function for multiple sets of training data trains, adapts, or optimizes the model parameters 312 of the corresponding ML models. In this way, the ML model is trained to establish a relationship between a plurality of training mobile device class features and re-reading requests.

After the machine learning model is trained, new data 370, including a class of a mobile device features are received. The trained machine learning technique may be applied to the new data 370 to generate results 380 including a prediction of a need to perform a re-reading request.

FIGS. 4 and 5 are example user interfaces 400 and 500 of the health monitoring system 100, according to example embodiments. For example, a client device 110 can provide medical information (patient information) associated with a patient to the outreach event selection system 156. To do so, the client device 110 can present a graphical user interface through which the patient inputs various patient information. The patient can also input a request for medical services, such as a request to schedule an appointment, fulfill a prescription, or view a list of medical providers.

In response to receiving, the request from the client device 110, the outreach event selection system 156 can select a type of health monitoring information to collect from the patient using the mobile health monitoring device 112 of the patient. The outreach event selection system 156 can determine that the mobile health monitoring device 112 has failed to collect a given type of health monitoring information and, in response, the outreach event selection system 156 can trigger a particular type of outreach event. In one example, the outreach event selection system 156 can trigger an outreach event that includes a reminder or notification provided to the client device 110 of the patient.

In some examples, in response to receiving the outreach event, the client device 110 can present a user interface 400 (FIG. 4). The user interface 400 includes an identification 410 of the outreach event (e.g., blood pressure measurement is stale—the elapsed time since the blood pressure measurement exceeds a threshold time). The user interface 400 includes a message 420 informing the patient to re-collect or to perform an action for collecting the health monitoring information, such as by wearing a blood pressure monitoring device. The user interface 400 includes an option 430 to re-sample or to collect the health monitoring information (e.g., an option to re-collect the blood pressure measurement). In response to receiving input that selects the option 430, the mobile health monitoring device 112 of the patient is activated and measures the health monitoring information. Once the mobile health monitoring device 112 completes measuring or collecting the health monitoring information, the mobile health monitoring device 112 transmits the information to the outreach event selection system 156 in real-time.

In some examples, the outreach event is transmitted to the healthcare provider device 120. In such cases, in response to receiving the outreach event, the healthcare provider device 120 can present a user interface 500 (FIG. 5). The user interface 500 includes an identification 510 of the outreach event (e.g., blood pressure measurement is stale—the elapsed time since the blood pressure measurement exceeds a threshold time) including an identification of the patient. The user interface 500 includes a message 520 informing the provider to contact the patient to instruct the patient to recollect the health monitoring information. The user interface 500 includes an option 530 to contact the patient. In response to receiving input that selects the option 530, the healthcare provider device 120 transmits a communication in real-time to the client device 110 of the patient, such as by way of an SMS, a phone call, a push notification, or other communication to instruct the patient to recollect the health monitoring information.

Figure 6:
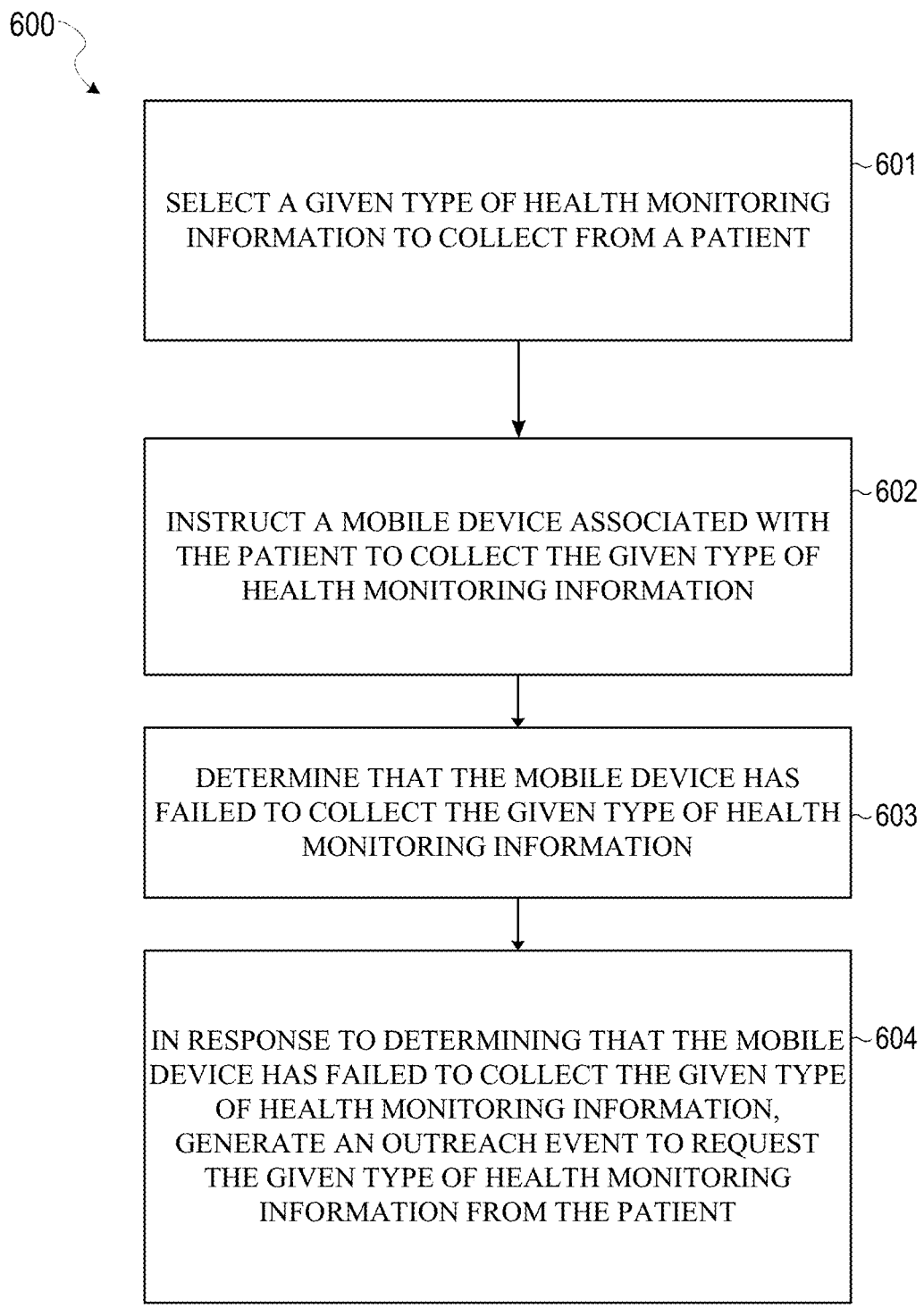
FIG. 6 is a flowchart illustrating example operations of the real-time health monitoring platform, according to example embodiments.

FIG. 6 is a flowchart illustrating example operations of the service of care type selection system in performing process 600, according to example embodiments. The process 600 may be embodied in computer-readable instructions for execution by one or more processors such that the operations of the process 600 may be performed in part or in whole by the functional components of the system 100; accordingly, the process 600 is described below by way of example with reference thereto. However, in other embodiments, at least some of the operations of the process 600 may be deployed on various other hardware configurations. Some or all of the operations of process 600 can be in parallel, out of order, or entirely omitted.

At operation 601, the system 100 selects a given type of health monitoring information to collect from a patient, as discussed above.

At operation 602, the system 100 instructs a mobile device associated with the patient to collect the given type of health monitoring information, as discussed above.

At operation 603, the system 100 determines that the mobile device has failed to collect the given type of health monitoring information, as discussed above.

At operation 604, the system 100, in response to determining that the mobile device has failed to collect the given type of health monitoring information, generates an outreach event to request the given type of health monitoring information from the patient, as discussed above.

Figure 7:
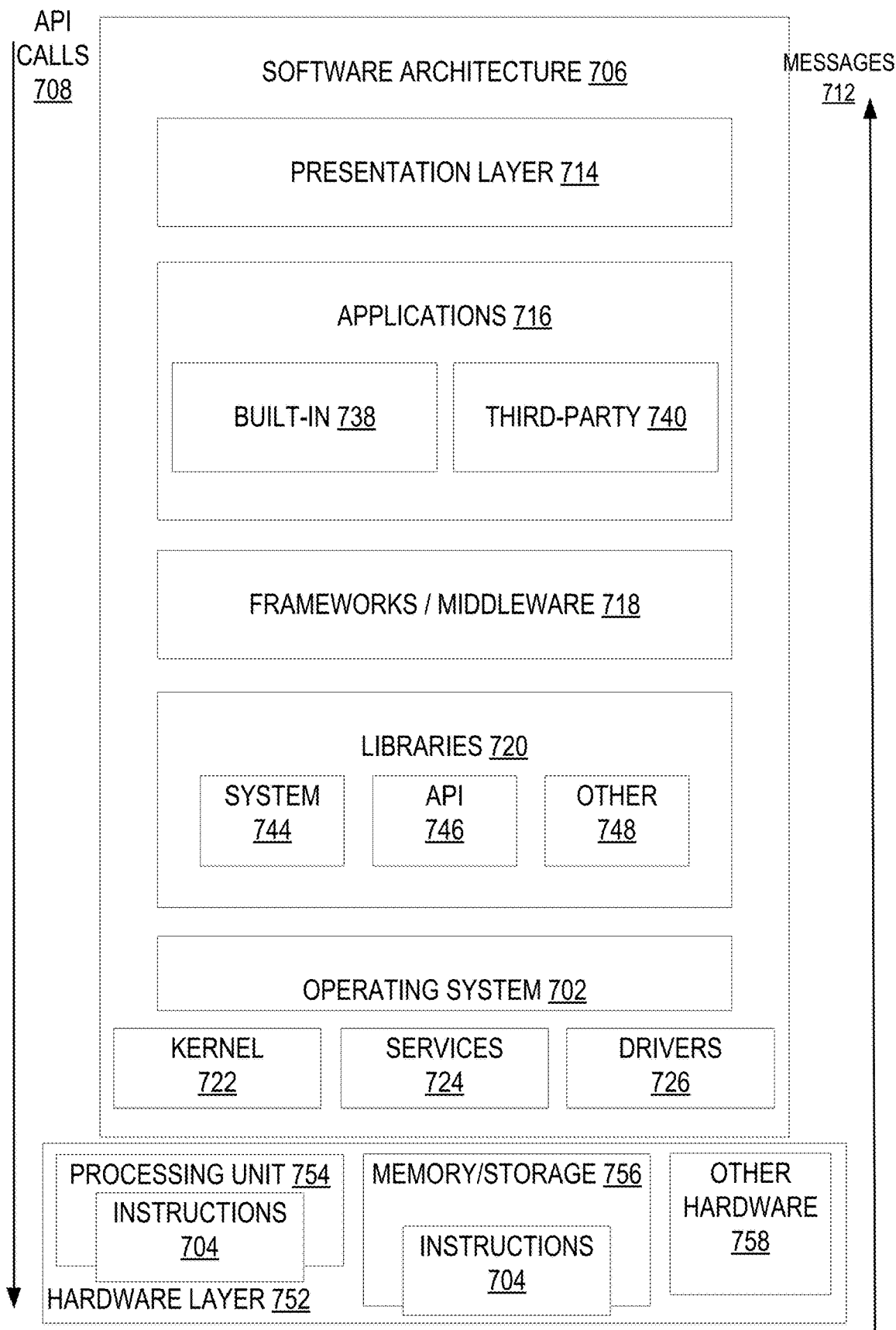
FIG. 7 is a block diagram illustrating an example software architecture, which may be used in conjunction with various hardware architectures herein described.

FIG. 7 is a block diagram illustrating an example software architecture 706, which may be used in conjunction with various hardware architectures herein described. FIG. 7 is a non-limiting example of a software architecture and it will be appreciated that many other architectures may be implemented to facilitate the functionality described herein. The software architecture 706 may execute on hardware such as machine 800 of FIG. 8 that includes, among other things, processors 804, memory 814, and input/output (I/O) components 818. A representative hardware layer 752 is illustrated and can represent, for example, the machine 800 of FIG. 8. The representative hardware layer 752 includes a processing unit 754 having associated executable instructions 704. Executable instructions 704 represent the executable instructions of the software architecture 706, including implementation of the methods, components, and so forth described herein. The hardware layer 752 also includes memory and/or storage devices memory/storage 756, which also have executable instructions 704. The hardware layer 752 may also comprise other hardware 758. The software architecture 706 may be deployed in any one or more of the components shown in FIG. 1. The software architecture 706 can be utilized to apply a machine learning technique or model to generate a prediction of a need to perform re-reading for a particular class of mobile health monitoring device 112 of a patient. The software architecture 706 can be utilized to select an outreach event to perform from a plurality of different types of outreach events based on failure to collect a given type of health monitoring information from a mobile health monitoring device 112.

In the example architecture of FIG. 7, the software architecture 706 may be conceptualized as a stack of layers where each layer provides particular functionality. For example, the software architecture 706 may include layers such as an operating system 702, libraries 720, frameworks/middleware 718, applications 716, and a presentation layer 714. Operationally, the applications 716 and/or other components within the layers may invoke API calls 708 through the software stack and receive messages 712 in response to the API calls 708. The layers illustrated are representative in nature and not all software architectures have all layers. For example, some mobile or special purpose operating systems may not provide a frameworks/middleware 718, while others may provide such a layer. Other software architectures may include additional or different layers.

The operating system 702 may manage hardware resources and provide common services. The operating system 702 may include, for example, a kernel 722, services 724, and drivers 726. The kernel 722 may act as an abstraction layer between the hardware and the other software layers. For example, the kernel 722 may be responsible for memory management, processor management (e.g., scheduling), component management, networking, security settings, and so on. The services 724 may provide other common services for the other software layers. The drivers 726 are responsible for controlling or interfacing with the underlying hardware. For instance, the drivers 726 include display drivers, camera drivers, Bluetooth® drivers, flash memory drivers, serial communication drivers (e.g., Universal Serial Bus (USB) drivers), Wi-Fi® drivers, audio drivers, power management drivers, and so forth depending on the hardware configuration.

The libraries 720 provide a common infrastructure that is used by the applications 716 and/or other components and/or layers. The libraries 720 provide functionality that allows other software components to perform tasks in an easier fashion than to interface directly with the underlying operating system 702 functionality (e.g., kernel 722, services 724 and/or drivers 726). The libraries 720 may include system libraries 744 (e.g., C standard library) that may provide functions such as memory allocation functions, string manipulation functions, mathematical functions, and the like. In addition, the libraries 720 may include API libraries 746 such as media libraries (e.g., libraries to support presentation and manipulation of various media format such as MPREG4, H.264, MP3, AAC, AMR, JPG, PNG), graphics libraries (e.g., an OpenGL framework that may be used to render two-dimensional and three-dimensional in a graphic content on a display), database libraries (e.g., SQLite that may provide various relational database functions), web libraries (e.g., WebKit that may provide web browsing functionality), and the like. The libraries 720 may also include a wide variety of other libraries 748 to provide many other APIs to the applications 716 and other software components/devices.

The frameworks/middleware 718 (also sometimes referred to as middleware) provide a higher-level common infrastructure that may be used by the applications 716 and/or other software components/devices. For example, the frameworks/middleware 718 may provide various graphic user interface functions, high-level resource management, high-level location services, and so forth. The frameworks/middleware 718 may provide a broad spectrum of other APIs that may be utilized by the applications 716 and other software components/devices, some of which may be specific to a particular operating system 702 or platform.

The applications 716 include built-in applications 738 and/or third-party applications 740. Examples of representative built-in applications 738 may include, but are not limited to, a contacts application, a browser application, a book reader application, a location application, a media application, a messaging application, and/or a game application. Third-party applications 740 may include an application developed using the ANDROID™ or IOS™ software development kit (SDK) by an entity other than the vendor of the particular platform, and may be mobile software running on a mobile operating system such as IOS™ ANDROID™, WINDOWS® Phone, or other mobile operating systems. The third-party applications 740 may invoke the API calls 708 provided by the mobile operating system (such as operating system 702) to facilitate functionality described herein.

The applications 716 may use built-in operating system functions (e.g., kernel 722, services 724, and/or drivers 726), libraries 720, and frameworks/middleware 718 to create UIs to interact with users of the system. Alternatively, or additionally, in some systems, interactions with a user may occur through a presentation layer, such as presentation layer 714. In these systems, the application/component "logic" can be separated from the aspects of the application/component that interact with a user.

Figure 8:
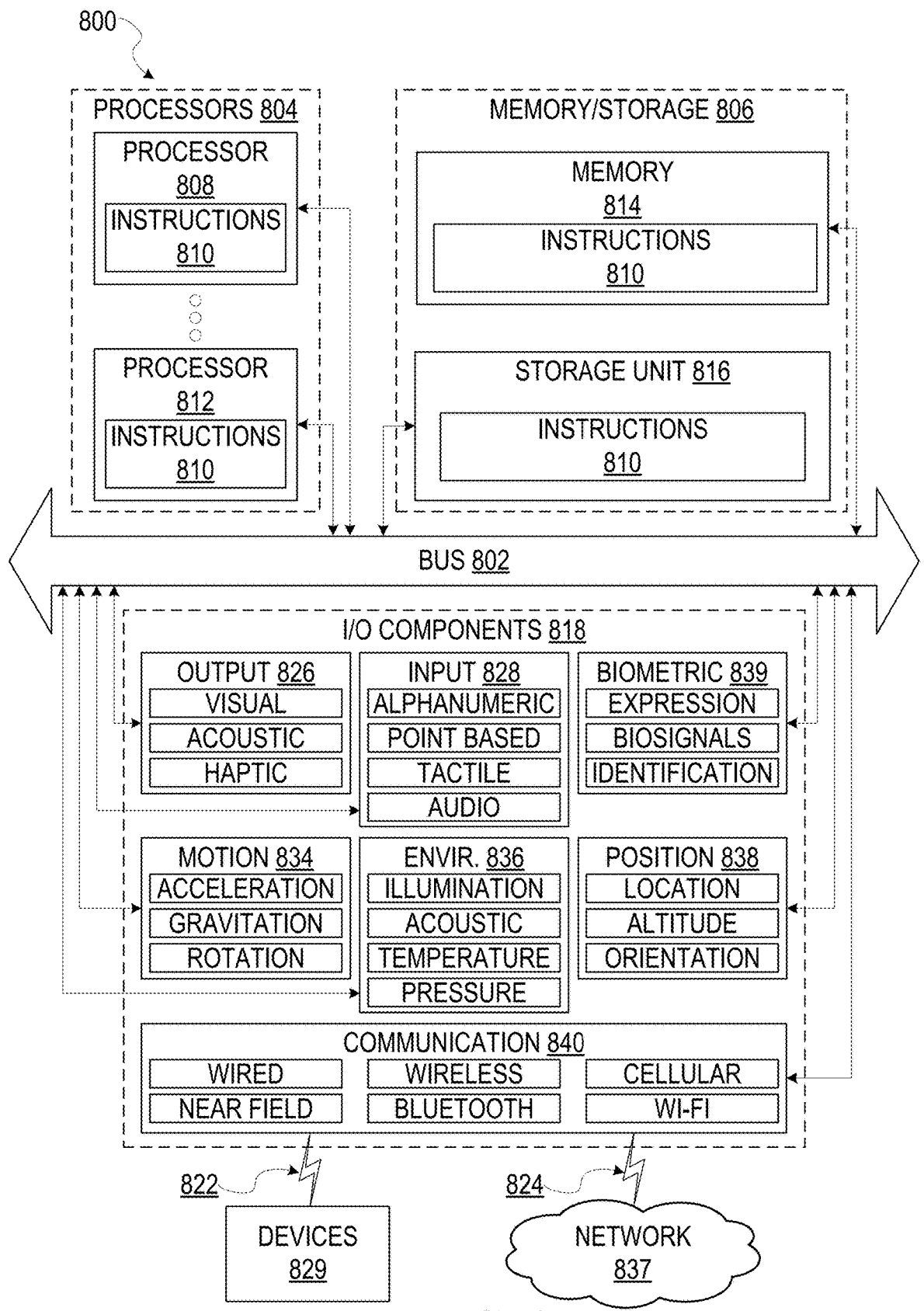
FIG. 8 is a block diagram illustrating components of a machine, according to some example embodiments.

FIG. 8 is a block diagram illustrating components of a machine 800, according to some example embodiments, able to read instructions from a machine-readable medium (e.g., a machine-readable storage medium) and perform any one or more of the methodologies discussed herein. Specifically, FIG. 8 shows a diagrammatic representation of the machine 800 in the example form of a computer system, within which instructions 810 (e.g., software, a program, an application, an applet, an app, or other executable code) for causing the machine 800 to perform any one or more of the methodologies discussed herein may be executed. For example, the instructions 810 may be executed by the system 100 to process a combination of patient information features with a trained machine learning model to predict a need to perform a re-reading request for a class of mobile health monitoring device 112.

As such, the instructions 810 may be used to implement devices or components described herein. The instructions 810 transform the machine 800 (e.g., a general, non-programmed machine) into a particular machine programmed to carry out the described and illustrated functions in the manner described. In alternative embodiments, the machine 800 operates as a standalone device or may be coupled (e.g., networked) to other machines. In a networked deployment, the machine 800 may operate in the capacity of a server machine or a client machine in a server-client network environment, or as a peer machine in a peer-to-peer (or distributed) network environment. The machine 800 may comprise, but not be limited to a server computer, a client computer, a personal computer (PC), a tablet computer, a laptop computer, a netbook, a STB, a PDA, an entertainment media system, a cellular telephone, a smart phone, a mobile device, a wearable device (e.g., a smart watch), a smart home device (e.g., a smart appliance), other smart devices, a web appliance, a network router, a network switch, a network bridge, or any machine capable of executing the instructions 810, sequentially or otherwise, that specify actions to be taken by machine 800. Further, while only a single machine 800 is illustrated, the term "machine" shall also be taken to include a collection of machines that individually or jointly execute the instructions 810 to perform any one or more of the methodologies discussed herein.

The machine 800 may include processors 804, memory/storage 806, and I/O components 818, which may be configured to communicate with each other such as via a bus 802. In an example embodiment, the processors 804 (e.g., a central processing unit (CPU), a reduced instruction set computing (RISC) processor, a complex instruction set computing (CISC) processor, a graphics processing unit (GPU), a digital signal processor (DSP), an application-specific integrated circuit (ASIC), a radio-frequency integrated circuit (RFIC), another processor, or any suitable combination thereof) may include, for example, a processor 808 and a processor 812 that may execute the instructions 810. The term "processor" is intended to include multi-core processors 804 that may comprise two or more independent processors (sometimes referred to as "cores") that may execute instructions contemporaneously. Although FIG. 8 shows multiple processors 804, the machine 800 may include a single processor with a single core, a single processor with multiple cores (e.g., a multi-core processor), multiple processors with a single core, multiple processors with multiple cores, or any combination thereof.

The memory/storage 806 may include a memory 814, such as a main memory, or other memory storage, database 152, and a storage unit 816, both accessible to the processors 804 such as via the bus 802. The storage unit 816 and memory 814 store the instructions 810 embodying any one or more of the methodologies or functions described herein. The instructions 810 may also reside, completely or partially, within the memory 814, within the storage unit 816, within at least one of the processors 804 (e.g., within the processor's cache memory), or any suitable combination thereof, during execution thereof by the machine 800. Accordingly, the memory 814, the storage unit 816, and the memory of processors 804 are examples of machine-readable media.

The I/O components 818 may include a wide variety of components to receive input, provide output, produce output, transmit information, exchange information, capture measurements, and so on. The specific I/O components 818 that are included in the machine 800 will depend on the type of machine. For example, portable machines such as mobile phones will likely include a touch input device or other such input mechanisms, while a headless server machine will likely not include such a touch input device. It will be appreciated that the I/O components 818 may include many other components that are not shown in FIG. 8. The I/O components 818 are grouped according to functionality merely for simplifying the following discussion and the grouping is in no way limiting. In various example embodiments, the I/O components 818 may include output components 826 and input components 828. The output components 826 may include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The input components 828 may include alphanumeric input components (e.g., a keyboard, a touch screen configured to receive alphanumeric input, a photo-optical keyboard, or other alphanumeric input components), point-based input components (e.g., a mouse, a touchpad, a trackball, a joystick, a motion sensor, or other pointing instrument), tactile input components (e.g., a physical button, a touch screen that provides location and/or force of touches or touch gestures, or other tactile input components), audio input components (e.g., a microphone), and the like.

In further example embodiments, the I/O components 818 may include biometric components 839, motion components 834, environmental components 836, or position components 838 among a wide array of other components. For example, the biometric components 839 may include components to detect expressions (e.g., hand expressions, facial expressions, vocal expressions, body gestures, or eye tracking), measure biosignals (e.g., blood pressure, heart rate, body temperature, perspiration, or brain waves), identify a person (e.g., voice identification, retinal identification, facial identification, fingerprint identification, or electroencephalogram based identification), and the like. The motion components 834 may include acceleration sensor components (e.g., accelerometer), gravitation sensor components, rotation sensor components (e.g., gyroscope), and so forth. The environmental components 836 may include, for example, illumination sensor components (e.g., photometer), temperature sensor components (e.g., one or more thermometer that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that may provide indications, measurements, or signals corresponding to a surrounding physical environment. The position components 838 may include location sensor components (e.g., a GPS receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 818 may include communication components 840 operable to couple the machine 800 to a network 837 or devices 829 via coupling 824 and coupling 822, respectively. For example, the communication components 840 may include a network interface component or other suitable device to interface with the network 837. In further examples, communication components 840 may include wired communication components, wireless communication components, cellular communication components, Near Field Communication (NFC) components, Bluetooth® components (e.g., Bluetooth® Low Energy), Wi-Fi® components, and other communication components to provide communication via other modalities. The devices 829 may be another machine or any of a wide variety of peripheral devices (e.g., a peripheral device coupled via a USB).

Moreover, the communication components 840 may detect identifiers or include components operable to detect identifiers. For example, the communication components 840 may include Radio Frequency Identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information may be derived via the communication components 840, such as location via Internet Protocol (IP) geo-location, location via Wi-Fi® signal triangulation, location via detecting a NFC beacon signal that may indicate a particular location, and so forth.

Figure 9:
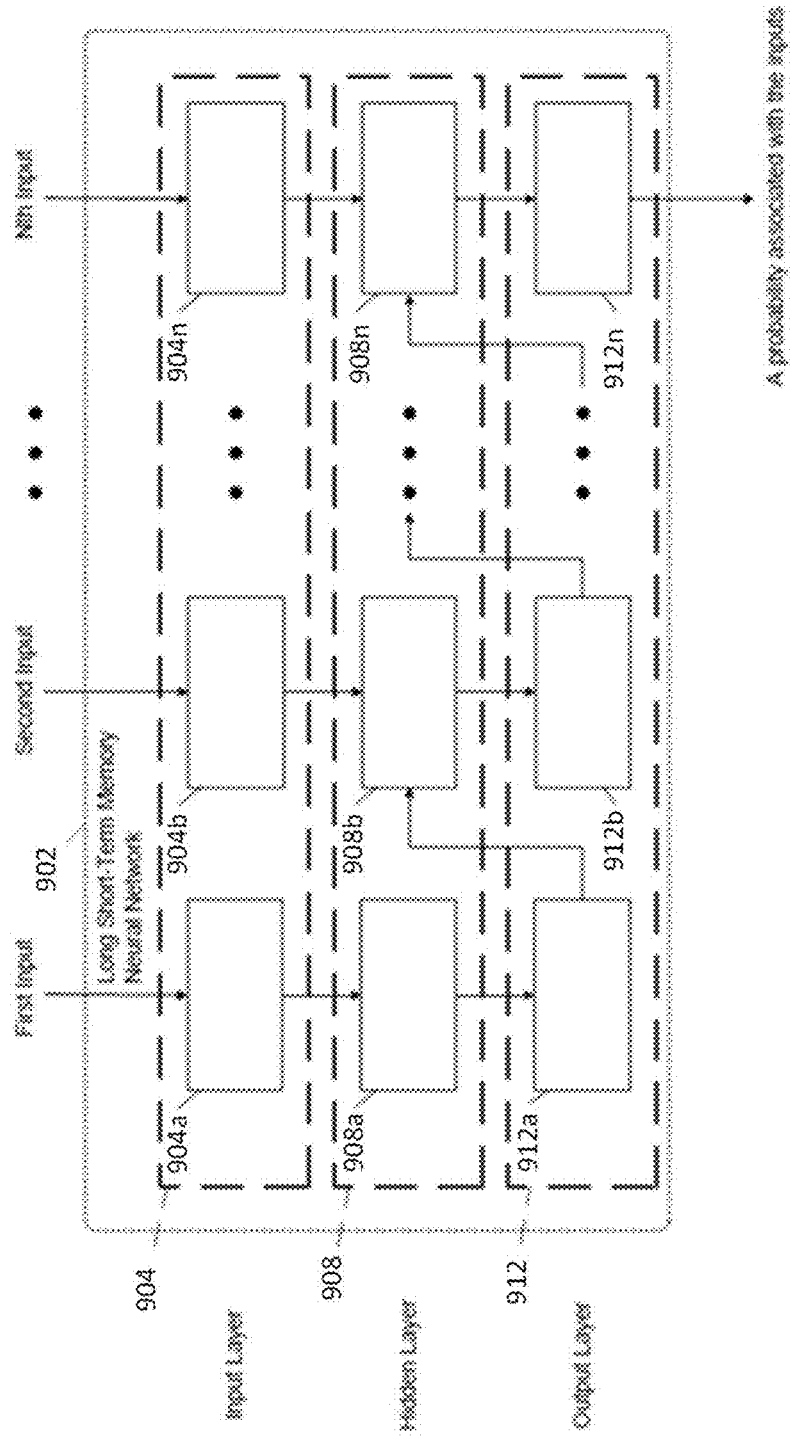
FIG. 9 is a functional block diagram of an example neural network that can be used for the inference engine or other functions (e.g., engines) as described herein to produce a predictive model.

FIG. 9 is a functional block diagram of an example neural network 902 that can be used for the inference engine or other functions (e.g., engines) as described herein to produce a predictive model. The predictive model can identify a need to perform a re-reading based on a class of mobile health monitoring device 112. In an example, the neural network 902 can be a LSTM neural network. In an example, the neural network 902 can be a recurrent neural networks (RNN). The example neural network 902 may be used to implement the machine learning as described herein, and various implementations may use other types of machine learning networks. The neural network 902 includes an input layer 904, a hidden layer 908, and an output layer 912. The input layer 904 includes inputs 904a, 904b . . . 904n. The hidden layer 908 includes neurons 908a, 908b . . . 908n. The output layer 912 includes outputs 912a, 912b . . . 912n.

Each neuron of the hidden layer 908 receives an input from the input layer 904 and outputs a value to the corresponding output in the output layer 912. For example, the neuron 908a receives an input from the input 904a and outputs a value to the output 912a. Each neuron, other than the neuron 908a, also receives an output of a previous neuron as an input. For example, the neuron 908b receives inputs from the input 904b and the output 912a. In this way the output of each neuron is fed forward to the next neuron in the hidden layer 908. The last output 912n in the output layer 912 outputs a probability associated with the inputs 904a-904n. Although the input layer 904, the hidden layer 908, and the output layer 912 are depicted as each including three elements, each layer may contain any number of elements. Neurons can include one or more adjustable parameters, weights, rules, criteria, or the like.

In various implementations, each layer of the neural network 902 must include the same number of elements as each of the other layers of the neural network 902. For example, training mobile device class features may be processed to create the inputs 904a-904n. The neural network 902 may implement a model to produce re-reading request prediction or selection for at least one of the mobile device class features. More specifically, the inputs 904a-904n can include mobile device class features (binary, vectors, factors or the like) stored in storage devices.

The mobile device class features can be provided to neurons 908a-908n for analysis and connections between the known facts. The neurons 908a-908n, upon finding connections, provides the potential connections as outputs to the output layer 912, which determines a need to perform a re-reading or to select an outreach event of a particular type from many types of outreach events.

The neural network 902 can perform any of the above calculations. The output of the neural network 902 can be used to trigger an outreach event including providing a notification. For example, the notification can be provided to a PBM, health plan manager, pharmacy, physician, caregiver, and/or a patient.

In some embodiments, a convolutional neural network may be implemented. Similar to neural networks, convolutional neural networks include an input layer, a hidden layer, and an output layer. However, in a convolutional neural network, the output layer includes one fewer output than the number of neurons in the hidden layer and each neuron is connected to each output. Additionally, each input in the input layer is connected to each neuron in the hidden layer. In other words, input 904a is connected to each of neurons 908a, 908b . . . 908n.

Analysis of Health Data Generation of Action Plans Examples

The aforementioned embodiments described various health monitoring processes to monitor health. For example, health monitoring information can be accurately and reliably obtained through various mechanisms (e.g., an automatically generated outreach event). The below embodiments further describe the analysis of the health monitoring information and the generation of action plans to mitigate health conditions identified based on the health monitoring information.

Patient health information can be difficult to track, monitor, and analyze. For example, a patient can have inaccurate blood pressure readings at a healthcare provider's office due to stresses of the environment (e.g., "white coat syndrome"). Furthermore, patients are typically at a healthcare provider's offices for a short period of time which limits the ability of healthcare providers to track certain health data over a longer period of time. Generating a health plan based on time-limited data can cause inaccuracies (e.g., misdiagnosis). Furthermore, retesting a patient at the health provider's office can cause significant delays due to scheduling difficulties, and can cause delays in appropriate treatments being administered. In some cases, the healthcare provider can receive and analyze remotely collected health data. Despite the remote collection of health data, significant challenges remain. For example, remotely collected data can lack data due to patient error (e.g., noncompliance). Moreover, the above process consumes significant time and resources.

Even when the health data is received, a healthcare provider can misdiagnose or administer a suboptimal treatment plan. For example, a healthcare provider has limited training and limited experience. Furthermore, the healthcare provider has a limited capacity to utilize different types of sensor data. Moreover, healthcare providers employ a subjective decision-making process resulting in misdiagnosis as well as suboptimal and/or delayed treatment plans. Thus, significant challenges exist with respect to health condition diagnosis and treatment.

The disclosed embodiments provide systems and methods to monitor patient health in real-time using mobile monitoring devices or equipment, such as Internet of Things (IoT) devices. The disclosed embodiments automatically receive health data (e.g., patient self-reported data such as surveys in different forms, patient associated inputs from health care professionals, etc.) about a patient from a patient device and/or patient databases, analyze the health data, generate an action plan and provide the action plan to the patient (or enact the action plan) substantially in real-time. Doing so reduces latency, reduces utilization of resources, and improves patient outcomes. For example, some embodiments implement a machine learning prediction model that is trained based on a large dataset to effectively identify health conditions, probabilities of health conditions occurring in the future, and action plans to mitigate current health conditions and/or the potential future health conditions. Thus, embodiments can leverage the enhanced abilities of the machine learning prediction model to effectively reduce resource consumption while enhancing patient outcomes.

In this way, the disclosed embodiments improve the overall process of providing medical care and specifically improve the efficiency at which health information is received and analyzed to generate action plans. As a result, latency and resource consumption is reduced. For example, embodiments herein can reduce the number of times a patient visits a healthcare provider.

Furthermore, embodiments herein can implement artificial intelligence to train on sizeable and comprehensive datasets to diagnose and generate action plans. Doing so enables several technical enhancements, including reducing or removing human subjectivity from decision making (i.e., diagnosis and treatment) enabling a consistent approach with superior outcomes. Moreover, embodiments herein can receive data from various heterogeneous sensors (e.g., temperature sensor, motion sensor, etc.) that would not be utilized by a typical healthcare provider. Furthermore, such embodiments can predictively model future outcomes based on health data to predict whether a health condition will occur in the future, and actively attempt to prevent the health condition from occurring.

Thus, embodiments herein result in several technical enhancements. By reducing or removing human subjectivity, health conditions are more accurately assessed. Based on the more accurate assessment, the health conditions can be addressed to quickly minimize patient impact, hospital resources (e.g., addressing a health condition earlier results in better outcomes with reduced consumption of hospital resources), while also enhancing patient experience. For example, once a health condition is identified in a patient, an action plan is automatically selected to mitigate the health condition and/or reduce the probability of the health condition occurring.

Moreover, yet another technical enhancement is faster speed and higher efficiency of the diagnosis and treatment, while also conserving computing resources by automatically, dynamically, and intelligently selecting efficient and effective health plans which are dynamically adjustable to enable better outcomes. As such, some examples enhance the technical areas of computerized health condition prediction and/or health condition identification, as well as action plan generation based on the health condition prediction and/or health condition identification. Yet another technical enhancement can include using a rigorous, computerized process to perform tasks (e.g., an efficient way to diagnose health conditions and generate health plans based on historical data associated with a plurality of patients and sensor data from a plurality of different sensors that measure various features such as environmental conditions) that were not previously able to be performed by humans in a practical or accurate manner. Some examples can further include referrals to a physician when a condition becomes either incalculable due to being out of a permissible range or other unknown factors, and/or the health condition expanding beyond a digital experience and into immediate health care.

In some examples, embodiments herein further encompass behavioral cases. For example, patient behaviors can be tracked and monitored as part of the health information/health data. Action plans to modify behaviors of a patient can be generated.

Furthermore, while some embodiments describe specific use cases, it should be understood that these are merely examples. It should be understood that embodiment are more expansive beyond behavioral. Embodiments can be applied to diagnosing health conditions and health treatments of any disease condition.

Figure 10A:
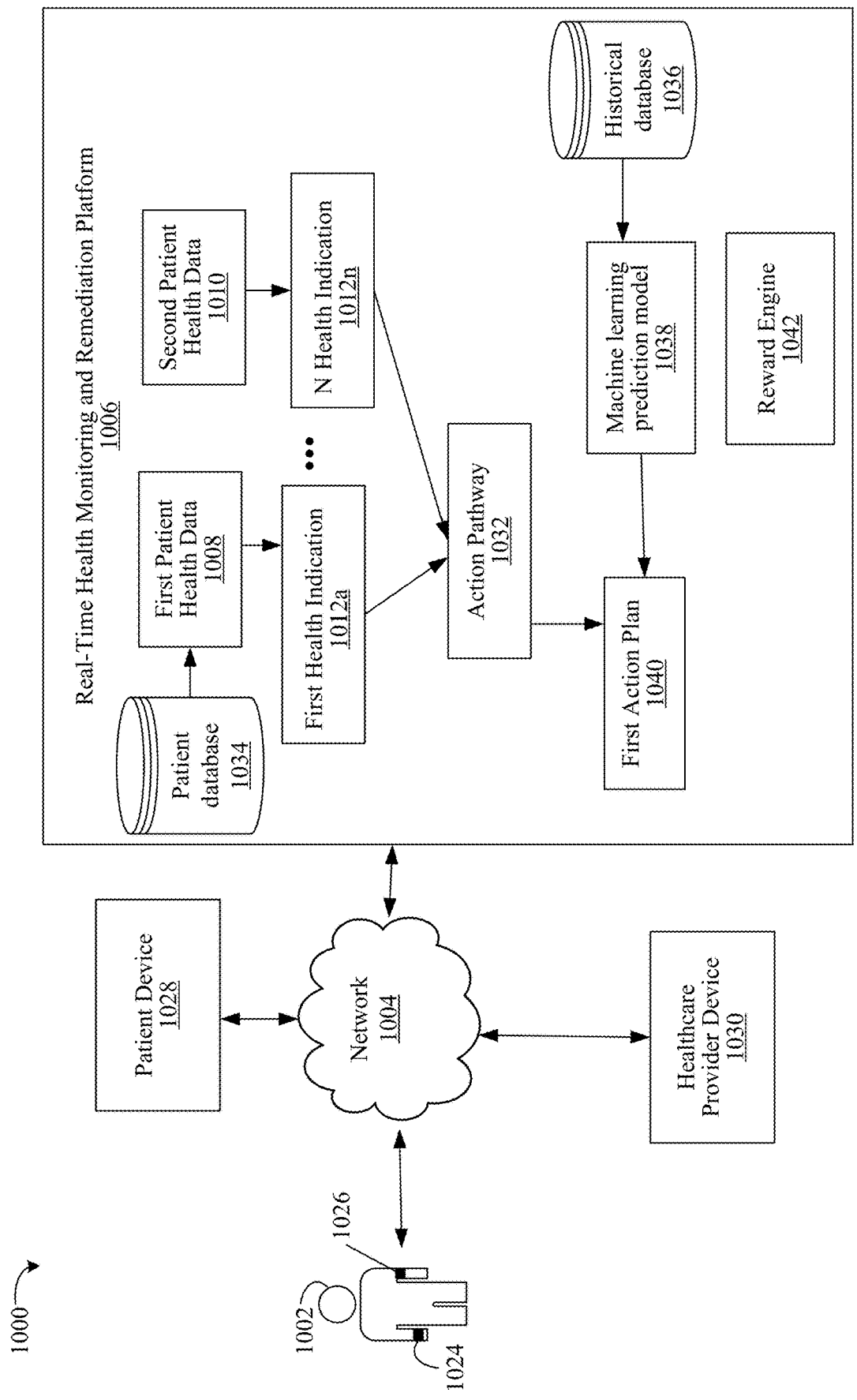
FIG. 10A is a diagram of an example of a health monitoring, identification, and treatment process according to an embodiment.

FIG. 10A illustrates a health monitoring, identification, and treatment process 1000. FIG. 10A can be readily incorporated into and/or operate with any of the embodiments described herein, for example the health monitoring system 100 (FIG. 1), database 152 (FIG. 2), outreach event selection system 156 (FIG. 3), user interfaces 400 (FIG. 4) and 500 (FIG. 5), process 600 (FIG. 6), software architecture 706 (FIG. 7), machine 800 (FIG. 8), and neural network 902 (FIG. 9).

A healthcare provider device 1030, a real-time health monitoring platform (RTHMRP) 1006, a blood pressure cuff 1026, smart watch 1024, and patient device 1028 are communicatively coupled over a network 1004 (e.g., Internet, telephony network, etc.). Some embodiments further monitor patient health based on patient self-reported data such as surveys in different forms, patient-associated inputs from health care professionals, etc. to modify behaviors of the patient 1002.

As illustrated, several health monitoring devices are attached to a patient 1002 (e.g., a user). For example, each of the blood pressure cuff 1026 and smart watch 1024 includes hardware and/or software configured to collect and/or measure a particular type of health monitoring information. It will be understood that while a blood pressure cuff 1026 and smart watch 1024 are specifically discussed in the below example, various other types of health monitoring devices can operate with the embodiments described herein. Various other types of health monitoring devices include, e.g., a smart scale, an exercise bracelet, glucometer, and/or an ECG device. In some examples, and as noted above, if a given group of monitoring information (e.g., blood pressure, heart rate, etc.) is determined as being unavailable to be provided by one or more of the blood pressure cuff 1026 or the smart watch 1024 (e.g., a first computing device), examples generate an outreach event to request the given group of monitoring information from the patient 1002.

The blood pressure cuff 1026 monitors a blood pressure and heart rate of the patient 1002, while the smart watch 1024 monitors a heart rate (e.g., resting heart rate, heart rate during walking, etc.) of the patient 1002, maximal oxygen consumption (i.e., VO2 max) of the patient 1002, fitness activity (e.g., number of steps, minutes of cardiovascular activity, etc.) of the patient 1002, sleep activity of the patient 1002, electrocardiogram activity of the patient 1002, menstrual cycles of the patient 1002, etc. The blood pressure cuff 1026 and smart watch 1024 can be connected to the network 1004 directly, or through patient device 1028 (e.g., a computing device such as a laptop, mobile device, palmtop computer, etc.) of the patient 1002. Various other types of health data can also be generated by other health monitoring devices. For example, other types of health data can include aerobic activity information, body mass index (BMI) information, sodium intake information, arrhythmia information, and/or glucose information. In some examples, the patient 1002 can manually input health data (e.g., sodium intake information) into the patient device 1028 for transmission to the RTHMRP 1006 and storage as patient data. In some examples, recorded information can be provided to the RTHMRP 1006 and stored as patient data, and includes a physician diagnosis or other health care professional collected data.

The patient device 1028 can include a mobile phone, desktop computer, laptop, portable digital assistants (PDAs), smart phones, a wearable device (e.g., a smart watch), tablets, ultrabooks, netbooks, laptops, multi-processor systems, microprocessor-based or programmable consumer electronics, game consoles, set-top boxes, or any other communication device that a patient can use to access the network 1004 or the RTHMRP 1006. The patient device 1028 can directly receive health data from the blood pressure cuff 1026 and the smart watch 1024, and transmit the same to the RTHMRP 1006.

In some examples, the health data from the patient device 1028, the blood pressure cuff 1026, and/or the smart watch 1024 can be transmitted over a secure connection to the RTHMRP 1006. After establishing the secure connection, the patient device 1028, the blood pressure cuff 1026, and/or the smart watch 1024 can be configured to exchange encrypted communications in real time with each other, the healthcare provider device 1030, and/or the RTHMRP 1006. In this way, a patient's health monitoring information remains securely stored on the patient's device 1028 and cannot be compromised. This ensures that the health monitoring information is privately maintained. In some cases, functionality of one or more of the blood pressure cuff 1026 and smart watch 1024 can be implemented by the patient device 1028. This can avoid the need to use a separate hardware device to collect a given type of health monitoring information.

The healthcare provider device 1030 can include the same or similar functionality as the blood pressure cuff 1026, the smart watch 1024, and the patient device 1028 to generate health data of the patient 1002. In some embodiments, the healthcare provider device 1030 can receive communications from and/or access the RTHMRP 1006, the blood pressure cuff 1026, the smart watch 1024, and/or the patient device 1028.

In some embodiments, the healthcare provider device 1030 is used by "internal" patients. Internal patients are personnel, such as physicians, clinicians, healthcare providers, health-related coaches, pharmacy benefit manager (PBM) operators, pharmacists, specialty pharmacy operators or pharmacists, or the like that are associated with or employed by an organization that provides the RTHMRP 1006. In some cases, the healthcare provider device 1030 is used by "external" patients. External patients are personnel, such as physicians, clinicians, and health-related coaches that are associated with or employed by a different (external) organization than that which provides the RTHMRP 1006. In some cases, the healthcare provider device 1030 transmits real-time data, such as messages, to the RTHMRP 1006 to provide health measurements and analysis of the patient 1002. For example, such health measurements and analysis can be collected and entered into the healthcare provider's Electronic Health Record platform (EHR) and sent through a vendor to the patient longitudinal patient record, and then consumed by the RTHMRP 1006 to be stored as patient data.

The RTHMRP 1006 can analyze the health data to identify trends and occurrences of health matters. To do so, the RTHMRP 1006 determines associations between health-related data and first-N health indications 1012*a*-1012*n*. The first-N health indications 1012*a*-1012*n* can be different types of health classifications such as normal blood pressure, elevated blood pressure, Stage 1 high blood pressure, Stage 2 high blood pressure, pre-diabetic, no diabetes, diabetic, high cholesterol, normal cholesterol, physical activity above a threshold, physical activity below a threshold, smoker, non-smoker, etc. Based on the associations, the RTHMRP 1006 can identify health conditions and recommend action plans to remedy the health conditions.

For example, the RTHMRP 1006 can receive second patient health data 1010 from the blood pressure cuff 1026 (e.g., the second patient health data 1010 is from the given group of monitoring information). The RTHMRP 1006 can analyze the second patient health data 1010 and identify a health measurement contained in the second patient health data 1010. The health measurement can be a blood pressure (e.g., blood pressure information) reading including diastolic reading of 88 and systolic measurements of 138 (138/88). It is worthwhile to note that while blood pressure is described herein as the health measurement, embodiments can operate similarly with any other type of health related measurement (e.g., heart rate information, cholesterol information, breathing information, etc.).

The RTHMRP 1006 associates the second patient health data 1010 with N health indication 1012*n* based on the health measurement of the second patient health data 1010. For example, the health measurement of 138/88 can be considered slightly elevated blood pressure (stage I hypertension). The N health indication 1012*n* can be an indication of slightly elevated blood pressure, and thus the second patient health data 1010 is associated with the N health indication 1012*n*.

In some examples, blood pressure can fluctuate significantly over a period of time based on sleep patterns, diet, stress, exercise, mood, etc. Thus, one elevated blood pressure can be an anomaly rather than indicative of a chronic condition. Therefore, the RTHMRP 1006 can provide a request (e.g., a re-read request as described above) to the patient device 1028 via an application on the patient device 1028 and/or the blood pressure cuff 1026 to obtain further blood pressure readings over a period of time. The RTHMRP 1006 can provide instructions to obtain the blood pressure readings at certain times of day, in response to certain conditions being detected and/or over periodically over a period of time. The application can be an extension of the RTHMRP 1006.

For example, and as noted above, stress can affect blood pressure readings. Thus, the RTHMRP 1006 can instruct the blood pressure cuff 1026 and/or the patient 1002 via the application to obtain a blood pressure reading when a patient's heart rate as measured by the smart watch 1024 is below a certain threshold and/or within a range of the resting heart rate as measured by smart watch 1024. For example, the RTHMRP 1006 can identify the heart rate from the smart watch 1024, and provide an instruction to the blood pressure cuff 1026 and/or the patient 1002 via the application to obtain a blood pressure reading when the heart rate is below the certain threshold and/or within the range of the resting heart rate. If the patient 1002 is not wearing the blood pressure cuff 1026, the patient 1002 can be instructed through the patient device 1028 and/or the patient 1002 via the application to put on the blood pressure cuff 1026, and then obtain the reading. In some embodiments, the blood pressure cuff 1026 can interact directly with the smart watch 1024 to determine when to obtain a blood pressure reading, for example based on an instruction from the smart watch 1024 and/or a heart rate indication from the smart watch 1024. Furthermore, several blood pressure readings can be obtained and provided to the RTHMRP 1006 as second patient health data 1010.

Thus, the RTHMRP 1006 can thus receive multiple health measurements (e.g., blood pressure readings) from the blood pressure cuff 1026, and store the multiple health measurements as part of the second patient health data 1010. The RTHMRP 1006 can then determine whether a certain number of the health measurements are associated with the N health indication 1012*n* (stage I hypertension) by being above a threshold. If so, the second patient health data 1010 is associated with the N health indication 1012*n* since many elevated blood pressure readings reliably indicate the persistence of stage I hypertension. Otherwise, if the number of health measurements is below the threshold, the RTHMRP 1006 determines that any elevated blood pressure readings are abnormalities rather than being indicative of a chronic health condition. In such a case, the second patient health data 1010 would not be associated with the N health indication 1012*n*, and would be associated with another health indication from the first-N health indications 1012*a*-1012*n* indicating that the patient 1002 has normal blood pressure.

Thus, the RTHMRP 1006 can verify whether the second patient health data 1010 is an abnormality based on whether several health measurements in the second patient health data 1010 (i.e., blood pressure readings) are within elevated boundaries. In this example, the RTHMRP 1006 determines that the health measurement(s) (i.e., blood pressure reading(s)) contained in the second patient health data 1010 is elevated, and therefore that the second patient health data 1010 is associated with the N health indication 1012*n*.

The RTHMRP 1006 can further select and extract first patient health data 1008 from a patient database 1034. The patient database 1034 can store numerous healthcare records from different patients. The RTHMRP 1006 can look-up the first patient health data 1008 based on identification information (e.g., a name, social security number, etc.) of the patient 1002. The first patient health data 1008 can include, e.g., medical records of the patient 1002, family history of the patient 1002, a geographic location of the patient 1002, self-reported data of the patient 1002, surveys in different forms answered by the patient 1002, inputs related to the patient 1002 that are collected from healthcare professionals, and demographic information of the patient 1002. The first patient health data 1008 can for example, further include a family history of cardiovascular illness, a geographic location where cardiovascular issues are prevalent, externally derived disease diagnoses that are derived for example by external engines to generate an indicator and the indicator is stored into the longitudinal patient record, and previous medical measurements taken at various settings and with various devices (e.g., provider's office, previous medical readings, etc.). It is worthwhile to note that the patient database 1034 can be encrypted to protect patient anonymity, and decrypted on a patient-by-patient basis and in response to a requesting user being authenticated.

The first patient health data 1008 is associated with the first health indication 1012a. For example, the first patient health data 1008 can include a health measurement (e.g., a number of family members with cardiovascular issues, previous readings taken with other devices, etc.). The first patient health data 1008 can be associated with the first health indication 1012a based on the health measurement of the first patient health data 1008, which indicates a presence of the first health indication 1012a. For example, the first health indication 1012a can be an indication of pre-disposition towards hypertension due to family genetics. In such a case, if the number of family members indicated in the first patient health data 1008 is above a threshold, the first patient health data 1008 is associated with the first health indication 1012a. Otherwise, the first patient health data 1008 can be associated with a different health indication from the first-N health indications 1012a-1012n indicating no genetic predisposition towards hypertension. In this example, the first patient health data 1008 indicates a predisposition towards hypertension, and thus is associated with the first health indication 1012a. In some embodiments, the first and second patient health data 1008, 1010 can be associated to a same health indication (e.g., hypertension) of the first health indication 1012a-N health indication 1012n depending on the nature of the first health indication 1012a-N health indication 1012n.

The RTHMRP 1006 can then identify an action pathway 1032 for the patient 1002. The action pathway 1032 can indicate a level of care that is needed for the patient 1002. For example, the action pathway 1032 is one of a stable pathway, an intervention pathway, and an escalation pathway, although other pathways can be included based on the specific nature of the health condition (e.g., behavioral condition). A stable pathway is selected when the first patient health data 1008 and the second patient health data 1010 indicates that the patient 1002 is stable and therefore only routine health checkups are needed. A stable pathway can be characterized by a blood pressure of less than 120/80, moderate aerobic activity of 150 minutes or more per week, a BMI of less than 25, daily sodium intake of less than 2300, hgb A1C of less than 5.6, low-density lipoprotein (LDL) of less than 100, high-density lipoprotein (HDL) of greater than 40 and being a non-smoker (e.g., readings that are within normal ranges).

The intervention pathway is selected when the first patient health data 1008 and the second patient health data 1010 indicate that the patient 1002 has emerging health conditions and/or has a health condition, but does not need immediate medical attention (e.g., the health condition is not exigent). The intervention pathway can be characterized by a blood pressure within the range of 120/80-159/99 on two different occasions, daily sodium intake of over 2300 mg over a week time, A1C between 5.6-8.9, LDL between greater than 100, HDL of less than 40, being a smoker or having a BMI of greater than 25. The intervention pathway can also be selected when multiple measurements indicate a health condition. For example, the intervention pathway can be selected if, as indicated by the first patient health data 1008 and second patient health data 1010, the weight of the patient 1002 has increased by two pounds in a 24 hour period or five pounds in one week, and/or the blood pressure is 143-170/80-100, and/or pulse 100-120, and/or shortness of breath at activity, and/or mild swelling, and/or no cough, and no chest pain and no trouble lying flat (e.g., readings that are slightly deviated from normal ranges).

In some examples, the intervention pathway can be selected if the first patient health data 1008 indicates a predisposition for a health condition, and the second patient health data 1010 indicates that health measurements are trending towards a health condition. For example, even if blood pressure readings in the second patient health data 1010 are slightly below 120/80, the intervention pathway can still be selected if the first patient health data 1008 indicates that the patient 1002 has a genetic predisposition towards high blood pressure. In some examples, the intervention pathway can be selected if current blood pressure readings (even if in normal range) in the second patient health data 1010 and historical blood pressure readings in the first patient health data 1008 indicate an overall trend upward towards pre-hypertension.

The escalation pathway is selected when the first patient health data 1008 and the second patient health data 1010 indicate that the patient 1002 has an exigent health condition that does require immediate medical attention. The escalation pathway can be characterized by having a blood pressure greater than 160/100 repeatedly for more than two days, arrhythmia of some type detected by an IoT device such as the smart watch 1024 or having an A1C greater than 9. The escalation pathway can be selected based on several factors as well. For example, the escalation pathway can be selected if, as indicated by the first patient health data 1008 and the second patient health data 1010, the weight of the patient 1002 has increased by three pounds in 24 hours, the blood pressure is over 170/100, shortness of breath at rest, moderate to severe leg swelling, persistent dry cough, chest pain, trouble sleeping, and/or cannot life flat with two or less pillows or limited activity. For example, the first patient health data 1008 can store historical weights of the patient 1002 while the second patient health data 1010 can store a current weight of the patient 1002. A comparison of the current weight to the historical weights can indicate whether the patient has weight change (e.g., greater than three pounds).

FIG. 10B illustrates a table 1044 that shows conditions that can cause the RTHMRP 1006 to select between the stable, intervention, and escalation pathways. In some examples, the characteristics to determine to apply the stable, intervention or escalation pathway changes based on whether the patient is in a diagnosed or pre-diagnosed state. For example, in a diagnosed state the stable pathway can be characterized by blood pressure of less than 130/80, pulse less than 100, no symptoms, activity level normal, sodium intake less than two grams. The intervention pathway can be characterized by a weight increasing by two pounds in 24 hour period or 5 pounds in one week, blood pressure of 143-170/80-100, pulse rate of 100-120, shortness of breath at activity, and/or mild leg swelling with no cough, no chest pain and no trouble lying flat.

Thus, the RTHMRP 1006 analyzes the first health indication 1012a and the N health indication 1012n to determine whether the first health indication 1012a and the N health indication 1012n indicate a same health condition (e.g., high blood pressure) and/or a specific behavior, and if so, whether the health condition is exigent. Based on as much, the RTHMRP 1006 sets the action pathway 1032 as the stable pathway, the intervention pathway, or the escalation pathway. In this example, the first health indication 1012a indicates Stage I hypertension and the N health indication 1012n indicates a genetic predisposition to hypertension. Based on as much, the action pathway 1032 is set to the intervention pathway. In some cases, a state I hypertension diagnosis cannot trigger an intervention pathway if the patient 1002 did not have genetic predisposition to hypertension.

The RTHMRP 1006 can then generate a first action plan 1040 (e.g., can be a predefined plan that follows clinical standards or is generated on the fly by artificial intelligence) based on the action pathway 1032, and based on a level of urgency indicated in the action pathway 1032. For example, if the action pathway 1032 is the stable pathway, a low level of urgency is indicated and the first action plan 1040 can include periodic health measurements of the patient 1002, a notification of any observed health trends (e.g., increasing blood pressure but not yet in a hypertension group), health measurements, and a reward to the patient 1002. When the action pathway 1032 is the intervention pathway, a medium level of urgency is indicated and the first action plan 1040 includes one or more of a notification of a health condition or a potential health condition that is developing, health-related training, a live and/or online medical consultation, a healthcare provider visit, requests to continue to monitor health and provide updated health measurements, etc. In some examples, the first action plan 1040 can be immediate temporal next steps for the patient 1002 followed by a wait state for more information or for a timed event. When the action pathway 1032 is the escalation pathway, a high level of urgency is indicated and the first action plan 1040 includes an attempt to urgently connect the patient to a healthcare provider through the healthcare provider device 1030, an urgent notification to one or more of a healthcare provider via the healthcare provider device 1030 and the patient 1002 via the patient device 1028 that the patient 1002 is in a diseased state associated with the first and N health indications 1012a, 1012n, or an urgent deployment of emergency personnel to the patient 1002.

In this example, the action pathway 1032 is the intervention pathway. Therefore, the first action plan 1040 includes one or more of a notification of a health condition or a potential health condition that is developing, health-related training, a live and/or online medical consultation, a healthcare provider visit, requests to continue to monitor health and provide updated health measurements, etc. The exact nature of the first action plan 1040 can be set based on the particular health condition associated with the first health indication 1012a and N health indication 1012n. For example, when the health condition is hypertension, the healthcare providers can have an in-depth experience with hypertension, and the patient 1002 can be provided with guidance to lower blood pressure (e.g., reduce sodium, exercise, sleep regularly, etc.). Thus, the first action plan 1040 can be determined based on the health condition associated with the first health indication 1012a and N health indication 1012n.

The RTHMRP 1006 further includes a machine learning prediction model 1038. The machine learning prediction model 1038 can be trained based on historical data from the historical database 1036 associated with a plurality of patients. The historical database 1036 can include a plurality of action plans that are stored in association with the outcome data (e.g., whether each of the action plans resulted in prevention or reduction of a health condition). The machine learning prediction model 1038 is trained to predict whether an action plan in the historical data is associated with a successful outcome based on outcome data of the historical data. The machine learning prediction model 1038 can generate the first action plan 1040.

In some examples, the machine learning prediction model 1038 generates the first action plan 1040 prior to analysis of the first and second patient health data 1008, 1010. The first action plan 1040 is selected in response to the action pathway 1032 and the health condition associated with the first and N health indications 1012a, 1012n. In such embodiments, the machine learning prediction model 1038 generates a plurality of action plans. In other embodiments, the first action plan 1040 can be generated on the fly and based on specific health factors (e.g., the condition, age, demographic, geography, comorbidities, etc.) associated with the patient 1002 and as identified from the first patient health data 1008. In some examples, the machine learning prediction model 1038 does not generate the first action plan 1040, and rather the RTHMRP 1006 determines the first action plan 1040 based on predefined treatment pathways that may have been derived from machine learning type analytics.

In some examples, the machine learning prediction model 1038 can associate the first health indication 1012a to the first patient health data 1008 and the second patient health data 1010 to the N health indication 1012n, generate the action pathway 1032 and the first action plan 1040. For example, the machine learning prediction model 1038 is trained based on historical data from the historical database 1036, where the historical data is associated with a plurality of patients. The machine learning prediction model 1038 is trained based on whether health measurements (e.g., patient data) in the historical data is associated with health indications in the historical database 1036. The machine learning prediction model 1038 therefore can determine whether health measurements are associated with a health indication during inference. In some examples, the machine learning prediction model 1038 includes one or more neural networks.

The RTHMRP 1006 can gather the historical data over a period of time, and store the historical data into the historical database 1036. For example, the RTHMRP 1006 can track interactions, action pathways, and outcomes of other patients and store as much in the historical database 1036. In some embodiments, the historical database 1036 can be a blockchain storage that is encrypted and where the data is stripped of personal identifying information to preserve patient anonymity and enhance security.

The RTHMRP 1006 can generate an outreach event to provide the first action plan 1040 and other relevant information to one or more of the patient device 1028 and/or the healthcare provider device 1030. The patient device 1028 can display a graphical patient interface that notifies the patient 1002 of the health condition and the first action plan 1040. In some examples, the patient device 1028 can implement aspects of the first action plan 1040 such as scheduling a live and/or online consultation with a health professional and periodically reminding the patient 1002 to track and maintain a low sodium level, asking for inputs verifying that the patient 1002 is complying with the first action plan 1040, etc.

In some examples, the RTHMRP 1006 tracks whether the patient 1002 is complying with the first action plan 1040. For example, the patient 1002 can provide inputs (e.g., sodium counts, estimation of aerobic activity, etc.) into the patient device 1028 to signal compliance with the first action plan 1040. The patient device 1028 provides the inputs to the RTHMRP 1006.

The RTHMRP 1006 also includes a rewards engine 1042. The rewards engine 1042 can generate rewards based on compliance of the patient 1002 with the first action plan 1040. For example, the first action plan 1040 can include a request for periodic blood pressure readings at certain times. If the patient 1002 diligently monitors blood pressure of the patient 1002 with the blood pressure cuff 1026 and provides the pressure readings to the RTHMRP 1006 at the certain times, the rewards engine 1042 can determine that the patient is complying with the first action plan 1040 and therefore generate/provision a reward (e.g., monetary compensation, congratulations message, merchandise, etc.) for the patient 1002. In contrast, if the patient 1002 does not provide the pressure readings to the RTHMRP 1006 at the certain times, then the rewards engine 1042 can determine that the patient 1002 is not complying with the first action plan 1040 and generate a penalty based on the non-compliance of the patient 1002.

In some embodiments as explained further below, the RTHMRP 1006 can adjust or replace the first action plan 1040 in response to an identification that the patient 1002 is not complying with the first action plan 1040. For example, the machine learning prediction model 1038 can include a generative artificial intelligence model that generates new action plans based on actions and/or an analysis of the patient 1002. For example, data of the patient 1002 can be retrieved from the patient database 1034 and provided to the generative artificial intelligence model as inputs. Furthermore, the noncompliance of the patient 1002 can be provided to the generative artificial intelligence model as inputs. The generative artificial intelligence model can generate a new plan that can better address the patient's 1002 needs while also being adjusted to the patient's 1002 personality. For example, the data of the patient 1002 can be indicative of personality traits and habits of the patient 1002 (e.g., enjoys exercising, dislikes jogging, enjoys biking, etc.). The generative artificial intelligence model can adjust plans based on the identified personality traits and habits to provide a focused and engaging plan tailored to the patient 1002. Doing so results in better compliance, resulting in reduced resources to treat the patient 1002 and better outcomes.

In some examples, the RTHMRP 1006 can also include a chat interface that is available to the patient 1002. For example, the chat interface can be presented on a graphical user interface of the patient device 1028. The chat interface can operate with a generative artificial intelligence model operating on the RTHMRP 1006. The generative artificial intelligence model can provide instructions, guidance, answers (e.g., doctor recommendations, exercise advice, etc.) to the patient 1002 in an interactive format.

In some examples, activity information of the patient 1002 can be entered manually and/or tracked automatically by the smart watch 1024. The activity information can be stored and accumulated (e.g., track activity over a week) in the patient database 1034. The RTHMRP 1006 can identify the activity of the patient 1002 based on the activity information stored in the patient database 1034. The RTHMRP 1006 can determine whether the activity corresponds to an expected action associated with the first action plan 1040. The RTHMRP 1006 can determine whether the patient 1002 is following the first action plan 1040 based on whether the activity corresponds to the expected action. If the patient 1002 is following the first action plan 1040, the RTHMRP 1006 can maintain the first action plan 1040, generate a reward, and provide the reward to the patient 1002. If the patient 1002 is not in compliance with the first action plan 1040, the RTHMRP 1006 can generate a penalty for the patient 1002, adjust the first action plan 1040 to generate a second action plan, and transmit a command to the patient device 1028 to implement the second action plan.

Thus, the aforementioned embodiments generate a first action plan 1040 based on granular data retrieval and analysis. The first action plan 1040 can be customized based on the specific characteristics of the patient 1002. Moreover, embodiments can execute in real-time to reduce latency to diagnose and treat the patient 1002. Furthermore, embodiments can reduce the level of resources needed to effectively diagnose and treat the patient 1002.

Figure 11:
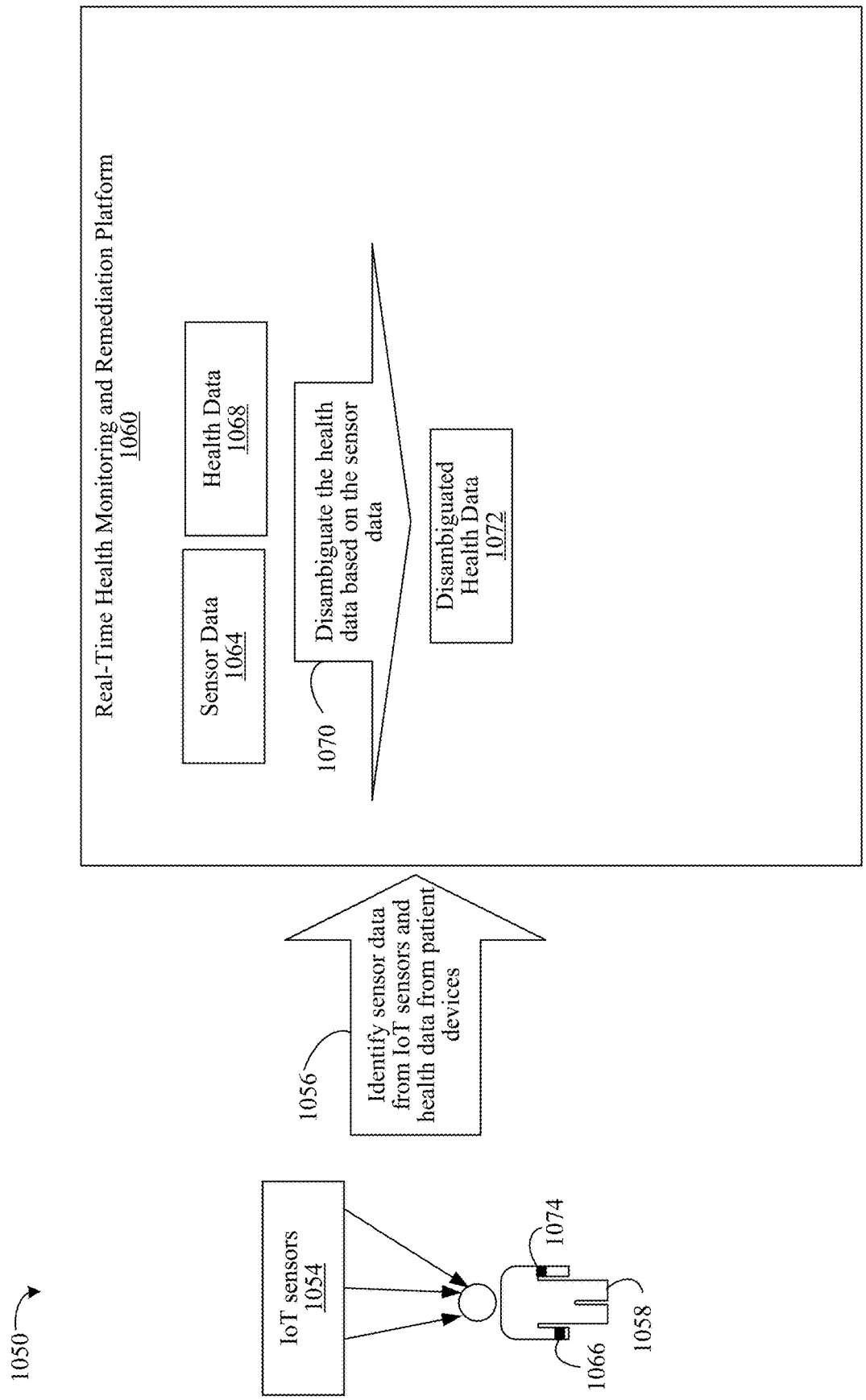
FIG. 11 is a diagram of an example of a noise reduction process according to an embodiment.

Turning now to FIG. 11, a noise reduction process 1050 is illustrated. The noise reduction process 1050 can be implemented in conjunction with any of the embodiments described herein, including the health monitoring system 100 (FIG. 1), database 152 (FIG. 2), outreach event selection system 156 (FIG. 3), user interfaces 400 (FIG. 4) and 500 (FIG. 5), process 600 (FIG. 6), software architecture 706 (FIG. 7), machine 800 (FIG. 8), neural network 902 (FIG. 9) and/or the health monitoring, identification and treatment process 1000 (FIGS. 10A and 10B).

In particular, a patient 1058 wears a plurality of devices (e.g., a blood pressure cuff, smart watch, fitness tracker, etc.) including a blood pressure cuff 1074 and a smart watch 1066 to measure health characteristics of the patient 1058. As noted above, certain factors can interfere with retrieving accurate measurements (e.g., time of day, stress level, environmental conditions such as heat, cold, etc.). Internet-of-things (IoT) sensors 1054 generate sensor readings (e.g., motion sensor, temperature readings, environmental conditions, audio sensor, proximity sensors, infrared sensor, touch sensor, color sensor, humidity sensor, etc.) associated with the patient 1058 to weight obtained health measurements of the patient 1058 and reduce noisy (inaccurate) measurements. For example, the noise reduction process 1050 identifies sensor data 1064 from the IoT sensors 1054 and health data 1068 from the patient devices 1056. A RTHMRP 1060 receives and stores the health data 1068 and the sensor data 1064.

The RTHMRP 1060 disambiguates the health data 1068 (e.g., blood pressure readings pulse rate, etc.) based on the sensor data 1064, 1070. For example, suppose that the health data 1068 is a blood pressure measurement that is in the hypertension group. Further suppose the sensor data 1064 indicates that the patient 1058 coughed as the blood pressure measurement was taken by the blood pressure cuff 1074. The RTHMRP 1060 can reduce the weight of the blood pressure measurement (e.g., set weight to a low value or 0) since the cough could cause the blood pressure to temporarily spike causing an unusually high blood pressure measurement. The disambiguated health data 1072 is the weighted blood pressure measurement in this example.

In another example, suppose that the smart watch 1066 detects a high pulse rate and provides as much as part of the health data 1068. Further suppose that the sensor data 1064 indicates that the patient 1058 was exercising when the high pulse rate was measured. The RTHMRP 1060 can reduce the weight of the high pulse rate (e.g., set weight to a low value or 0) since the high pulse rate is caused by exercise causing a temporary pule rate. The disambiguated health data 1072 is the weighted pulse rate in this example.

While not illustrated, the RTHMRP 1060 can discard the disambiguated health data 1072 altogether if the weight is below a threshold. In some examples, if the disambiguated health data 1072 is not discarded, the RTHMRP 1060 can associate the disambiguated health data 1072 with a health indication, generate an action pathway and generate an action plan as described with respect to the RTHMRP 1006 of FIG. 10A. It is worthwhile to note that the RTHMRP 1006 (FIG. 1) can readily execute any of the functions described with respect to the RTHMRP 1060 and in conjunction with the operations of the RTHMRP 1006.

Figure 12:
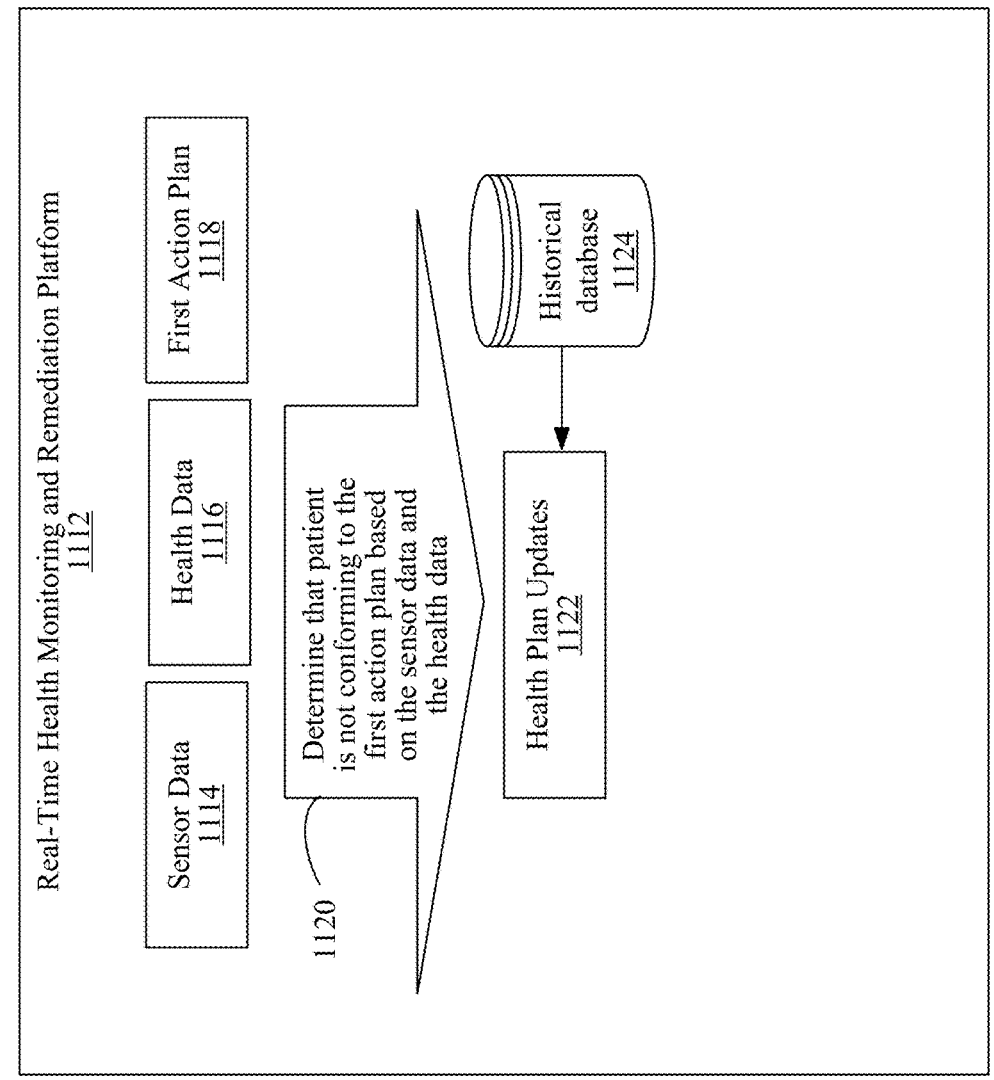
FIG. 12 is a diagram of an example of a health plan compliance process according to an embodiment.
Figure 12:
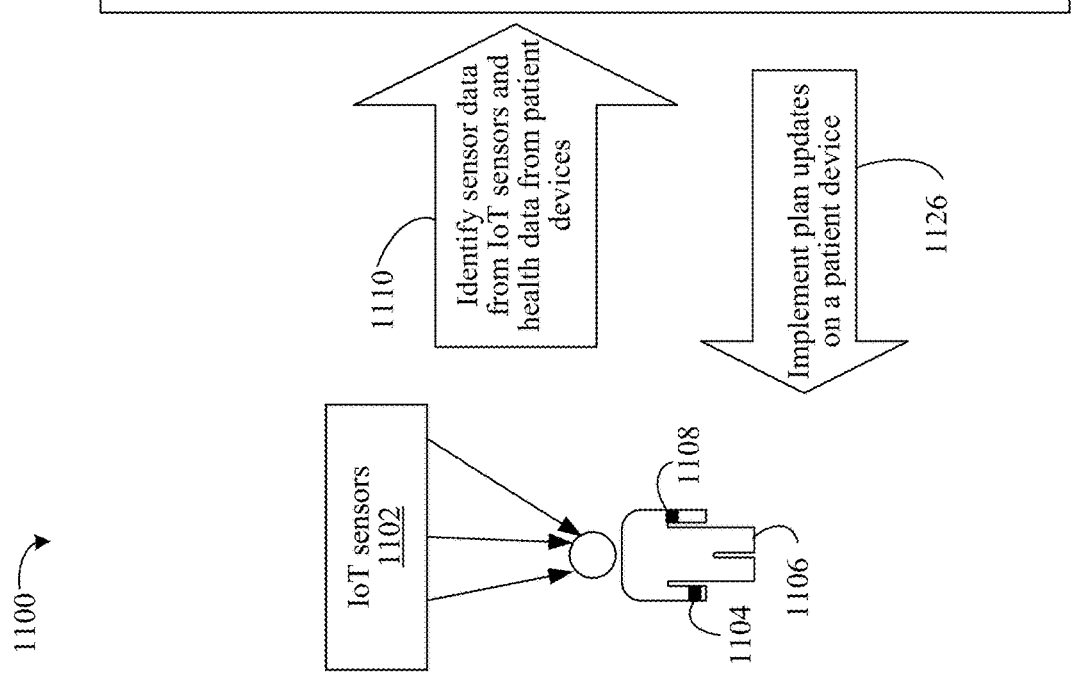

FIG. 12 illustrates a health plan compliance process 1100. The health plan compliance process 1100 can be implemented in conjunction with any of the embodiments described herein, including the health monitoring system 100 (FIG. 1), database 152 (FIG. 2), outreach event selection system 156 (FIG. 3), user interfaces 400 (FIG. 4) and 500 (FIG. 5), process 600 (FIG. 6), software architecture 706 (FIG. 7), machine 800 (FIG. 8), neural network 902 (FIG. 9), the health monitoring, identification and treatment process 1000 (FIGS. 10A and 10B), and/or noise reduction process 1050 (FIG. 11).

A RTHMRP 1112 is illustrated. The RTHMRP 1112 previously determined that a first action plan 1118 should be followed by patient 1106. The RTHMRP 1112 periodically determines if the patient 1106 is in compliance with the first action plan 1118.

For example, the patient 1106 is wearing a plurality of wearable patient devices 1104, 1108 that measure health data 1116 of the patient 1106. IoT sensors 1102 can also sense conditions related to the patient such as movement of the patient 1106, environment of the patient 1106, temperature of the patient 1106, etc. The process 1100 identifies sensor data 1114 from the IoT sensors 1102 and health data 1116 from the patient devices 1104, 1110.

The RTHMRP 1112 determines whether the patient 1106 is conforming to the first action plan 1118 based on the sensor data 1114 and the health data 1116. For example, if the first action plan 1118 indicates that the patient 1106 is to exercise for 150 minutes per week, the RTHMRP 1112 can verify that the patient 1106 is indeed meeting the mandated exercise time. That is, exercise amounts can be recorded by IoT sensors 1102 (e.g., motion detectors to detect exercise related movements) as the sensor data 1114 and/or the patient devices 1104, 1108 (e.g., smartwatch that records when heart rate reaches exercise related levels, and/or exercise related movements) as health data 1116. In some examples, other patient devices (e.g., computing devices) can also provide data indicating whether the patient is in compliance with the first action plan 1118.

The RTHMRP 1112 identifies if the patient 1106 is in compliance with the first action plan 1118. In this example, the RTHMRP 1112 determines that the patient 1106 is not conforming to the first action plan 1118 based on the sensor data 1114 and the health data 1116, 1120. In response to the patient 1106 not conforming to the first action plan 1118, the RTHMRP 1112 generates health plan updates 1122 to cause greater compliance in the patient 1106. For example, the RTHMRP 1112 can generate a first metric for the first action plan 1118 based on whether the patient 1106 is in compliance with the first action plan 1118. The first metric is a probability that the patient 1106 will comply with the first action plan 1118. The probability can be determined based on the user compliance/non-compliance with the first action plan 1118.

The RTHMRP 1112 can generate a second metric for a second action plan, embodied as the health plan updates 1122, based on historical data retrieved from a historical database 1124. The historical data is associated with a plurality of patients. For example, the RTHMRP 1112 can detect whether different action plans were effective for treating an underlying health condition of the patient 1106. The RTHMRP 1112 can select the action plan from the different action plans, excluding the first action plan 1118, with the highest probability of compliance for the patient 1106. The highest probability can be the second metric.

The RTHMRP 1112 can cease implementation of the first action plan 1118 and implement the second action plan based on a comparison of the first metric and the second metric. That is, the probability of the second metric is greater than the probability of the first metric, and thus the first action plan 1118 is replaced with the second action plan. The second action plan is stored as the health plan updates 1122. The process 1100 then implements plan updates (e.g., notify the patient of the second action plan) on a patient device 1126.

Figure 13:
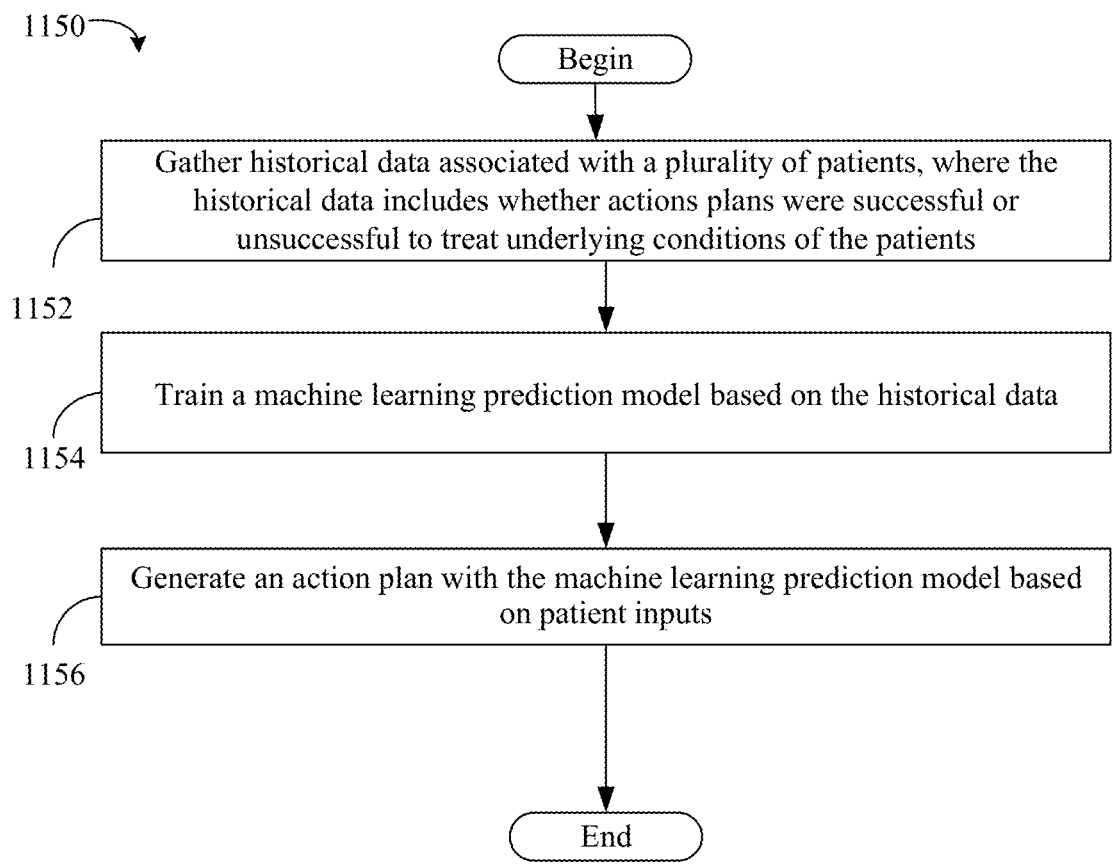
FIG. 13 is a flowchart of an example of a method of generating an action plan according to an embodiment.

FIG. 13 shows a method 1150 of generating an action plan. The method 1150 can generally be implemented in conjunction with any of the embodiments described herein, for example the health monitoring system 100 (FIG. 1), database 152 (FIG. 2), outreach event selection system 156 (FIG. 3), user interfaces 400 (FIG. 4) and 500 (FIG. 5), process 600 (FIG. 6), software architecture 706 (FIG. 7), machine 800 (FIG. 8), and neural network 902 (FIG. 9), the health monitoring, identification and treatment process 1000 (FIGS. 10A and 10B), the health monitoring, identification and treatment process 1000 (FIG. noise reduction process 1050 (FIG. 11), and/or health plan compliance process 1100 (FIG. 12). In an embodiment, the method 1150 is implemented in logic instructions (e.g., software), configurable logic, fixed-functionality hardware logic, computer readable instructions stored on at least one non-transitory computer readable storage medium that are executable to implement method 1150, circuitry, etc., or any combination thereof.

Illustrated processing block 1152 gathers historical data associated with a plurality of users, where the historical data includes whether actions plans were successful or unsuccessful to treat underlying conditions of the patients. Illustrated processing block 1154 trains a machine learning prediction model based on the historical data. For example, if machine learning prediction model is a neural network, processing block 1154 can include generating a loss based on the historical data and updating parameters of the neural network based on the loss. Illustrated processing block 1156 generates an action plan with the machine learning prediction model based on patient inputs. For example, the patient inputs can include sensor data related to the patient, health related readings of the patient, patient data (e.g., family history, previous readings, etc.) of the patient, which are then processed by the neural network to select an appropriate action plan.

Figure 14:
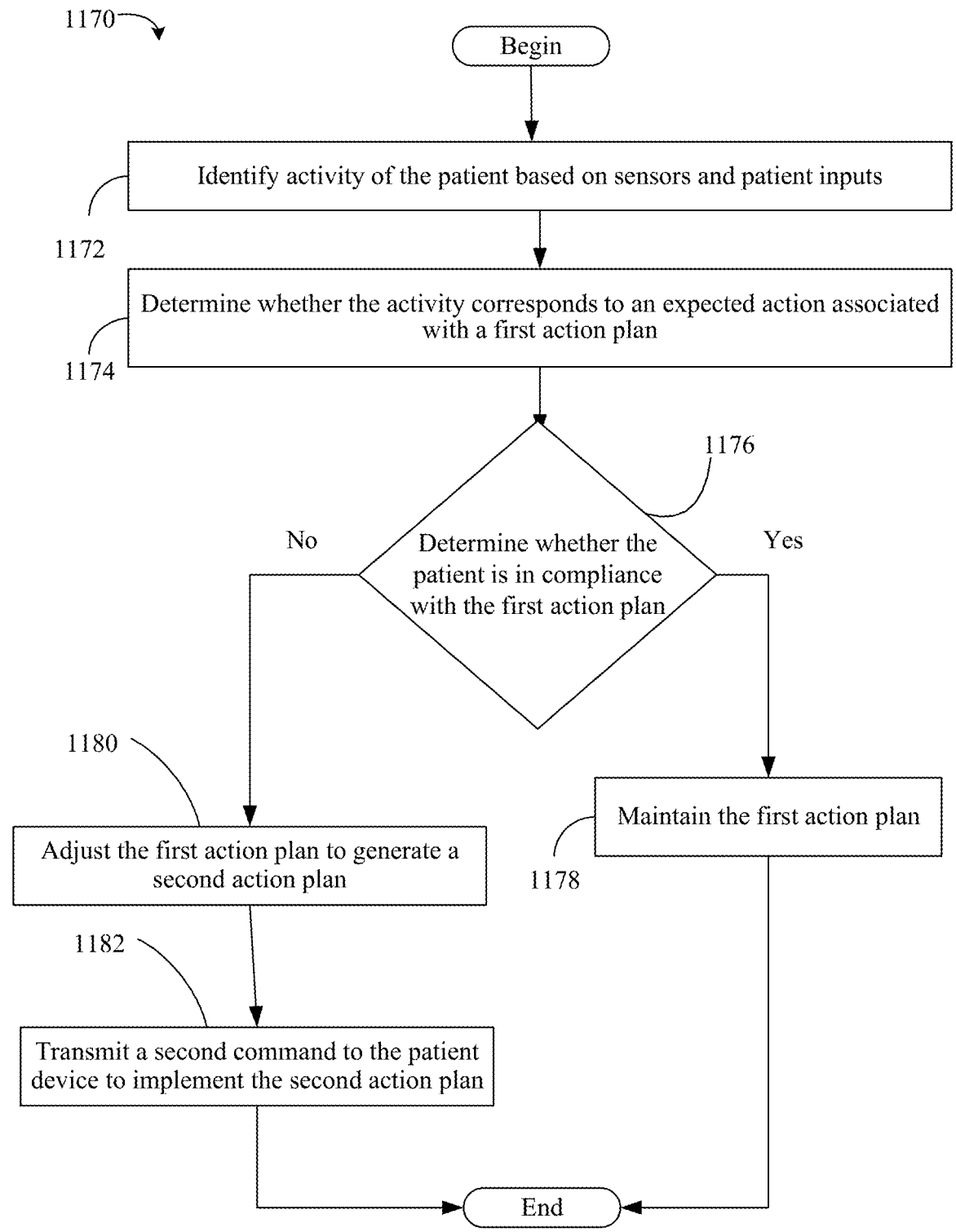
FIG. 14 is a flowchart of an example of a method of improving compliance with an action plan according to an embodiment.

FIG. 14 shows a method 1170 of improving compliance with an action plan. The method 1170 can generally be implemented in conjunction with any of the embodiments described herein, for example the health monitoring system 100 (FIG. 1), database 152 (FIG. 2), outreach event selection system 156 (FIG. 3), user interfaces 400 (FIG. 4) and 500 (FIG. 5), process 600 (FIG. 6), software architecture 706 (FIG. 7), machine 800 (FIG. 8), neural network 902 (FIG. 9), the health monitoring, identification and treatment process 1000 (FIGS. 10A and 10B), noise reduction process 1050 (FIG. 11), health plan compliance process 1100 (FIG. 12) and/or method 1150 (FIG. 13). In an embodiment, the method 1170 is implemented in logic instructions (e.g., software), configurable logic, fixed-functionality hardware logic, computer readable instructions stored on at least one non-transitory computer readable storage medium that are executable to implement method 1170, circuitry, etc., or any combination thereof.

Illustrated processing block 1172 identifies activity of the patient based on sensors and patient inputs (e.g., manual inputs by the patient into a computing device). Illustrated processing block 1174 determines whether the activity corresponds to an expected action associated with a first action plan (e.g., executes an action listed in the first action plan). Illustrated processing block 1176 determines whether the patient is in compliance with the first action plan, for example based on whether the activity corresponds to the expected action. If so, illustrated processing block 1178 maintains the first action plan. Otherwise, illustrated processing block 1180 adjusts the first action plan to generate a second action plan. Processing block 1180 can include adjusting features of the first action plan, such as suggested exercise types, duration, food suggestions etc. Illustrated processing block 1182 transmits a second command to the patient device to implement the second action plan.

Figure 15:
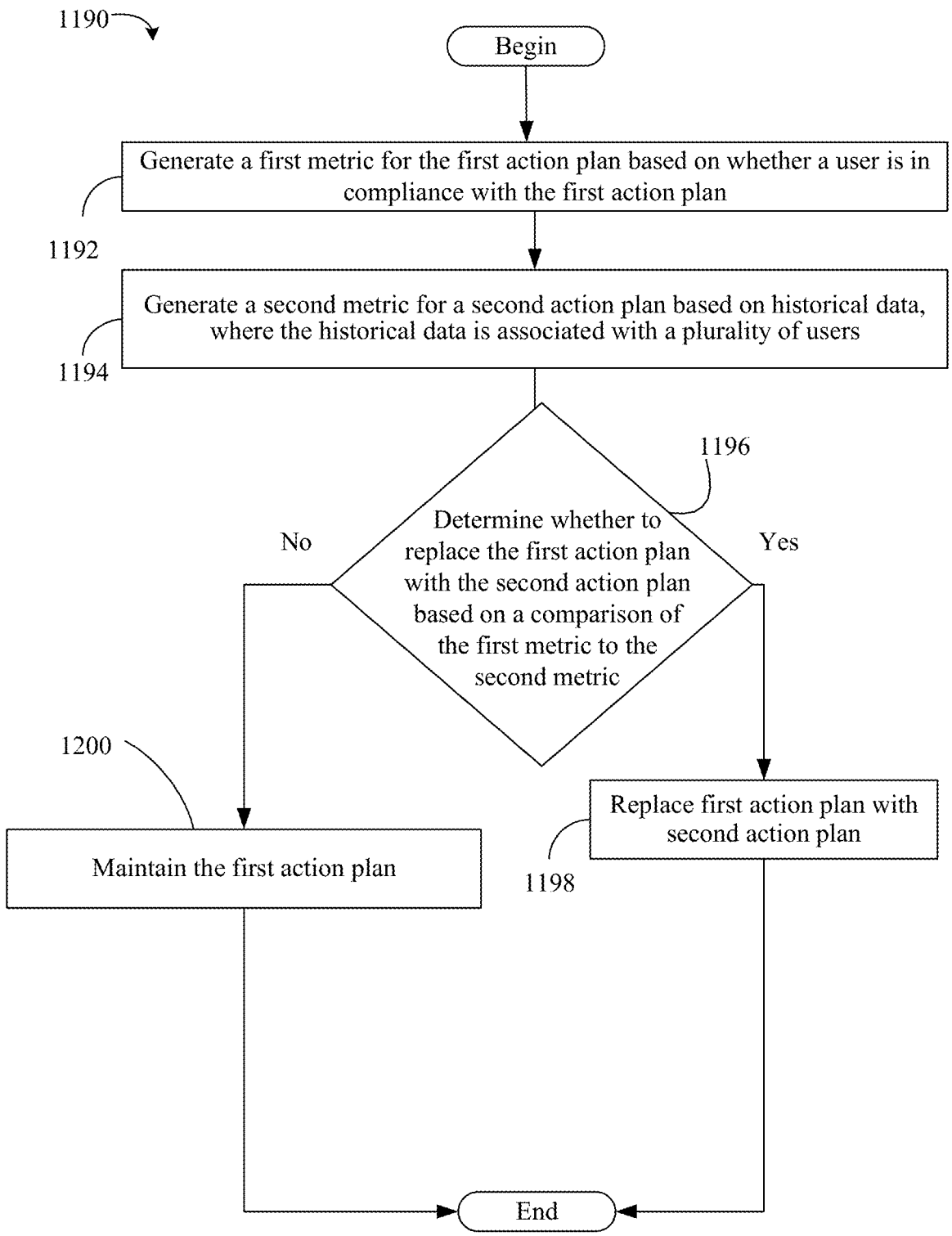
FIG. 15 is a flowchart of an example of a method of switching action plans according to an embodiment.

FIG. 15 shows a method 1190 of switching action plans. The method 1190 can generally be implemented in conjunction with any of the embodiments described herein, for example the health monitoring system 100 (FIG. 1), database 152 (FIG. 2), outreach event selection system 156 (FIG. 3), user interfaces 400 (FIG. 4) and 500 (FIG. 5), process 600 (FIG. 6), software architecture 706 (FIG. 7), machine 800 (FIG. 8), and neural network 902 (FIG. 9) and the health monitoring, identification and treatment process 1000 (FIGS. 10A and 10B), noise reduction process 1050 (FIG. 11), health plan compliance process 1100 (FIG. 12), method 1150 (FIG. 13) and/or method 1170 (FIG. 14). In an embodiment, the method 1190 is implemented in logic instructions (e.g., software), configurable logic, fixed-functionality hardware logic, computer readable instructions stored on at least one non-transitory computer readable storage medium that are executable to implement method 1190, circuitry, etc., or any combination thereof.

Illustrated processing block 1192 generates a first metric for a first action plan based on whether a user is in compliance with the first action plan. Illustrated processing block 1194 generates a second metric for a second action plan based on historical data, where the historical data is associated with a plurality of users. Illustrated processing block 1196 determines whether to replace the first action plan with the second action plan based on a comparison of the first metric (e.g., a probability of compliance with the first action plan based on whether user actions are part of the first action plan) to the second metric (e.g., a probability of compliance with the second action plan determined based on the historical data). If it is determined that the first action plan is to be replaced (e.g., second metric is greater than first metric), illustrated processing block 1198 replaces the first action plan with the second action plan. If it is determined that the first action plan (e.g., first metric is equal to or greater than second metric) is to be maintained, then illustrated processing block 1200 maintains the first action plan.

Figure 16:
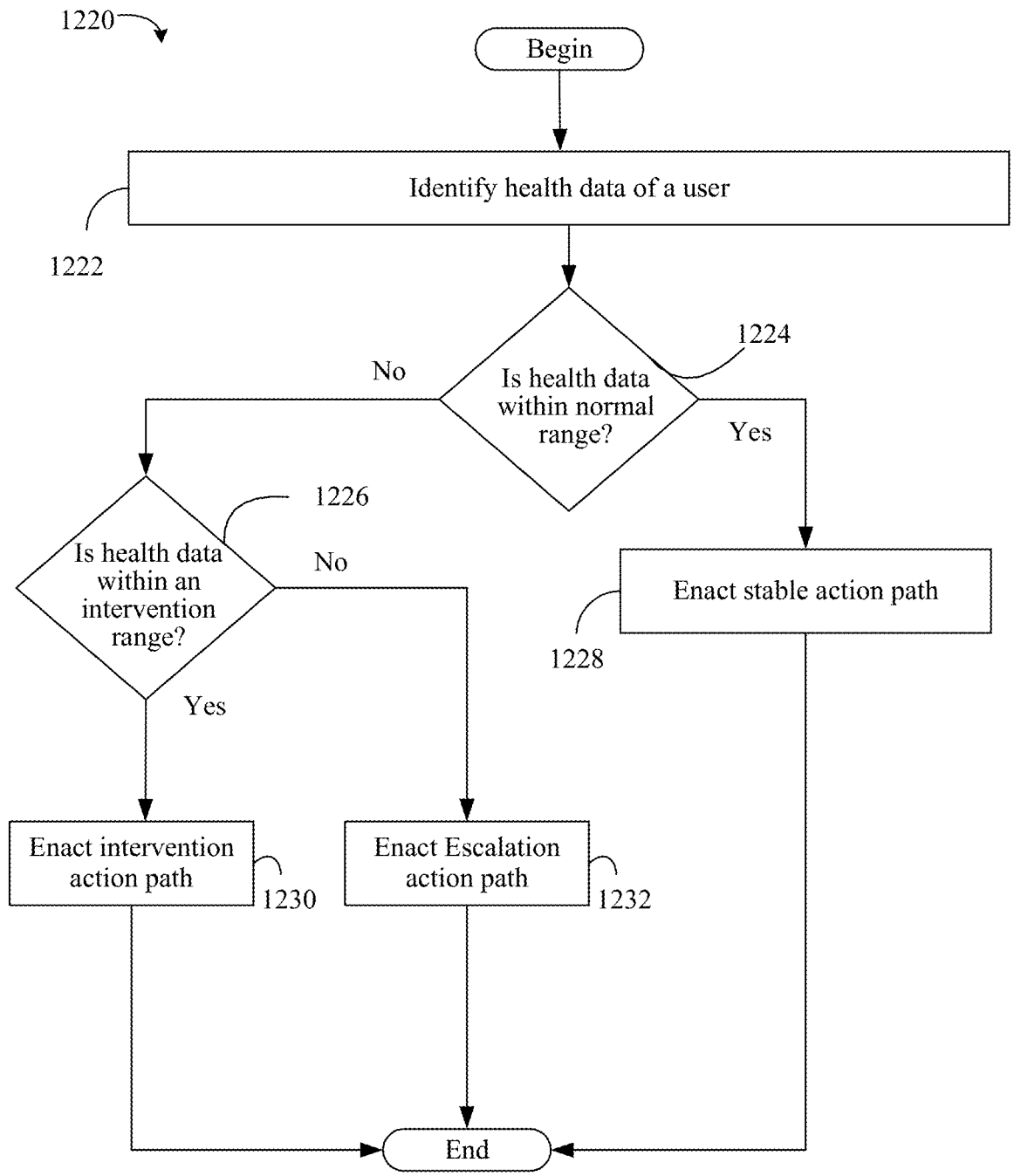
FIG. 16 is a flowchart of an example of a method of selecting action pathways according to an embodiment.

FIG. 16 shows a method 1220 of selecting action pathways. The method 1220 can generally be implemented in conjunction with any of the embodiments described herein, for example the health monitoring system 100 (FIG. 1), database 152 (FIG. 2), outreach event selection system 156 (FIG. 3), user interfaces 400 (FIG. 4) and 500 (FIG. 5), process 600 (FIG. 6), software architecture 706 (FIG. 7), machine 800 (FIG. 8), neural network 902 (FIG. 9) and the health monitoring, identification and treatment process 1000 (FIG. 10A and noise reduction process 1050 (FIG. 11), health plan compliance process 1100 (FIG. 12), method 1150 (FIG. 13), method 1170 (FIG. 14) and/or method 1190 (FIG. 15). In an embodiment, the method 1220 is implemented in logic instructions (e.g., software), configurable logic, fixed-functionality hardware logic, computer readable instructions stored on at least one non-transitory computer readable storage medium that are executable to implement method 1220, circuitry, etc., or any combination thereof.

Illustrated processing block 1222 identifies health data of a user. Illustrated processing block 1224 determines if the health data is within a normal range. If not, illustrated processing block 1226 determines if the health data is within an intervention range (e.g., health data is slightly deviated from normal ranges). If not, illustrated processing block 1232 enacts an escalation action pathway. If the health data is within intervention range, illustrated processing block 1230 enacts an intervention action pathway. If processing block 1224 determines that the health data is within the normal range, illustrated processing block 1228 enacts a stable action pathway.

Figure 17:
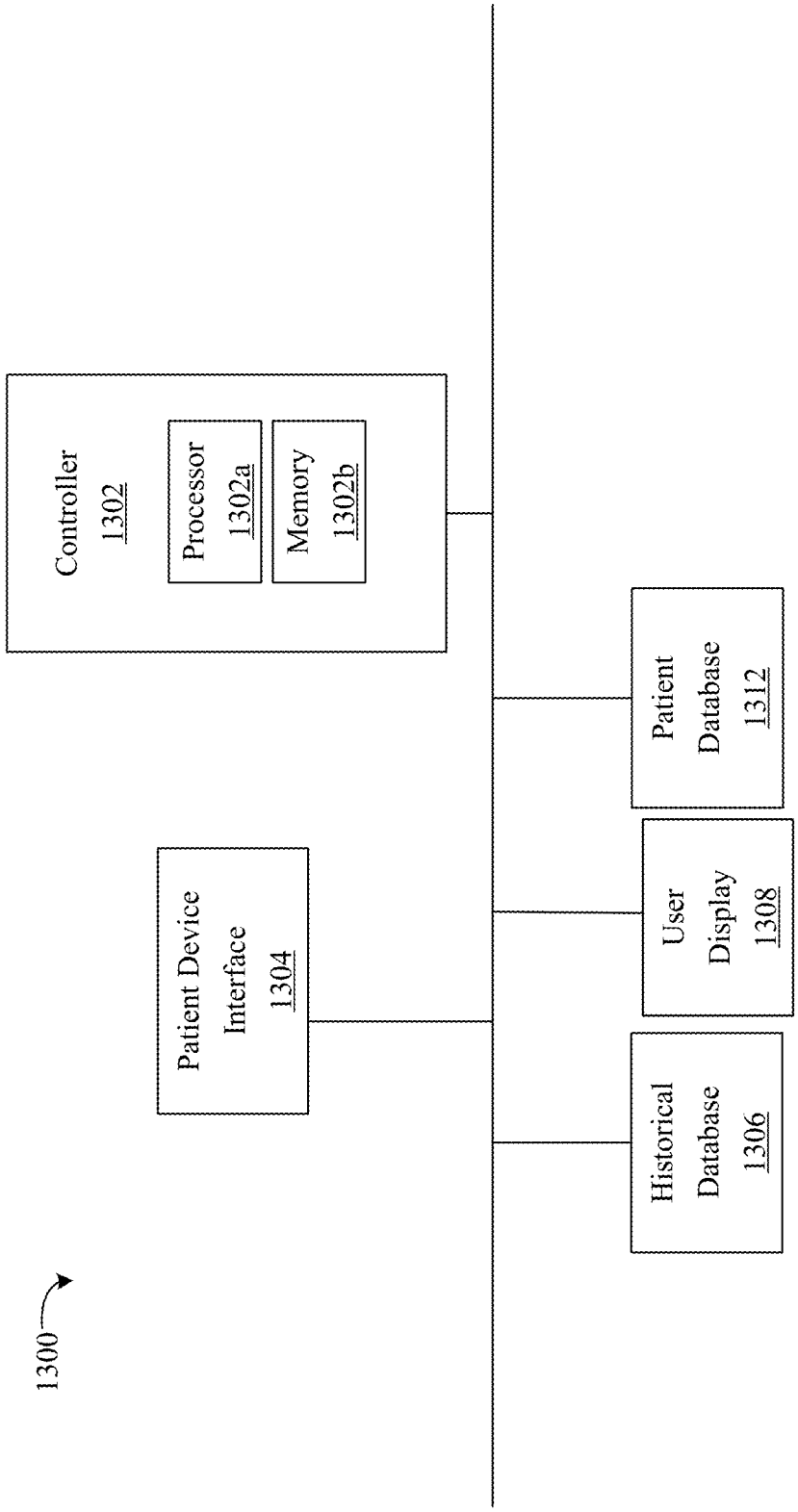
FIG. 17 is a block diagram of an example of a computing system according to an embodiment.

FIG. 17 shows a more detailed example of a computing system 1300 to diagnose a health condition, select an action plan and track compliance with the action plan. The illustrated computing system 1300 can be readily included in for example the health monitoring system 100 (FIG. 1), database 152 (FIG. 2), outreach event selection system 156 (FIG. 3), user interfaces 400 (FIG. 4) and 500 (FIG. 5), process 600 (FIG. 6), software architecture 706 (FIG. 7), machine 800 (FIG. 8), neural network 902 (FIG. 9) and the health monitoring, identification and treatment process 1000 (FIGS. 10A and 10B), noise reduction process 1050 (FIG. 11), health plan compliance process 1100 (FIG. 12), method 1150 (FIG. 13), method 1170 (FIG. 14), method 1190 (FIG. 15) and/or method 1220 (FIG. 16).

In the illustrated example, the computing system 1300 can include a patient device interface 1304 that can communicate with external devices (e.g., mobile devices, computers, smart watches, IoT devices, weigh scales, blood pressure cuff, etc.) to receive health measurements, environmental measurements and other data associated with the patient. The computing system 1300 also includes a user display 1308 (e.g., audio and/or visual interface) to display action plans and receive instructions from a user (e.g., an operator). The instructions can indicate an adjustment to an action plan. A historical database 1306 stores action plan data and outcomes associated with a plurality of patients, and a patient database 1312 stores information specific to the patient such as EMRs, family history information, previous health measurements, etc.

A controller 1302 can identify a patient, select first health data associated with the patient from a patient database, where the first health data includes a first health measurement of the patient, determine that the first health measurement is associated with a first health indication, where the first health indication is associated with a health condition, receive second health data in real-time from a first computing device associated with the patient, where the second health data is associated with the patient, determine that a second health measurement of the second health data is associated with a second health indication, select an action pathway from a first pathway, a second pathway and a third pathway based on the first and second health measurements being associated with the first and second health indications, automatically select a first action plan based on the action pathway. The first action plan includes a process flow to one or more of remediate the health condition and prevent an occurrence of the health condition in the patient, and the controller 1302 transmits a first outreach event to a second computing device of the patient over a computer network to implement the first action plan in real-time. The controller 1302 includes a processor 1302a (e.g., embedded controller, central processing unit/CPU) and a memory 1302b (e.g., non-volatile memory/NVM and/or volatile memory) containing a set of instructions, which when executed by the processor 1302a, cause the controller 1302 to generate an action plan based on data received from the patient device interface 1304, historical database 1306 and patient database 1312.

The computing systems described herein can add the real time monitored data to a longitudinal patient record (LPR), which can include a comprehensive medical profile of the patient sourced from numerous care providers, pharmacies, hospitals, third-party medical data vendors, the patient data, and the claims data, etc. The LPR can be a machine readable file that stores data relating to the individual's health. The manager device can create the LPR by compiling or aggregating received medical data (e.g., files) from numerous channels, including data already stored in the storage device, as will be described in greater detail below. The LPR can include patient demographics, encounters with care providers, patient vital signs gathered by care providers, medications prescribed to the patient, immunizations that the patient received, procedures performed on the patient, test results from tests performed on the patient, health goals set by the patient or the patient's care provider, care plans or medical treatment plans created by care providers for the patients, diagnoses or other health conditions of the patient, and social determinants of health. The LPR can further include data contributed by a user. For example, data contributed by a user can include information provided from a wearable or other device capable of providing health information. In some embodiments, the user may manually provide health information from an app or a website. The manager device can create the LPR in response to various external trigger messages, as will be described in more detail below. Additionally, the LPR can include a completeness score generated by the manager device or another device connected to the network. The completeness score can provide a numerical value indicative of the medical data's comprehensiveness and accuracy, which can provide added confidence to care providers seeking to use the LPR to learn about the patient before a patient arrives for medical care or to guide how medical care is to be administered. For example, an unconscious patient cannot answer medical history questions, so the doctor may rely on an LPR having a high completeness score to make informed medical decisions about the unconscious patient, which may save a patient's life (e.g., the doctor avoids certain medications identified as causing an allergy to the unconscious patient during the course of care). A completeness score for an individual can be based on the particular care path assigned to the patient's LPR. In an example embodiment, the completeness score can be weighted to reflect a particular procedure assigned to patient. In some circumstances a first completeness score relates to the overall health records of the patient and a second, specific procedure completeness score is assigned for a particular procedure/medical visit to be undertaken by the patient.

In one particular example, the manager device can create the LPR by aggregating or compiling patient data, claims data, and external data received from the health network utility in response to receiving an accept/discharge/transfer (ADT) message from a care provider on the network. In some embodiments, the ADT message comprises Health Level Seven (HL7) data transmitted on the network, and the ADT message can represent data associated with numerous medical events including admission of a patient to a care facility, discharging a patient from a care facility, changing an inpatient designation to an outpatient designation or vice versa, changing a patient ID, transferring a patient, or any other ADT message defined by HL7 or other protocol. The present system can be triggered to update the LPR upon an update to the patient record within a provider device or between provider devices. When different devices exchange patient related data, e.g., interface with each other, to send or receive new/updated patient data, that data is sent to the LPR.

The virtual charts comprise materialized views of data included in one or more than one LPRs. Said differently, each virtual chart can present data included in one or more than one LPRs and present the data in a specialized way according to preferences of a person or device that requested the virtual chart. For example, a first doctor may be an allergist, and the allergist may not need all medical data stored in the LPR, such as data submitted by an orthopedist, and so the virtual chart presented to the allergist may only contain some of the LPR data that is relevant to treating a patient's allergies. In another example, the manager device may generate a first virtual chart with medical data presented in a table form for a first data consumer (e.g., a first doctor), and the manager device may generate a second virtual chart with the same medical data presented as a graph for a second data consumer (e.g., a second doctor). The manager device may receive preferences from a data consumer, such as one of the provider devices or the user device, and generate a virtual chart in response to receiving those parameters or in response to other query information provided at the time the virtual chart was requested. In another embodiment, the preferences may be previously set and stored in the storage device. The virtual charts can also change in format depending on the time requested because medical data may have changed between a first virtual chart request and a second virtual chart request.

Example methods and systems for updating and curating data are described. More specifically, example methods and systems for receiving medical data from numerous sources or channels at defined trigger messages or events and curating the data at the defined trigger messages or events to create an LPR are described. Furthermore, example methods and systems for presenting updated and curated data according to user preferences is described. In the following description, for purposes of explanation, numerous specific details are set forth in order to provide a thorough understanding of example embodiments. It will be evident, however, to one of ordinary skill in the art that embodiments of the present disclosure may be practiced without these specific details.

Typically, medical data for an individual is scattered across numerous data storage locations controlled by various entities. For example, a hospital may store an EMR for an individual on a data storage device controlled by the hospital, and the hospital's EMR may store medical data related to an emergency room visit by the individual or surgery performed at the hospital on the individual. Meanwhile, a pharmacy may store prescription drug fulfillment history for the individual on a data storage device controlled by the pharmacy, and a primary care doctor may store vital sign information from yearly physicals administered to the individual on a data storage device controlled by the primary care physician's office. However, in this example, none of the hospital, the pharmacy, or the primary care physician has a complete medical record for the individual. In addition, medical data for the individual may be stale at one or more than one of the above-described entities. For example, the hospital may have vital sign data when a patient had a knee surgery operation in 2015, but the patient may have since developed a high blood pressure condition, rendering the hospital's blood pressure reading stale, outdated, and of little value.

Creating a single electronic health record for an individual reflecting all the medical events associated with the individual can be very difficult. To begin, a single entity would need to receive data from all care providers that provided care to the individual, and the single entity would need to convince every care provider to share this private medical data. Additionally, while medical data networks exist whereby entities, such as insurance companies or other care providers, can request information related to an individual, the information may not have a consistent format, may have incorrect, outdated, or conflicting information, or may simply be too much information for a single computer to manage. Said differently, gathering all EMRs associated with a single individual may not actually provide an accurate or complete health picture of the individual even using the existing networks and medical data sharing providers that currently exist. Thus, there is a need to curate all medical data associated with each individual in order to create a comprehensive and accurate EMR for individuals.

While some methods for curating data might exists, such curation methods are either use case based or constant. Constant medical data curation causes an incredible strain on data computing resources. Such constant medical data curation is costly because it requires frequent requests to either the provider devices or the health network utility, and requests to either of those entities may cost money to or impact the resources of the requester. In addition, even if a device associated with the requesting entity were able to make frequent, inexpensive or free requests for medical data, the processing power required to curate massive amounts of data would be unreasonably burdensome, particularly for a significantly large population of individuals, a population size that may be desirable to generate a large enough sample size to run certain analytic processes. For example, an insurance company may have millions of patients, and constantly curating medical data for millions of patients may not be feasible, efficient, or possible for even modern computing. Use case curation, on the other hand, may not generate an accurate snapshot of an individual's health because the curation is not run at appropriate times or might become stale very quickly. In either situation, better data curation methods are needed in the medical field (or any other field, such as government benefits, financial records, credit reports, etc.)

Finally, even if an entity were able to efficiently curate medical data from numerous sources or channels, the data must still be accurate enough to be useful for data consumers, such as care providers or insurance companies seeking to manage patient risk. That is, simply because an entity can combine medical data from multiple sources does not mean that the data is accurate or useful to other data consumers (e.g., doctors, care providers, pharmacies, etc.). Thus, the data must be curated in an effective manner so that the data reflects the most updated, most accurate, and most complete representation of an individual's health. If medical data created from multiple sources were not curated in this manner, the data consumers may not trust the data or may not find it useful for providing care, and the data consumers may try to acquire the medical data through other means (e.g., asking the patient to fill out numerous forms, generating the data themselves, etc.).

At the same time, any medical record must be complete to provide an accurate representation of the medical conditions and care, which requires management of both historical data and current state data. For example, an individual may have developed high blood pressure 10 years ago, but due to diet, exercise, lowered stress, medication, or all the above, the individual no longer suffers from high blood pressure. A complete medical record should store historical data because the individual was, at one time, diagnosed with high blood pressure, and knowing that medical history may be useful for some medical procedures or care. However, the medical record must also recognize the current state of the individual, whereby the individual's vital signs no longer exhibit high blood pressure. Thus, to generate a complete and accurate medical record, a computer would differentiate, categorize, and present data meaningfully, depending on context or preferences, so that a care provider or other data consumer can understand both the patient's medical history and current status. Moreover, data as presented should make sense to the recipient. For example, a patient may not understand medical data in the form of test readings and complicated medical terminology, whereas a doctor would. More granularly, a first doctor may not find all medical data associated with an individual relevant to his, her, or their practice, and so, irrelevant information should not be presented to every care provider. So, data presentation should account for the audience in how it is presented so that the data provided best communicates medical condition to a recipient.

The systems and methods described herein address the above-described issues by curating data in response to meaningful trigger messages. The trigger messages may be related to medical health events, which generate messages on medical networks, such as HL7 messages or any other protocol. For example, the trigger messages can include ADT messages, insurance claim submissions, appointment scheduling, and insurance eligibility submissions. By curating data in response to trigger messages, the processing load on the manager device is reduced so that data curation is only performed at meaningful times. Moreover, the identified trigger messages listed above represent that an individual is about to undergo medical care, is currently undergoing medical care, or recently received medical care, meaning that the trigger represents a significant and meaningful time in the health history of the patient. Thus, curating the data at that point indicates that any request made in response to the trigger should result in a complete medical picture for the individual. In response to one of the trigger messages, the systems and methods described herein can receive data from numerous sources, compiling or aggregating the received data, and curate the data, thereby creating an LPR.

The present machine learning systems and methods described herein can run on the LPR, which may provide insights for generating models of healthcare across populations and for specific individuals to be assigned care paths.

Glossary:

"CARRIER SIGNAL" in this context refers to any intangible medium that is capable of storing, encoding, or carrying transitory or non-transitory instructions for execution by the machine, and includes digital or analog communications signals or other intangible medium to facilitate communication of such instructions. Instructions may be transmitted or received over the network using a transitory or non-transitory transmission medium via a network interface device and using any one of a number of well-known transfer protocols.

"CLIENT DEVICE" in this context refers to any machine that interfaces to a communications network to obtain resources from one or more server systems or other client devices. A client device may be, but is not limited to, a mobile phone, desktop computer, laptop, PDA, smart phone, tablet, ultra-book, netbook, laptop, multi-processor system, microprocessor-based or programmable consumer electronics, game console, set-top box, or any other communication device that a user may use to access a network.

"COMMUNICATIONS NETWORK" in this context refers to one or more portions of a network that may be an ad hoc network, an intranet, an extranet, a virtual private network (VPN), a LAN, a wireless LAN (WLAN), a wide area network (WAN), a wireless WAN (WWAN), a metropolitan area network (MAN), the Internet, a portion of the Internet, a portion of the Public Switched Telephone Network (PSTN), a plain old telephone service (POTS) network, a cellular telephone network, a wireless network, a Wi-Fi® network, another type of network, or a combination of two or more such networks. For example, a network or a portion of a network may include a wireless or cellular network and the coupling may be a Code Division Multiple Access (CDMA) connection, a Global System for Mobile communications (GSM) connection, or other type of cellular or wireless coupling. In this example, the coupling may implement any of a variety of types of data transfer technology, such as Single Carrier Radio Transmission Technology (1xRTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, Universal Mobile Telecommunications System (UMTS), High Speed Packet Access (HSPA), Worldwide Interoperability for Microwave Access (WiMAX), Long Term Evolution (LTE) standard, others defined by various standard setting organizations, other long range protocols, or other data transfer technology.

"MACHINE-READABLE MEDIUM" in this context refers to a component, device, or other tangible media able to store instructions and data temporarily or permanently and may include, but is not limited to, random-access memory (RAM), read-only memory (ROM), buffer memory, flash memory, optical media, magnetic media, cache memory, other types of storage (e.g., Erasable Programmable Read-Only Memory (EEPROM)) and/or any suitable combination thereof. The term "machine-readable medium" should be taken to include a single medium or multiple media (e.g., a centralized or distributed database, or associated caches and servers) able to store instructions. The term "machine-readable medium" shall also be taken to include any medium, or combination of multiple media, that is capable of storing instructions (e.g., code) for execution by a machine, such that the instructions, when executed by one or more processors of the machine, cause the machine to perform any one or more of the methodologies described herein. Accordingly, a "machine-readable medium" refers to a single storage apparatus or device, as well as "cloud-based" storage systems or storage networks that include multiple storage apparatus or devices. The term "machine-readable medium" excludes signals per se.

"COMPONENT" in this context refers to a device, physical entity, or logic having boundaries defined by function or subroutine calls, branch points, APIs, or other technologies that provide for the partitioning or modularization of particular processing or control functions. Components may be combined via their interfaces with other components to carry out a machine process. A component may be a packaged functional hardware unit designed for use with other components and a part of a program that usually performs a particular function of related functions. Components may constitute either software components (e.g., code embodied on a machine-readable medium) or hardware components. A "hardware component" is a tangible unit capable of performing certain operations and may be configured or arranged in a certain physical manner. In various example embodiments, one or more computer systems (e.g., a stand-alone computer system, a client computer system, or a server computer system) or one or more hardware components of a computer system (e.g., a processor or a group of processors) may be configured by software (e.g., an application or application portion) as a hardware component that operates to perform certain operations as described herein.

A hardware component may also be implemented mechanically, electronically, or any suitable combination thereof. For example, a hardware component may include dedicated circuitry or logic that is permanently configured to perform certain operations. A hardware component may be a special-purpose processor, such as a Field-Programmable Gate Array (FPGA) or an ASIC. A hardware component may also include programmable logic or circuitry that is temporarily configured by software to perform certain operations. For example, a hardware component may include software executed by a general-purpose processor or other programmable processor. Once configured by such software, hardware components become specific machines (or specific components of a machine) uniquely tailored to perform the configured functions and are no longer general-purpose processors. It will be appreciated that the decision to implement a hardware component mechanically, in dedicated and permanently configured circuitry, or in temporarily configured circuitry (e.g., configured by software) may be driven by cost and time considerations. Accordingly, the phrase "hardware component" (or "hardware-implemented component") should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware components are temporarily configured (e.g., programmed), each of the hardware components need not be configured or instantiated at any one instance in time. For example, where a hardware component comprises a general-purpose processor configured by software to become a special-purpose processor, the general-purpose processor may be configured as respectively different special-purpose processors (e.g., comprising different hardware components) at different times. Software accordingly configures a particular processor or processors, for example, to constitute a particular hardware component at one instance of time and to constitute a different hardware component at a different instance of time.

Hardware components can provide information to, and receive information from, other hardware components. Accordingly, the described hardware components may be regarded as being communicatively coupled. Where multiple hardware components exist contemporaneously, communications may be achieved through signal transmission (e.g., over appropriate circuits and buses) between or among two or more of the hardware components. In embodiments in which multiple hardware components are configured or instantiated at different times, communications between such hardware components may be achieved, for example, through the storage and retrieval of information in memory structures to which the multiple hardware components have access. For example, one hardware component may perform an operation and store the output of that operation in a memory device to which it is communicatively coupled. A further hardware component may then, at a later time, access the memory device to retrieve and process the stored output.

Hardware components may also initiate communications with input or output devices and can operate on a resource (e.g., a collection of information). The various operations of example methods described herein may be performed, at least partially, by one or more processors that are temporarily configured (e.g., by software) or permanently configured to perform the relevant operations. Whether temporarily or permanently configured, such processors may constitute processor-implemented components that operate to perform one or more operations or functions described herein. As used herein, "processor-implemented component" refers to a hardware component implemented using one or more processors. Similarly, the methods described herein may be at least partially processor-implemented, with a particular processor or processors being an example of hardware. For example, at least some of the operations of a method may be performed by one or more processors or processor-implemented components. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an API). The performance of certain of the operations may be distributed among the processors, not only residing within a single machine, but deployed across a number of machines. In some example embodiments, the processors or processor-implemented components may be located in a single geographic location (e.g., within a home environment, an office environment, or a server farm). In other example embodiments, the processors or processor-implemented components may be distributed across a number of geographic locations.

"PROCESSOR" in this context refers to any circuit or virtual circuit (a physical circuit emulated by logic executing on an actual processor) that manipulates data values according to control signals (e.g., "commands," "op codes," "machine code," etc.) and which produces corresponding output signals that are applied to operate a machine. A processor may, for example, be a CPU, a RISC processor, a CISC processor, a GPU, a DSP, an ASIC, a RFIC, or any combination thereof. A processor may further be a multi-core processor having two or more independent processors (sometimes referred to as "cores") that may execute instructions contemporaneously.

"TIMESTAMP" in this context refers to a sequence of characters or encoded information identifying when a certain event occurred, for example giving date and time of day, sometimes accurate to a small fraction of a second.

Changes and modifications may be made to the disclosed embodiments without departing from the scope of the present disclosure. These and other changes or modifications are intended to be included within the scope of the present disclosure, as expressed in the following claims.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

What is claimed is:

1. At least one computer readable, nontransitory storage medium comprising a set of executable program instructions, which when executed by a computing system, cause the computing system to:
    select a given group of monitoring information to collect from a user;
    instruct a first computing device associated with the user to collect the given group of monitoring information;
    determine that the given group of monitoring information is unavailable to be provided by the first computing device;
    determine a class associated with the first computing device;
    instruct the first computing device to re-collect the given group of monitoring information based on determining the class associated with the first computing device;
    apply a machine learning model to the class associated with the first computing device to determine whether to instruct the first computing device to re-collect the given group of monitoring information, wherein the machine learning model comprises a neural network, the machine learning model being trained to establish a relationship between a plurality of training computing device class features and re-reading requests;
    obtain a batch of training data comprising a first set of the plurality of training computing device class features associated with re-reading requests;
    process the first set of the plurality of training computing device class features by the machine learning model to generate an estimated need for a re-reading request;
    compute a loss based on a deviation between the estimated need for a re-reading request and the re-reading requests associated with the first set of the plurality of training computing device class features;
    update parameters of the machine learning model based on the computed loss;
    in response to the given group of monitoring information being determined as being unavailable to be provided by the first computing device, generate an outreach event to request the given group of monitoring information from the user; and in response to the given group of monitoring information being determined as being available, select an action pathway for the user.

2. The at least one computer readable storage medium of claim 1, wherein the instructions, when executed, further cause the computing system to:
obtaining a timestamp corresponding to when the first computing device was instructed to collect the given group of monitoring information;
measuring a duration of time between a current time and the timestamp;
comparing the duration of time to a threshold; and
causing the outreach event to be generated in response to determining that the duration of time transgresses the threshold.

3. The at least one computer readable storage medium of claim 1, wherein the instructions, when executed, further cause the computing system to:
accessing previously collected monitoring information associated with the user; and
searching the previously collected monitoring information for the given group of monitoring information.

4. The at least one computer readable storage medium of claim 3, wherein the instructions, when executed, further cause the computing system to:
retrieve an instance of the given group of monitoring information from the previously collected monitoring information; and
accessing a timestamp associated with the retrieved instance.

5. The at least one computer readable storage medium of claim 4, wherein the instructions, when executed, further cause the computing system to:
measuring a duration of time between a current time and the timestamp;
comparing the duration of time to a threshold; and
causing the outreach event to be generated in response to determining that the duration of time transgresses the threshold.

6. The at least one computer readable storage medium of claim 3, wherein the instructions, when executed, further cause the computing system to:
receive the given group of monitoring information from the first computing device;
determine that a value of the received given group of monitoring information fails to satisfy a criterion; and
instruct the first computing device to recollect the given group of monitoring information in response to determining that the value of the received given group of monitoring information fails to satisfy the criterion.

7. The at least one computer readable storage medium of claim 1, wherein the first computing device is an Internet of Things (IoT) monitoring device.

8. The at least one computer readable storage medium of claim 1, wherein the outreach event comprises one or more reminder messages transmitted to a client device of the user, each reminder message comprising a notification for the user to provide the given group of monitoring information using the first computing device.

9. The at least one computer readable storage medium of claim 8, wherein the instructions, when executed, further cause the computing system to:
determine that a quantity of the one or more reminder messages previously sent to the client device transgresses a threshold quantity; and
transmit a message to a third-party device associated with a third-party in response to determining that the quantity of the one or more reminder messages previously sent to the client device transgresses the threshold quantity.

10. The at least one computer readable storage medium of claim 1, wherein the given group of monitoring information comprises at least one of blood pressure information, aerobic activity information, body mass index (BMI) information, sodium intake information, arrhythmia information, or glucose information.

11. The at least one computer readable storage medium of claim 1, wherein the instructions, when executed, further cause the computing system to:
access a list of first computing device classes that are associated with re-collecting monitoring information; and
determine that the class associated with the first computing device is included in the list of first computing device classes.

12. The at least one computer readable storage medium of claim 1, wherein the instructions, when executed, further cause the computing system to:
receive the given group of monitoring information from the first computing device;
identify first data, wherein the first data is associated with the user and includes a first measurement of the user;
determine that the first measurement is associated with a first indication, wherein the first indication is associated with a condition of the user;
identify second data from the received given group of monitoring information;
determine that a second measurement of the second data is associated with a second indication, wherein the second indication is associated with the condition;
select the action pathway from a first pathway, a second pathway, and a third pathway based on the first measurement being associated with the first indication, and the second measurement being associated with the second indication;
automatically select a first action plan based on the action pathway, wherein the first action plan includes a process flow to one or more of remediate the condition of the user or prevent an occurrence of the condition; and
transmit a first outreach event to a second computing device of the user over a computer network to implement the first action plan in real-time.

13. The at least one computer readable storage medium of claim 12, wherein the instructions, when executed, further cause the computing system to:
identify activity of the user based on third data associated with the user, wherein the third data is associated with an internet-of-things sensor associated with the user;
determine whether the activity corresponds to an expected action associated with the first action plan;
determine whether the user is in compliance with the first action plan based on whether the activity corresponds to the expected action;
if the user is in compliance with the first action plan, maintain the first action plan, generate a response, and provide the response to the user; and
if the user is not in compliance with the first action plan, generate a penalty for the user,
adjust the first action plan to generate a second action plan, and
transmit a second command to the second computing device to implement the second action plan.

14. The at least one computer readable storage medium of claim 13, wherein the instructions, when executed, further cause the computing system to:
  generate a first metric for the first action plan based on whether the user is in compliance with the first action plan;
  generate a second metric for a second action plan based on past data, wherein the past data is associated with a plurality of users; and
  cease implementation of the first action plan and implement the second action plan based on a comparison of the first metric and the second metric,
  wherein the first metric is a probability that the user will comply with the first action plan, and the second metric is a probability that the user will comply with the second action plan.

15. The at least one computer readable storage medium of claim 12, wherein the instructions, when executed, further cause the computing system to:
  train a machine learning prediction model based on past data associated with a plurality of users, wherein the machine learning prediction model is trained to predict whether an action plan in the past data is associated with a particular outcome based on the past data; and
  generate, with the machine learning prediction model, the first action plan.

16. A computing system comprising:
  a processor; and
  a memory having a set of instructions, which when executed by the processor, cause the computing system to:
  select a given group of monitoring information to collect from a user;
  instruct a first computing device associated with the user to collect the given group of monitoring information;
  determine that the given group of monitoring information is unavailable to be provided by the first computing device;
  determine a class associated with the first computing device;
  instruct the first computing device to re-collect the given group of monitoring information based on determining the class associated with the first computing device;
  apply a machine learning model to the class associated with the first computing device to determine whether to instruct the first computing device to re-collect the given group of monitoring information, wherein the machine learning model comprises a neural network, the machine learning model being trained to establish a relationship between a plurality of training computing device class features and re-reading requests;
  obtain a batch of training data comprising a first set of the plurality of training computing device class features associated with re-reading requests;
  process the first set of the plurality of training computing device class features by the machine learning model to generate an estimated need for a re-reading request;
  compute a loss based on a deviation between the estimated need for a re-reading request and the re-reading requests associated with the first set of the plurality of training computing device class features;
  update parameters of the machine learning model based on the computed loss;
  in response to the given group of monitoring information being determined as being unavailable to be provided by the first computing device, generate an outreach event to request the given group of monitoring information from the user; and
  in response to the given group of monitoring information being determined as being available, select an action pathway for the user.

17. The computing system of claim 16, wherein the set of instructions, when executed, further cause the computing system to:
  obtaining a timestamp corresponding to when the first computing device was instructed to collect the given group of monitoring information;
  measuring a duration of time between a current time and the timestamp;
  comparing the duration of time to a threshold;
  causing the outreach event to be generated in response to determining that the duration of time transgresses the threshold;
  accessing previously collected monitoring information associated with the user; and
  searching the previously collected monitoring information for the given group of monitoring information.

18. The computing system of claim 16, wherein the instructions, when executed, further cause the computing system to:
  receive the given group of monitoring information from the first computing device;
  identify first data, wherein the first data is associated with the user and includes a first measurement of the user;
  determine that the first measurement is associated with a first indication, wherein the first indication is associated with a condition of the user;
  identify second data from the received given group of monitoring information;
  determine that a second measurement of the second data is associated with a second indication, wherein the second indication is associated with the condition;
  select the action pathway from a first pathway, a second pathway, and a third pathway based on the first measurement being associated with the first indication, and the second measurement being associated with the second indication;
  automatically select a first action plan based on the action pathway, wherein the first action plan includes a process flow to one or more of remediate the condition of the user or prevent an occurrence of the condition; and
  transmit a first outreach event to a second computing device of the user over a computer network to implement the first action plan in real-time.

19. The computing systems of claim 18, wherein the instructions, when executed, further cause the computing system to:
  identify activity of the user based on third data associated with the user, wherein the third data is associated with an internet-of-things sensor associated with the user;
  determine whether the activity corresponds to an expected action associated with the first action plan;
  determine whether the user is in compliance with the first action plan based on whether the activity corresponds to the expected action;
  if the user is in compliance with the first action plan, maintain the first action plan, generate a response, and provide the response to the user; and
  if the user is not in compliance with the first action plan, generate a penalty for the user,
  adjust the first action plan to generate a second action plan, and transmit a second command to the second computing device to implement the second action plan.

20. A method comprising:

selecting a given group of monitoring information to collect from a user;

instructing a first computing device associated with the user to collect the given group of monitoring information;

determining that the given group of monitoring information is unavailable to be provided by the first computing device;

determine a class associated with the first computing device;

instruct the first computing device to re-collect the given group of monitoring information based on determining the class associated with the first computing device;

apply a machine learning model to the class associated with the first computing device to determine whether to instruct the first computing device to re-collect the given group of monitoring information, wherein the machine learning model comprises a neural network, the machine learning model being trained to establish a relationship between a plurality of training computing device class features and re-reading requests;

obtain a batch of training data comprising a first set of the plurality of training computing device class features associated with re-reading requests;

process the first set of the plurality of training computing device class features by the machine learning model to generate an estimated need for a re-reading request;

compute a loss based on a deviation between the estimated need for a re-reading request and the re-reading requests associated with the first set of the plurality of training computing device class features;

update parameters of the machine learning model based on the computed loss;

in response to the given group of monitoring information being determined as being unavailable to be provided by the first computing device, generating an outreach event to request the given group of monitoring information from the user; and in response to the given group of monitoring information being determined as being available, select an action pathway for the user.

* * * * *